US008829177B2

(12) United States Patent
Rhoads et al.

(10) Patent No.: US 8,829,177 B2
(45) Date of Patent: Sep. 9, 2014

(54) ENHANCED ENGINEERED NATIVE PROMOTERS AND USES THEREOF

(75) Inventors: David B. Rhoads, Needham Heights, MA (US); Jianmin Huang, Lexington, MA (US); Lynne L. Levitsky, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/375,587

(22) PCT Filed: Jun. 5, 2010

(86) PCT No.: PCT/US2010/037551
§ 371 (c)(1),
(2), (4) Date: Dec. 28, 2011

(87) PCT Pub. No.: WO2010/141924
PCT Pub. Date: Dec. 9, 2010

(65) Prior Publication Data
US 2012/0094375 A1    Apr. 19, 2012

Related U.S. Application Data

(60) Provisional application No. 61/184,475, filed on Jun. 5, 2009.

(51) Int. Cl.
*C07H 21/02* (2006.01)
(52) U.S. Cl.
USPC ......................... 536/24.1; 536/23.1; 536/24.2
(58) Field of Classification Search
CPC ........... C12N 2830/15; C12N 2830/00; C12N 2830/30; C12N 15/85
See application file for complete search history.

(56) References Cited

U.S. PATENT DOCUMENTS

| | | | |
|---|---|---|---|
| 7,267,978 | B1 | 9/2007 | Carey et al. |
| 2006/0089492 | A1 | 4/2006 | Suckow |

OTHER PUBLICATIONS

Han, et al. (2007) "MafA stability in pancreatic [beta] cells is regulated by glucose and is dependent on its constitutive phosphorylation at multiple sites by glycogen synthase kinase 3", Molecular and Cellular Biology, 27(19): 6593-6605.*
Suzuki, et al. (1996) "Regulatable Promoters for Use in Gene Therapy Applications: Modification of the 5'-Flanking Region of the CFTR Gene with Multiple cAMP Response Elements to Support Basal, Low-Level Gene Expression That Can Be Upregulated by Exogenous Agents That Raise Intracellular Levels of cAMP", Human Gene Therapy, 7: 1883-93.*
German et al., Molecular and Cellular Biology, 12(4):1777-1788 (1992). "The insulin and islet polypeptide genes contain similar cell-specific promoter elements that bind identical beta-cell nuclear complexes."
Sander et al., PNAS, 95:11572-11577 (1998). "A novel glucose-responsive element in the human insulin gene functions uniquely in primary cultured islets."
Fraser et al., Curr. Opin. Cell Biol., 10:361-365 (1998). "Locus control regions, chromatin activation and transcription."
German et al., Mol. Cell Biol., 12:1777-1788 (1992). "The insulin and islet amyloid polypeptide genes contain similar cell-specific promoter elements that bind identical beta-cell nuclear complexes."
Gossen et al., Annu. Rev. Genet., 36:153-173 (2002). "Studying gene function in eukaryotes by conditional gene inactivation."
Grosveld et al., Cell, 51:975-985 (1987). "Position-independent, high-level expression of the human beta-globin gene in transgenic mice."
Huang et al., Journal of Biotechnology, 150:259-267 (2010). "Boosting native promoter activities with non-adjacent response-element multimers."
Hwang et al., Hum. Gene Ther., 12:1731-1740 (2001). "A high-efficiency synthetic promoter that drives transgene expression selectively in noradrenergic neurons."
Kaluz et al., Biochem. Biophys. Res. Commun., 370:613-618 (2008). "Rational design of minimal hypoxia-inducible enhancers."
Li et al., Blood,100:3077-3086 (2002). "Locus control regions."
Nam et al., Mol. Ther., 13:15-25 (2006). "The role of LMO2 in development and in T cell leukemia after chromosomal translocation or retroviral insertion."
Okita et al., Nature, 448:313-317 (2007). "Generation of germline-competent induced pluripotent stem cells."
Sander et al., Proc. Natl. Acad. Sci. U. S. A., 95:11572-11577 (1998). "A novel glucose-responsive element in the human insulin gene functions uniquely in primary cultured islets."
Shaw et al., Gene Ther. 16:998-1008 (2009). "Lentiviral vectors with amplified b cell-specific gene expression."
Veeman et al., Curr. Biol., 13:680-685 (2003). "Zebrafish prickle, a modulator of noncanonical Wnt/Fz signaling, regulates gastrulation movements."
Venter et al., J. Cell Mol. Med., 13:270-278 (2009). "In silico promoters: modelling of cis-regulatory context facilitates target prediction."
Wang et al., Hum. Gene Ther., 10:1763-1771 (1999). "Diverse stabilities of expression in the rat brain from different cellular promoters in a helper virus-free herpes simplex virus type 1 vector system."
Wang et al., Neurobiol. Dis., 16:596-603 (2004). "A preproenkephalin-neurofilament chimeric promoter in a helper virus-free herpes simplex virus vector enhances long-term expression in the rat striatum."
Yamada et al., Retrovirology, 6:79 (2009). "Identification of a high incidence region for retroviral vector integration near exon 1 of the LMO2 locus."
Zaret et al., Proc. Natl. Acad. Sci. U. S. A., 85: 9076-9080 (1988). "Conditional enhancement of liver-specific gene transcription."

* cited by examiner

*Primary Examiner* — Robert M Kelly
(74) *Attorney, Agent, or Firm* — David S. Resnick; Nixon Peabody LLP

(57) ABSTRACT

We describe methods and DNA constructs/engineered mammalian promoters to enhance native promoter activity while retaining inherent regulation by inserting multi-copy response elements (REs) into non-adjacent locations. Multiple copies of REs are clustered in a group forming a transcription factor response element segment. The segment is at least duplicated in tandem upstream of the ATG start codon. Spacers of 0.2-0.7 kilo base pairs are introduced between the two segments and smaller spacers of about between 9-15 bp are introduced between the copies of REs within a segment.

13 Claims, 26 Drawing Sheets

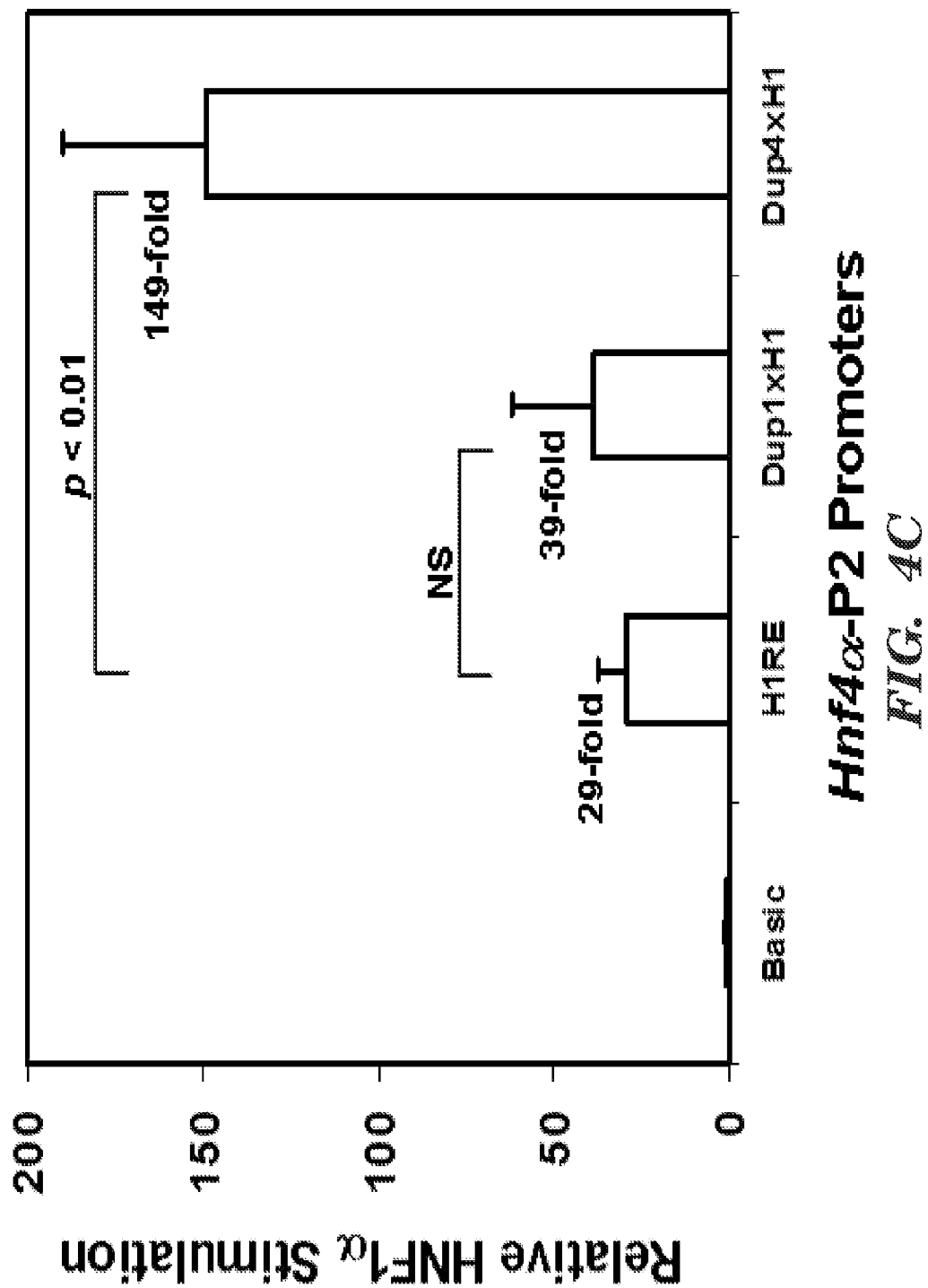

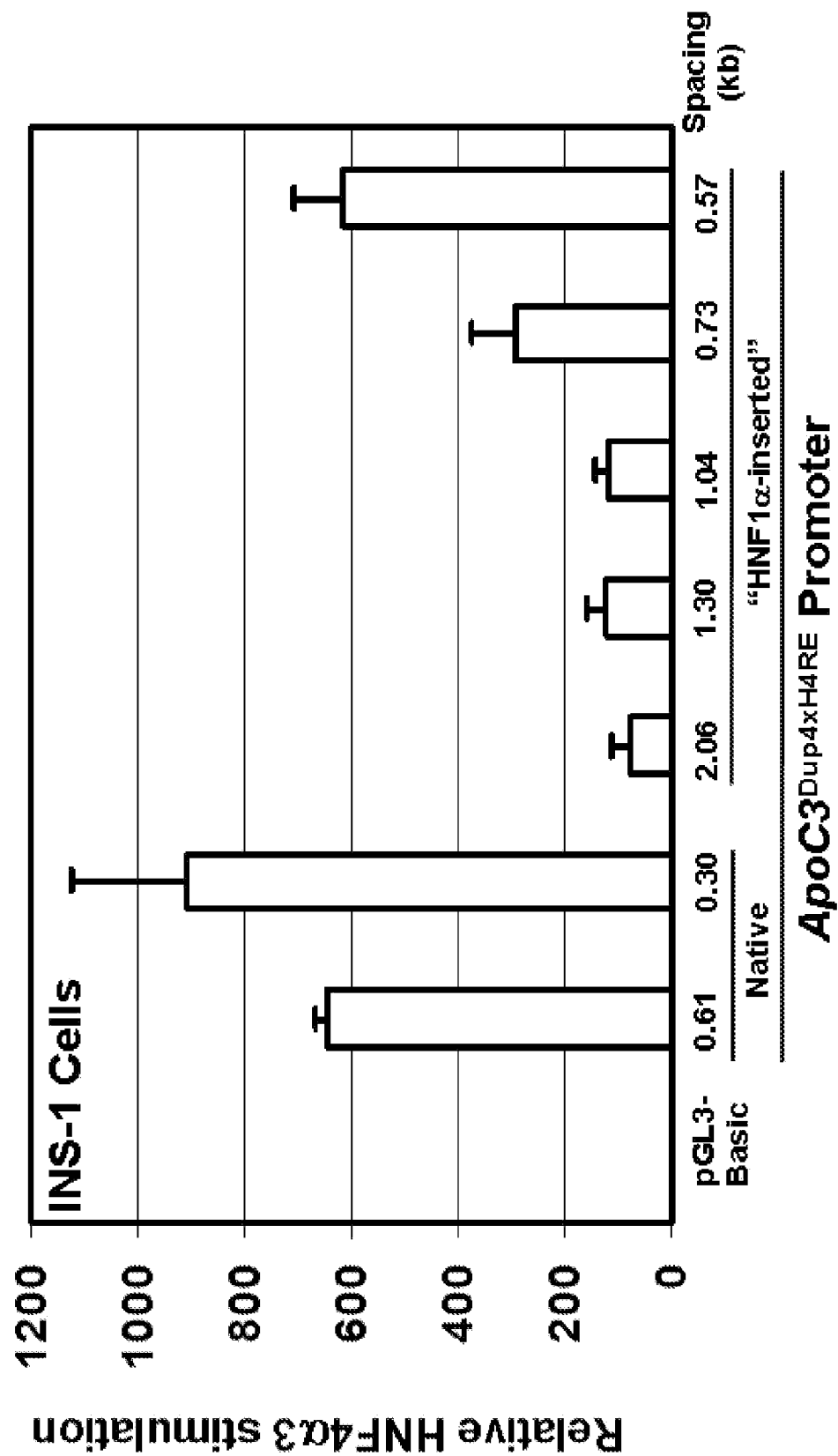

gagctcagtatcctcaacacagaagtctgaagtgctaagacaacaggggtttcccccctgggaag
tctgatgttgggctaggactgaggtgcagtgaccactccaggaaatgtgacctgattctgccctgg
agaaccggccagtggccagtgaggagcttcctgctgtcccagcggcccaaacagctcttaagttc
tcctgtgccaggctgaaagcatcctggagagtgggaccagcgcgcaccagagcctcctgctcc
tgctgcctctagcctgcgcccctgccgcccctctccacctccccccgccatgcctctgctcactcccaa
ttgcaggccatgactcccgtccccttcgctaagcgcacggataaatatgaaccttgagaattcccagctcaa
tccaaagttcagtccccttcgctaagcgcccctgattcactggccgtggggcttggggtgcc
tgtaaacagagcaggcaggcaggcccctgattcactggccgtggggcttgggggctggggtgcc
cacagagcttgactagtgacacccggcgcagtgggtgcagcgagcccgtccgttgactgccagc
ctgccggcaggcagtagacaccggcggctggtgggggaggcggctagctcagtggccttgggccgcgtggc
ctggtggcagcggagccATG (SEQ. ID NO. 1)

FIG. 7A

BlpI          NdeI           MluI            SalI
5'┤—TAAGCATGCCAAAGTTAATCATATGACAAGTCCAAAGTTAGGAGCGCTGAGTCCAAAGATCAGGTCGAC
3'┤—    CGTACGGTTTCAATTAGTATACTGTTCAGGTTTCCAATCCTCGCGACTCAGGTTTCTAGTCCAGCTGATT (SEQ. ID NO.2 and 3)

Tccccctctccacctcccccaccctccctttctgctcactcccaattgcaggccatgactcccgtccc
tctcaccggccatgagcccgtgcacttgcaaggctgactcccttcgctaagcgcacggataaat
atgaaccttggagaatttccccagctccaatgtcgactgtaaacagagcagcagcagcggataaat
gccagggttggggggctgggtgccagctgccgcagctgccacacagagcagcagtggtgcagcgagc
ccggtccgttgactgccagctgccgcaggtagacaccggccgtgggtgggtgggaggcggctagctcagtggc
cttgggccgcgtggcctggtgcgagcggagccATG (SEQ. ID NO. 4)

FIG. 7D

Tccccctctccacctccccaccctccctttctgctcactcccaattgcaggccatgactcccgtccc
gtccctctcaccgccatgaggcctgcacttgcaaggctgaagttccaaagatcagtccgcta
agdatgccaagttaatcatatgacaagtccaaagttaggagcgctgagtccaaagatcaggtcga
ctaagcgcacggataaatatgaaccttggagaatttcccccagctcccaatgtaaacagagcagcagg
ggccctgattcactggccgctgggtgccaggttggggcgccagggtgggcgtttgactagtg
ggatttggggggctgggtgcagtgggtgccagctgccgcagctgccacgagcagcagcttgactagaca
ccggccgtgggtggggggaggcgctagccgccaaggttggagcgctgagtccaaagatcagg
gctaagcatgccaaagttaatcatatgacaagttccccagctccaatgtaaacagagcagg
tcgactaagcgcacggataaatatgaaccttggagaatttccccagctcccaatgtgccacagagcttgact
caggggccctgattcactggccgcgtgggcaggtgggcaggttgggcgtccgcagcctgccgcaggta
agtgggatttggggggtggggtggggggaggccagctcagtggccttgggcgcgtggcctggtgcagcg
gagccATG (SEQ. ID NO.5)

gccctctccactccccacctccttctgctcactcccttctgctcactcccaattgcaggccatgactcccgtcccgtccctct
cacccgccatgaggcctgcacttgcaaggctgagtgaagtcagtccaaagttcagtcccttcgctaagcgcacggataaat
(SEQ. ID. NO:6)

gccctctccactccccacctccttctgctcactcccttctgctcactcccaattgcaggccatgactcccgtcccgtccctct
cacccgccatgaggcctgttaggtaaggctgaagtgaagtcagtccaaagttcagtcccttcgctaagcgcacggataaat
(SEQ. ID. NO:7)

*FIG. 7F*

GGTACCgggagggggcaaaggcttcgggctctgagcggcctggccttctccaccaaccccctg
cctacactaaggggaggcagcggggggcacacaggtggggcggtggggctgctggg
tgagcagcactcgcctgcctgattgaaaccagagatggaggtgctggaggggctgtgaga
gctcagccctgtaaccagccttgccgagccactgatgcctggtctttgccttactcc
aaacaccccagccaagcccaccagccaaagccctcaagtctgaagaagccctcaccctcta
ctccaggctgtgttcagggcttggggctggtggtggaggggagggcctgaaattccagtgtgaaag
gctgagatgggcccgaggcccctggcctatgtccaagccattccctctcaccagcctctcc
ctggggagccagtcagctaggaaggaatgagggctcccagccccccacccagttcctgagct
catctggctgcaggtgcggcgggacagcagcgtggactcagtcctcctaggatttcccaact
ctcccgcccgcttgctgcatctggacacctgcctcagcCCCTCATCTCCACTGGTCgctagc
TGGGCAAAGGTCAGCGCCCCTGGGTCCTCAGTGCCTGCTGCCCTGGAGATGATATAAAACAGGT
CAGAACCCTCCTAGATCT (SEQ. ID. NO. 8)

FIG. 8A

GGTACCAAGCAGTCCAAAGATCATGAATTCACAATGCCAAAGTTAACGTACGGCTGAGTCCAAAGTTC
AGGTCGAgggagggggcaaaggcctcgggctctgagcggtggggggcacacagggtggggcggtggggctgctggtgagcagca
acactaaggggggaggcagcgggggggcacacagagatggaggtgctgggaggctgtgaggctcagccctgtaa
ctcgcctgcctggattgaaaccagagatgcctggtcttctgtcttactccaaacaccccagcccaag
ccagccttgccggagcacttgttctcaagtctgaagaagccctcacccctctactccaggctgtgttcagggcttgg
ccaccactgtttctcaagtctgaagaagccctgaaattccagtgtgaaaggctgagatgggccgaggccctggccta
ggctgtgaggagggggctgaaattccagtgtgaaaggctgagatgggccgaggccctggccta
tgtccaagcattcccctctcaccagcctctctccctgggagccagtcagctaggaaggaatgaggc
tcccaggccccacccccagtctgagctcatctcccgcgcttgctgactcctgcctcaggCCCTC
cagtctcctaggatttccaactctccccgcgcttgtcatctgcccgcttgctgactcctgcctcaggCCCTC
ATCTCCACTGGTCATGCCAAAGTTAATACTAGTACAAGTCAGCATATGTGCCCTGGAGATGAT
ATCAGTCGACGCTAGCTGGGCAAAGTCAGCGCCCCTGGGTCCCAGTGCCTGCCTGCCCTGGAGATGAT
ATAAAACAGTCAGAACCCTCCTAGATCT [Sequence shown in Fig. 8A modified by introducing
an 3xH4RE segment adjacent to each H4RE using PCR primers shown below.]

AAATTTGCTAGCGTCGACTGATCTTTGGACTCACATATGCCTGAACTTTGTACTAGTATTAA
CTTTGGCATGACCAGTGGAGATGAGGcc [Apoc3/3xH4RE/NheI/SpeI/R (reverse primer inserts
three H4REs to create a proximal 4xH4RE motif by ligating into duplicate 1xH4RE promoter
NheI site)]

aaattTggtaccAAGCAGTCCAAAGATCATGAATTCACAATGCCAAAGTTAACGTACGGCTGAGTCCA
AAGTTCAGTCGAgggaggggggcaaaggcctc [Apoc3/4xH4RE/Acc65I/BsiWI/F (forward primer
converted distal H4RE to a 4xH4RE motif with flanking KpnI and BsiWI sites)]

*FIG. 8B*

GGTACCAAGCAGTCCAAAGATCATGAATTCACAAATGCCAAAGTTAACGTACGCTGAGTCCAAAGTTC
AGGTCGAGgggagggcaaaggcctcgggcctctgagcggcct tggccct tctccaaccctgccct
acactaaggggaggcagcgggggcacacaggtggggcgggtggggctgctgggtgagcagca
ctcgcctgcctgattgaaaccagagatggaggtgctggagggctgtgagagtcatctggctg
cagggctggcgggacagcagcgtggactcagtctcctaggatttccaactctcccgcgcttgct
gcatctggacaccctgcctcaggcCCCTCATCTCCACTGGTCATGCCAAAGTTAATACTAGTACAAGTC
CAAAGTTCAGGCATATGTGAGTCCAAAGATCAGATATAAAACAGTCAGAACCCTCCTAGATCT [Sequence
CCTCAGTGCCTGCTGCCCTGGAGATGATATAAAACAGTCAGAACCCTCCTAGATCT [Sequence
shown in Fig. 8B modified by removing 312 bps between the two GAGCTC SacI sites. The
4xH4RE segments are spaced 0.29 kb apart.]

FIG. 8C

```
GGTACCGAGCTCcccaagcagctggtgagatccaaaactgagacaaaagaaacggggctgttccaaaa
aaaagctaggtggcaggtgtctaacatgccaggagctaaaacagagtgtgagtttcagcagcag
gttgaatttagaatgggaaggagaccagaggagaccgccagaggatgacttttgtccattggcctg
gaggcagcccatgtgttctccacccctcatatcactcaccagtttgtaatagtatctttgaatgacga
tctgattaaggtccgtctcctccattagtccacaagttcgggggtacatctactttgctcatttcca
tatcccagagtctagcacaaggcctggtacatagtaggtgctcaataaatatgttagatgaaaggaa
gataacacctctatgtactagcagtgagactgccaggcatgcaattctctctgtcctttcagtccttc
atctcaagttttaatttaaatatggtaactcccctgtatgccccctcctgccctccctactccactta
aacacagttctccaccctctcctttttttcctcctgccctctgccttttccactacttcctgccctggt
gacacaccatagtttggagccataaaaacccaggttggactctccagctctcccagcctcctctg
ctccggccctgtcctcaaattgggggctgatgtcccatacaccggctctggttccctaacccc
agagtgcaggactaggacccgagtggacctcagtcgggccaggtcgccattgccatggagacagcaa
cagtccccagccgcgggttccctaagtgactggttactctttaacgtatccaccacctttgggtgatt
agaagaatcaataagataaccgggcggtggtgcagctggccactcaccgcctcaccgcctcctggtggacgggct
cctggctggctgtgtgctgtgagcggggcccctgctcctccatgccccagctctccggctCGAG

[HNF4A P2 1xH1RE (-1013/-11 from NM_175194; KpnI/SacI and XhoI sites incorporated via
PCR primers). The H1RE is highlighted.]
```

FIG. 9A

GGTACCtgctaatttttaacatttTGAGCTCcccaagcgcaggtggtgagatccaaaactgagacaaaa
gaaacgggctgttccaaaaaaaaagctaggtggcaggtgtctaacatgccaggagctaaaacagag
tgtgtgagtttcagcagcaggttgaatttagaatgggaaggagaccagaggagacgccagacaggat
gactttgtccattggcctggaggcagcccatgtttctccaccctcatatcactcaccagtttgta
atagtatctttgaatgacgatctgattaaggtccgtctctccattagtccacaagtttcgggggtac
atctactttgctcatttccatatcccagagtctagcacaaggcctggtacatagtagtgtcaata
aatatgttagatgtgaaaggaagataacacctctatgtactagcagtgagactccaggcatgcaatttct
ctctgtccttcagtccccttcatctccaagtttaatttaaatatggtaacgcctgtatgcaactcccag
catccagtaggcactcactaaacacagttctccaccctccttttttctctgccctcggttt
cccactactcctgcatgtgacacacacatagtttggagccataaaaccaaccccagttggactct
cacctctccagccccttctgctccggccctgtcctcaaattgggggggctgatgtcccatacacctgg
ctctgggttcccctaaccagagtgcaggactgcaggacccgcagtcccagccgcgggttcctaagcatgtcaggtctgccaggtcgc
cattgccatggagacagcagacaacagtccccagccgcgggttcctaagcatatgGTTACTCTTTAAcgta
tccaccacctgggtgattagaagaatcaatagatagacgggcgtgcagctgccgcactcacc
gccttcctgtgacggggctcctgtgctgtgctgtgagcgggccctgctcctccatgcc
ccagctctccggctCGAG [HNF4A P2 Dup1xH1RE: Sequence shown in Fig. 9A modified by
inserting a 20-bp fragment containing a putative H1RE located ~8.41 kb upstream from
NM_175194 between the KpnI & SacI sites with the forward PCR primer. The downstream
reverse primer introduced an NdeI site immediately upstream of the proximal H1RE.]

AAATTTGGTACCTGGCTAATTTTTAACATTTGAGCTCAAGCAGGTGGTGAGATCC [Forward
primer: P2/N/KpnI/SacI/F to introduce upstream H1RE.]

CGGCCAGCTGCCACCGCCCGGTTATCTTATTGATTCTTCTAATCACCCAAGGTGGGTGGATACGTTAA
AGAGTAACCATATGCTTAGGGAACCCGCGGCTG [Reverse primer: P2/N/PvuII/NdeI/R
(incorporated NdeI site adjacent to H1RE: used PvuII site to ligate.)]

*FIG. 9B*

GGTACCTGGCTAATTTTTAACATTTTGAGCTGGTTAATATTCACCACTACGCGTAGAGTTAATATTTA
ATATAGCGCGCTGGGTTAGTAATTACTATGTACAaagcaggtggtgagatccaaaactgagacaaaag
aaacgggctgttccaaaaaaaagctagtggcagttgtctaacatgccaggagctaaaacagagt
gtgtgagtttcagcagcaggttgaatttagaatggggaaggagaccagaggagacgccagacaggatg
actttgtccattggcctggaggcagcccccatgttttctccaccccatagtccatcactccagtttgtaa
tagtatctttgaatgacgatctgattaaggtccgtcctcctccattagtccacaagtttcggggtaca
tcactttgctcattccatatcccagagtctagcacaaggcctggtacatagtaggtgctcaataa
atatgttagatgaaaggagataacacctctatgtactagcagtgagactccaggcatgcaatttctc
tctgtcctcagtcccttcactctcaaggtttaatttaaatatgttaaaggccatgtgcaactcccagc
atccagtaggcactcactaaacacagttctccaccctccttttttcctctgccctccccaacccaggttggactctc
ccactacttcctgcatgtgacacaccccatagtttggagccataaaaaccaaccaggttgtcccatacacctgcc
acctctccagccccctaaccccagagtgcaggactaggaacccgagtggacctcaggtctggccaggtcgc
tctgggttccctaaccagacagcaaccagtccccAGCGCTAGCacaGCTAGCTGAGTTAATATTTAATAAGATAACGGTTACACATAGAGTATACTATA
CCTAGGATGGTTAATATTCACCaACGCTACGCGTGAgtactctt
taacgtatccacccacttgggtgattaagaagaatcaataagataacggaccggcggtggcagcgtgccgc
actcaccgccttcctggtggaccaggtggtgagatccgggtgtgctgctgctgctggtgtgagcggggccccctgctcct
ccatgccccagctctccggctCGAG [HNF4A P2 Dup4xH1RE (0.84 kb spacing): Sequence
shown in Fig. 9B modified by inserting a 3xH1RE segment adjacent to each H1RE with the
primers below. H1REs are highlighted and the CCAnnnnnnTGG PflMl site is underlined.]

TTTAAAGAGCTCGGTTAATATTCACCACTACGCGTAGAGTTAATATTTAATAATAGCGCGCTGGGTTAGTA
ATTACTATGTACAAAGCAGGTGGTGAGATCC [Forward primer P2/3xH1/SacI/MluI/BssHII/BsrGI/F
(H1REs from human α1-antitrypsin, β-fibrinogen. albumin downstream of distal H1RE)]

TTTAAACATATGTATACTATTAAATATTAACTCAGCTAGCTGTGGTGAATATTAACCATCCTAGGTATAGTAA
TTACTAACCCGTACGCTTAGGGAACCCGGGCTG [Reverse primer P2/3xH1/NdeI/AvrII/NheI/BsiWI/R
(H1REs from human albumin, α1-antitrypsin, β-fibrinogen upstream of proximal H1RE)]

FIG. 9C

GGTACCTGGCTAATTTTTAACATTTTGAGCTCGTTAATATTCACCACTACGCGTAGAGTTAATATATTTA
ATATAGCGCGCTGGGTTAGTAATTACTATGTACAgtttggagccataaaacccaaccccaggttggact
ctcacctctccagccccttctgctccggcccctgtcctcaaattgggggctgatgtcccatacacct
ggctctgggttccctaagcagtgcaggacccgagtggacctcaggtctgccaggtc
gccattgccatggagacagcaacagtccccCAGCCGCGGGTTCCCTAAGCGTACGGTTAGTAATTACT
ATACCTAGGATGGTTAATATTCACCACCAGCTAGCTGAGTTAATATTTAATAAGTATACATATGgttact
ctttaacgtatccaccaccttgggtgattagaagaatcaataagataaccgggcggtggcagctggc
cgcactcaccgcttcctggtggacgggctcctgttgctgctgtgagcgggccctgct
cctccatgcccccagctctccggctCGAG [HNF4A P2 Dup4xH1RE (0.23 kb spacing):
Sequence shown in Fig. 9B modified by deleting the DNA between the TGTACA BsrGI site
and the PflMI site (junction underlined).]

FIG. 9D

SEQUENCE LISTING

<160> NUMBER OF SEQ ID NOS: 35

<210> SEQ ID NO 1
<211> LENGTH: 700
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gagctcagta tcctcaacac agaagtctga agtgctaaga caacaggggt ttttccccc      60 ctgggaagtc tgatgttggg ctaggactga gggtgcagtg acccactcca ggaaatgtga    120
cctgattctg ccctggagaa ccggcccagt ggcccagagc ttcctgctgt cccagcggcc    180
caaagaaaca ggcttttaaa gttctcctgt gccaggctga aagcatcctg gagagtggga    240
cccagcgccg cacccagagg cctcctggct cctgctgcct ctagccctgc gcccctggcc    300
cctctccacc tcccccaccc tcccttctgc tcactcccaa ttgcaggcca tgactcccgg    360
tcccggtccc tctcacccgc catgaggcct gcacttgcaa ggctgaagtc caaagttcag    420
tcccttcgct aagcgcacgg ataaatatga accttggaga atttccccag ctccaatgta    480
aacagagcag gcaggggccc tgattcactg gccgctgggg ccagggttgg gggctggggg    540
tgcccacaga gcttgactag tgggatttgg gggggcagtg ggtgcagcga gcccggtccg    600
ttgactgcca gcctgccggc aggtagacac cggccgtggg tgggggaggc ggctagctca    660
gtggccttgg gccgcgtggc ctggtggcag cggagccatg                          700
```

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

```
taagcatgcc aaagttaatc atatgacaag tccaaaggtt aggagcgctg agtccaaaga     60
tcaggtcgac                                                            70
```

<210> SEQ ID NO 3
<211> LENGTH: 70
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 3

```
ttagtcgacc tgatctttgg actcagcgct cctaaccttt ggacttgtca tatgattaac      60
tttggcatgc                                                             70
```

<210> SEQ ID NO 4
<211> LENGTH: 473
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
tcccctctcc acctccccca ccctcccttc tgctcactcc caattgcagg ccatgactcc      60
cggtcccggt ccctctcacc cgccatgagg cctgcacttg caaggctgaa gtccaaagtt    120
cagtcccttc gctaagcatg ccaaagttaa tcatatgaca agtccaaagg ttaggagcgc    180
tgagtccaaa gatcaggtcg actaagcgca cggataaata tgaaccttgg agaatttccc    240
cagctccaat gtaaacagag caggcagggg ccctgattca ctggccgctg gggccagggt    300
tgggggctgg gggtgcccac agagcttgac tagtgggatt tggggggggca gtgggtgcag    360
cgagcccggt ccgttgactg ccagcctgcc ggcaggtaga caccggccgt gggtggggga    420
ggcggctagc tcagtggcct tgggccgcgt ggcctggtgg cagcggagcc atg           473
```

<210> SEQ ID NO 5
<211> LENGTH: 812
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
tcccctctcc acctccccca ccctcccttc tgctcactcc caattgcagg ccatgactcc      60
cggtcccggt ccctctcacc cgccatgagg cctgcacttg caaggctgaa gtccaaagtt    120
cagtcccttc gctaagcatg ccaaagttaa tcatatgaca agtccaaagg ttaggagcgc    180
tgagtccaaa gatcaggtcg actaagcgca cggataaata tgaaccttgg agaatttccc    240
cagctccaat gtaaacagag caggcagggg ccctgattca ctggccgctg gggccagggt    300
tgggggctgg gggtgcccac agagcttgac tagtgggatt tggggggggca gtgggtgcag    360
cgagcccggt ccgttgactg ccagcctgcc ggcaggtaga caccggccgt gggtggggga    420
ggcggctagc ctgcacttgc aaggctgaag tccaaagttc agtcccttcg ctaagcatgc    480
caaagttaat catatgacaa gtccaaaggt taggagcgct gagtccaaag atcaggtcga    540
ctaagcgcac ggataaatat gaaccttgga gaatttcccc agctccaatg taaacagagc    600
aggcaggggc cctgattcac tggccgctgg ggccagggtt gggggctggg ggtgcccaca    660
gagcttgact agtgggattt ggggggggcag tgggtgcagc gagcccggtc cgttgactgc    720
cagcctgccg gcaggtagac accggccgtg ggtgggggag gcggctagct cagtggcctt    780
gggccgcgtg gcctggtggc agcggagcca tg                                   812
```

<210> SEQ ID NO 6

<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gcccctctcc acctccccca ccctcccttc tgctcactcc caattgcagg ccatgactcc    60
cggtcccggt ccctctcacc cgccatgagg cctgcacttg caaggctgaa gtccaaagtt   120
cagtcccttc gctaagcgca cggataaat                                      149

<210> SEQ ID NO 7
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gcccctctcc acctccccca ccctcccttc tgctcactcc caattgcagg ccatgactcc    60
cggtcccggt ccctctcacc cgccatgagg cctgttaggt aaaggctgaa gtccaaagtt   120
cagtcccttc gctaagcgca cggataaat                                      149

<210> SEQ ID NO 8
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ggtaccggga ggggcaaagg cctcgggctc tgagcggcct tggcccttct ccaccaaccc    60
ctgccctaca ctaaggggga ggcagcgggg ggcacacagg gtggggcgg gtggggggct   120 gctgggtgag cagcactcgc ctgcctggat tgaaacccag agatggaggt gctgggaggg   180
gctgtgagag ctcagccctg taaccaggcc ttgccggagc cactgatgcc tggtcttctg   240
tgcctttact ccaaacaccc cccagcccaa gccacccact tgttctcaag tctgaagaag   300
cccctcaccc ctctactcca ggctgtgttc agggcttggg gctggtggag ggagggggcct   360 gaaattccag tgtgaaaggc tgagatgggc ccgaggcccc tggcctatgt ccaagccatt   420
tcccctctca ccagcctctc cctggggagc cagtcagcta ggaaggaatg agggctcccc   480
aggcccaccc ccagttcctg agctcatctg ggctgcaggg ctggcgggac agcagcgtgg   540
actcagtctc ctagggattt cccaactctc ccgcccgctt gctgcatctg dacaccctgc   600
ctcaggccct catctccact ggtcgctagc tgggcaaagg tcagcgccct gggtcctcag   660
tgcctgctgc cctggagatg atataaaaca ggtcagaacc ctcctagatc t             711

<210> SEQ ID NO 9
<211> LENGTH: 844
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ggtaccaagc agtccaaaga tcatgaattc acaatgccaa agttaacgta cggctgagtc    60

```
caaagttcag gtcgagggag gggcaaaggc ctcgggctct gagcggcctt ggcccttctc      120
caccaacccc tgccctacac taaggggag gcagcggggg gcacacaggg tggggcggg       180 tgggggctg  ctgggtgagc agcactcgcc tgcctggatt gaaacccaga gatggaggtg      240
ctgggagggg ctgtgagagc tcagccctgt aaccaggcct gccggagcc  actgatgcct     300 ggtcttctgt gcctttactc caaacacccc ccagcccaag ccacccactt gttctcaagt     360
ctgaagaagc ccctcacccc tctactccag gctgtgttca gggcttgggg ctggtggagg     420
gaggggcctg aaattccagt gtgaaaggct gagatgggcc cgaggcccct ggcctatgtc     480
caagccattt cccctctcac cagcctctcc ctggggagcc agtcagctag aaggaatga      540 gggctcccca ggcccacccc cagttcctga gctcatctgg gctgcagggc tggcgggaca     600
gcagcgtgga ctcagtctcc tagggattc  ccaactctcc cgcccgcttg ctgcatctgg     660
acaccctgcc tcaggccctc atctccactg gtcatgccaa agttaatact agtacaagtc     720
caaagttcag gcatatgtga gtccaaagat cagtcgacgc tagctgggca aaggtcagcg     780
ccctgggtcc tcagtgcctg ctgccctgga gatgatataa aacaggtcag aaccctccta     840
gatc                                                                 844

<210> SEQ ID NO 10
<211> LENGTH: 99
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaatttggta ccaagcagtc caaagatcat gaattcacaa tgccaaagtt aacgtacggc       60
tgagtccaaa gttcaggtcg agggaggggc aaaggcctc                              99

<210> SEQ ID NO 11
<211> LENGTH: 97
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaatttgcta gcgtcgactg atctttggac tcacatatgc ctgaactttg gacttgtact       60
agtattaact ttggcatgac cagtggagat gagggcc                               97

<210> SEQ ID NO 12
<211> LENGTH: 533
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ggtaccaagc agtccaaaga tcatgaattc acaatgccaa agttaacgta cggctgagtc       60
caaagttcag gtcgagggag gggcaaaggc ctcgggctct gagcggcctt ggcccttctc      120
caccaacccc tgccctacac taaggggag  gcagcggggg gcacacaggg tggggcggg      180 tgggggctg  ctgggtgagc agcactcgcc tgcctggatt gaaacccaga gatggaggtg      240
ctgggagggg ctgtgagagc tcatctgggc tgcagggctg gcgggacagc agcgtggact     300
```

```
cagtctccta gggatttccc aactctcccg cccgcttgct gcatctggac accctgcctc    360
aggccctcat ctccactggt catgccaaag ttaatactag tacaagtcca aagttcaggc    420
atatgtgagt ccaaagatca gtcgacgcta gctgggcaaa ggtcagcgcc ctgggtcctc    480
agtgcctgct gccctggaga tgatataaaa caggtcagaa ccctcctaga tct           533
```

<210> SEQ ID NO 13
<211> LENGTH: 1019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
ggtaccgagc tcccccaagca ggtggtgaga tccaaaactg agacaaaaga acgggggctg    60
ttccaaaaaa aaagctaggt ggcaggtgtc taacatgcca gggagctaaa acagagtgtg   120
tgagtttcag cagcaggttg aatttagaat ggggaaggag accagaggag acgccagaca   180
ggatgacttt gtcccattgg cctggaggca gccccatgtt tctccacccc tcatatcact   240
caccagtttg taatagtatc tttgaatgac gatctgatta aggtccgtct cctccattag   300
tccacaagtt tcgggggtac atctactttg ctcatttcca tatccccaga gtctagcaca   360
aggcctggta catagtaggt gctcaataaa tatgttagat gaaaggaaga taacacctct   420
atgtactagc agtgagactc caggcatgca atttctctct gtccttcagt cccttcatct   480
caaggtttaa tttaaatatg gtaacgcctg tatgcaactc ccagcatcca gtaggcactc   540
actaaacaca gttctccacc ctcctttttt cctctgcccc tccctcggtt ttcccactac   600
ttcctgcatg gtgacacacc catagtttgg agccataaaa cccaacccag gttggactct   660
cacctctcca gccccttctg ctccggccct gtcctcaaat tgggggggctg atgtccccat   720 acacctggct ctgggttccc ctaaccccag agtgcaggac taggacccga gtggacctca   780
ggtctggcca ggtcgccatt gccatggaga cagcaacagt ccccagccgc gggttcccta   840
agtgactggt tactctttaa cgtatccacc caccttgggg gattagaaga atcaataaga   900
taaccgggcg gtggcagctg gccgcactca ccgccttcct ggtggacggg ctcctggtgg   960
ctgtgctgct gctgtgagcg ggcccctgct cctccatgcc cccagctctc cggctcgag   1019
```

<210> SEQ ID NO 14
<211> LENGTH: 1039
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
ggtacctggc taattttaa cattttgagc tcccccaagca ggtggtgaga tccaaaactg     60
agacaaaaga acgggggctg ttccaaaaaa aaagctaggt ggcaggtgtc taacatgcca   120
gggagctaaa acagagtgtg tgagtttcag cagcaggttg aatttagaat ggggaaggag   180
accagaggag acgccagaca ggatgacttt gtcccattgg cctggaggca gccccatgtt   240
tctccacccc tcatatcact caccagtttg taatagtatc tttgaatgac gatctgatta   300
aggtccgtct cctccattag tccacaagtt tcgggggtac atctactttg ctcatttcca   360
tatccccaga gtctagcaca aggcctggta catagtaggt gctcaataaa tatgttagat   420
```

```
gaaaggaaga taacacctct atgtactagc agtgagactc caggcatgca atttctctct    480
gtccttcagt cccttcatct caaggtttaa tttaaatatg gtaacgcctg tatgcaactc    540
ccagcatcca gtaggcactc actaaacaca gttctccacc ctccttttt  cctctgcccc    600 tccctcggtt ttcccactac ttcctgcatg gtgacacacc catagtttgg agccataaaa    660
cccaacccag gttggactct cacctctcca gcccttctg ctccggccct gtcctcaaat     720
tggggggctg atgtccccat acacctggct ctgggttccc ctaacccag  agtgcaggac    780 taggacccga gtggacctca ggtctggcca ggtcgccatt gccatggaga cagcaacagt    840
ccccagccgc gggttcccta agcatatggt tactctttaa cgtatccacc cacccttggg t    900 gattagaaga atcaataaga taaccgggcg gtggcagctg gccgcactca ccgccttcct    960
ggtggacggg ctcctggtgg ctgtgctgct gctgtgagcg ggcccctgct cctccatgcc   1020
cccagctctc cggctcgag                                               1039
```

<210> SEQ ID NO 15
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
aaatttggta cctggctaat ttttaacatt ttgagctcaa gcaggtggtg agatcc        56
```

<210> SEQ ID NO 16
<211> LENGTH: 101
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
cggccagctg ccaccgcccg gttatcttat tgattcttct aatcacccaa ggtgggtgga    60
tacgttaaag agtaaccata tgcttaggga acccgcggct g                        101
```

<210> SEQ ID NO 17
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
ggtacctggc taatttttaa catttgagc tcgttaatat tcaccactac gcgtagagtt     60
aatatttaat atagcgcgct gggttagtaa ttactatgta caaagcaggt ggtgagatcc    120
aaaactgaga caaagaaac  ggggctgttc caaaaaaaaa gctaggtggc aggtgtctaa    180
catgccaggg agctaaaaca gagtgtgtga gtttcagcag caggttgaat ttagaatggg    240
gaaggagacc agaggagacg ccagacagga tgactttgtc ccattggcct ggaggcagcc    300
ccatgtttct ccaccctca  tatcactcac cagtttgtaa tagtatcttt gaatgacgat    360
ctgattaagg tccgtctcct ccattagtcc acaagtttcg ggggtacatc tactttgctc    420
atttccatat ccccagagtc tagcacaagg cctggtacat agtaggtgct caataaatat    480
gttagatgaa aggaagataa cacctctatg tactagcagt gagactccag gcatgcaatt    540
```

```
tctctctgtc cttcagtccc ttcatctcaa gtttaattt aaatatggta acgcctgtat    600
gcaactccca gcatccagta ggcactcact aaacacagtt ctccaccctc cttttttcct    660
ctgcccctcc ctcggttttc ccactacttc ctgcatggtg acacacccat agtttggagc    720
cataaaaccc aacccaggtt ggactctcac ctctccagcc ccttctgctc cggccctgtc    780
ctcaaattgg ggggctgatg tccccataca cctggctctg ggttcccta accccagagt    840 gcaggactag gacccgagtg gacctcaggt ctggccaggt cgccattgcc atggagacag    900
caacagtccc cagccgcggg ttccctaagc gtacgggtta gtaattacta tacctaggat    960
ggttaatatt caccacagct agctgagtta atatttaata gtatacatat ggttactctt   1020
taacgtatcc acccaccttg ggtgattaga agaatcaata agataaccgg gcggtggcag   1080
ctggccgcac tcaccgcctt cctggtggac gggctcctgg tggctgtgct gctgctgtga   1140
gcgggcccct gctcctccat gccccagct ctccggctcg ag                       1182
```

```
<210> SEQ ID NO 18
<211> LENGTH: 101
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttaaagagc tcggttaata ttcaccacta cgcgtagagt taatatttaa tatagcgcgc    60
tgggttagta attactatgt acaaagcagg tggtgagatc c                       101

<210> SEQ ID NO 19
<211> LENGTH: 107
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tttaaacata tgtatactat taaatattaa ctcagctagc tgtggtgaat attaaccatc    60
ctaggtatag taattactaa cccgtacgct tagggaaccc gcggctg                 107

<210> SEQ ID NO 20
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
ggtacctggc taattttaa cattttgagc tcgttaatat tcaccactac gcgtagagtt    60
aatatttaat atagcgcgct gggttagtaa ttactatgta cagtttggag ccataaaacc   120
caacccaggt tggactctca cctctccagc cccttctgct ccggccctgt cctcaaattg   180
gggggctgat gtccccatac acctggctct gggttcccct aaccccagag tgcaggacta   240
ggacccgagt ggacctcagg tctggccagg tcgccattgc catggagaca gcaacagtcc   300
ccagccgcgg gttccctaag cgtacgggtt agtaattact atacctagga tggttaatat   360
tcaccacagc tagctgagtt aatatttaat agtatacata tggttactct ttaacgtatc   420
cacccacctt gggtgattag aagaatcaat aagataaccg gcggtggca gctggccgca   480
```

```
ctcaccgcct tcctggtgga cgggctcctg gtggctgtgc tgctgctgtg agcgggcccc    540
tgctcctcca tgccccagc tctccggctc gag                                  573
```

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: a, c, t, g, unknown or other

<400> SEQUENCE: 21

```
agaacannnt gttct                                                     15
```

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
ggtcactgtg acc                                                       13
```

<210> SEQ ID NO 23
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
ggacactgtg tcc                                                       13
```

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
gagcctggta ccgggagggg caaaggcc                                       28
```

<210> SEQ ID NO 25
<211> LENGTH: 110
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
aaatttagat ctaggagggt tctgacctgt tttatatcat ctccagggca gcaggcactg    60
aggacccagg gcgctgacct tgcccagct agcgaccagt ggagatgagg              110
```

<210> SEQ ID NO 26
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 26

Tyr Pro Tyr Asp Val Pro Asp Tyr Ala
1               5

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Pro Tyr Asp Val Pro Asp Tyr Ala Gly Gly Tyr Pro Tyr Asp Val
1               5                   10                  15

Pro Asp Tyr Ala
            20

<210> SEQ ID NO 28
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttaatctaga ttaagcatag tccgggacgt catagggata tccgcccgca tagtcaggaa      60
catcgtatgg gtaagcaact tgcccaaagc                                       90

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Pro Tyr Asp Val Pro Asp Tyr Ala
1               5

<210> SEQ ID NO 30
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gctttgggca agttgcttac ccatacgatg ttcctgacta tgcgggcgga tatccctatg      60
acgtcccgga ctatgcttaa tctagattaa                                       90

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 31
gtttaaactt aagctt                                                          16

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aagcttggcg gtagaggagc catgg                                                25

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccatgaaact taagcttggc ggtagaggag ccatgg                                    36

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccatgaaact taagcttggc ggtagaggag ccatgg                                    36

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 35
ccannnnntg g                                                               11
```

ENHANCED ENGINEERED NATIVE PROMOTERS AND USES THEREOF

CROSS REFERENCE TO RELATED APPLICATIONS

This application is a 35 U.S.C. §371 National Phase Entry Application of International Application No. PCT/US2010/037551 filed Jun. 5, 2010, which designates the U.S., and which claims benefit under 35 U.S.C. §119(e) of the U.S. provisional application No. 61/184,475 filed Jun. 5, 2009, the contents of which are incorporated herein by reference in their entireties.

BACKGROUND OF INVENTION

Expressing genes of interest in cells or tissues for therapeutic purposes often entails driving transcription with strong viral or constitutive promoters. However, such methods can lead to some undesired consequences. For example, tumorigenic transformation can occur in the transfected target cells from unregulated expression of potentially oncogenic cell conversion factors (1) or insertional mutagenesis by retroviral vectors (2, 3).

One solution is to incorporate some synthetic regulatory elements into the therapeutic constructs and this method has confers some control (4). However, this method also increases the system complexity and may require pharmaceutical agents to modulate promoter activity.

Another method is to assimilate appropriate regulatory elements to retain innate responsiveness of the engineered genes. Since transcription is a fundamental mechanism for controlling gene expression, incorporating naturally occurring regulatory elements can be useful in increasing fidelity and safety of engineered genes. For most eukaryotic genes, the majority of the information necessary for recapitulating developmental and spatial expression resides in the proximal promoter which can be a few hundred base-pairs (bp) long. However, endogenous transcriptional activity is difficult to achieve in engineered vectors with promoter fragments lacking their genomic context and distal elements. For instance, expression of genes linked to the β-globin promoter can achieve levels comparable to the endogenous promotor but requires inclusion of the β-globin locus control region, an extended enhancer located at an ectopic chromatin site (7, 8). Other promoters rely on similar compact distal enhancers (9) but locus control regions are unique and gene specific.

Several other strategies have been employed to enhance transcriptional activities of native promoters while retaining (or engineering) innate regulation: use of larger promoters (10), duplicating positive response elements (RE) (11) or more complex promoter fragments (12,13), fusing distal (14) or ectopic enhancers (15), and binary amplification systems (16). Appropriate targeting and responsiveness is theoretically possible by combining cis elements into "designer promoters" (17). For single response elements, highly inducible promoters have been constructed from a minimal TATA box by fusing multiple binding sites for hypoxia-inducible factor (HIF) binding sites with optimal spacing of orientation to achieve hypoxia responsiveness (18) or 7 T-cell factor/lymphoid enhancer-binding factor (TCF/LEF) binding sites to achieve a β-catenin responsiveness (19).

However, attempts to achieve endogenous transcriptional activities from native mammalian promoters have not been as successful. New or significantly improved approaches are necessary to make native or synthetic promoters widely useful for genetic engineering in humans and other mammals.

SUMMARY OF THE INVENTION

The disclosure relates to methods and DNA constructs for engineered promoters for enhancing gene expression.

The invention is based on the surprising finding that one can significantly enhance native promoter function by arranging several transcription factor response elements in tandem with a specific spacing between them to form segments of transcription factor elements. Moreover, the transcription can be further enhanced by including at least two of such segments in the promoter region of the gene. Use of the presently described engineered promoters allows one to avoid using viral promoters and yet results in enhanced expression of the genes thus providing a significant improvement for any mammalian gene expression system either in vivo or in vitro.

Specifically, in one embodiment, the present disclosure provides an engineered DNA construct for increasing gene expression from a transcription factor (TF) dependent promoter comprising at least one transcription factor response element (TFRE) segment, wherein the segment comprises between four and 16 consecutive TFREs, wherein each of the TFRE is separated by about 9 to 15 base-pairs (bp), and wherein all of the TFREs are response elements (REs) for one transcription factor (TF).

In one embodiment, the disclosure herein provides a modified promoter comprising at least one transcription factor response element (TFER) segment, wherein the TFRE segment comprises 4-16 TFREs, wherein all of the TFREs are response elements (REs) of one transcription factor (TF) native to a promoter, wherein each of the 4-16 TFREs are separated by 9-15 base pairs (bp).

In one embodiment, provided herein is a method of enhancing expression of a gene comprising operably linking the gene to an engineered promoter forming a gene expression construct, wherein the engineered promoter comprises at least one transcription factor response element (TFER) segment, wherein the TFRE segment comprises four to 16 TFREs; wherein all of the TFREs are response elements (REs) of one transcription factor (TF), and wherein each of the TFRE is in forward orientation, and wherein each of the four to 16 TFREs are separated by 9-15 base pairs, and wherein the at least one TFER segment is inserted upstream (5') of the ATG start codon of the gene.

In one embodiment, provided herein is a method for enhancing gene expression from a transcription factor (TF) dependent promoter comprising: (a) engineering a DNA construct comprising a transcription factor response element (TFRE) segment comprising between four and 16 consecutive TFRE sequences in a forward orientation, wherein each of the TFRE is separated by 9-15 base-pairs (bp), and wherein all of the TFREs are response elements (REs) of one transcription factor (TF); (b) operably linking the engineered DNA construct upstream (5') of an ATG start codon of a gene regulated by the TF dependent promoter that is operably linked to the gene to make a gene expression construct; and (c) transducing a host cell with the gene expression construct.

In one embodiment, the disclosure herein provides a method for enhancing gene expression from a transcription factor (TF) dependent promoter comprising: (a) engineering a first DNA construct comprising a transcription factor response element (TFRE) segment comprising between four and 16 consecutive TFRE sequences in a forward orientation, wherein each of the TFRE is separated by 9-15 base-pairs (bp), and wherein all of the TFREs are response elements (REs) of one transcription factor (TF); (b) engineering a second DNA construct to further comprise at least two TFRE segments of step (a), wherein the TFRE segments are separated by 200-700 base pairs; (c) operably linking the engineered second DNA construct upstream (5') of an ATG start codon of a gene regulated by the TF dependent promoter that is operably linked to the gene to make a gene expression construct; and (d) transducing a host cell with the gene expression construct.

In one embodiment, provided herein is a method for modifying a promoter to enhance gene expression from a transcription factor dependent promoter comprising: (a) identifying a native transcription factor response element (TFRE) in a DNA sequence comprising the promoter that is located upstream (5') of an ATG start codon of a gene that is operably linked to the transcription factor dependent promoter; (b) engineering a DNA construct comprising a transcription factor response element (TFRE) segment comprising between four and 16 consecutive native transcription factor RE sequences, wherein each of the TFREs are separated by 9-15 base-pairs (bp); and wherein all of the TFREs are response elements (REs) of a transcription factor (TF) that binds the native TFRE; and (c) operably linking the engineered second DNA construct upstream (5') of the ATG start codon of the gene regulated by transcription factor dependent promoter that is operably linked to the gene to make a gene expression construct.

In one embodiment, provided herein is a method for modifying a promoter to enhance gene expression from a transcription factor dependent promoter comprising: (a) identifying a native transcription factor response element (TFRE) in a DNA sequence comprising the promoter that is located upstream (5') of an ATG start codon of a gene that is operably linked to the transcription factor dependent promoter; (b) engineering a first DNA construct comprising a transcription factor response element (TFRE) segment comprising between four and 16 consecutive native transcription factor RE sequences, wherein each of the TFREs are separated by 9-15 base-pairs (bp); and wherein all of the TFREs are response elements (REs) of a transcription factor (TF) that binds the native TFRE; (c) engineering a second DNA construct to further comprise at least two TFRE segments, wherein the TFRE segments are separated by 200-700 base pairs; and (d) operably linking the engineered second DNA construct upstream (5') of the ATG start codon of the gene regulated by transcription factor dependent promoter that is operably linked to the gene to make a gene expression construct.

In some embodiments, the promoters can be mammalian or non-mammalian promoters. Examples of human promoters are the human U6, H1 and tRNA promoters. In other embodiments, the promoters can be a synthetically made promoter made of parts from many non-related sources, much like a chimeric promoter.

In some embodiments, the TFREs are in forward configuration, forward direction or forward orientation. In some embodiments, the TFREs are in reverse configuration, reverse direction or reverse orientation. In other embodiments, the TFREs in a segment have a mixed forward and reverse orientation.

In some embodiments, the genes do no express proteins but rather express RNA that are utilized by the cell, e. g. for pre-microRNA, ribosomal and transfer RNA.

In some embodiments, the engineered DNA construct, modified promoter or engineered promoter described herein is a gene expression construct.

In one embodiment of the methods, engineered DNA construct, modified promoter or engineered promoter described herein, the gene expression construct is further transduced into a host cell.

In one embodiment, the host cell is selected from a group consisting of hepatocytes, pancreatic beta cells, intestinal mucosal cells, intestinal mucosal cells, renal proximal tubule cells, hematopoietic cells, epidermal cells, endothelial cell, pre-myocytes, myocytes, and muscle cells. In some embodiments, the host cells can be a stem cell. For example, adult stem cells, embryonic stem cells, induced pluripotent stem cells, etc. In other embodiments, the host cells can be any cell within the body of an organism, e.g. when a gene therapy vector or construct is used. In other embodiments, the host cells can be the type of cells used for the bioprocess production of commercial therapeutic biologics, e. g. therapeutic antibodies, proteins and peptides. For example, Chinese hamster ovary (CHO) cells and mouse myeloma cells. In other embodiments, the host cell is a cell selected from Tables 1-4.

In one embodiment, the expression of the gene is in vivo.
In one embodiment, the expression of the gene is in vitro.
In one embodiment, the engineered DNA construct described herein is operably linked upstream (5') of an ATG start codon of a gene that is operably linked to a TF dependent promoter.

In one embodiment, the engineered DNA construct, modified promoter or engineered promoter described herein comprises at least two TFRE segments, wherein the two TFRE segments are separated by 200-700 bp.

In one embodiment, at least one TFRE of the TFRE segment is the native to the promoter of the gene In one embodiment, the engineered promoter or modified promoter is derived from a native promoter of the gene. In one embodiment, the gene is a mammalian gene.

In one embodiment, the mammalian promoter is selected from a group consisting human, mouse, rat, non-human primate (e.g. monkey, baboon, ape, and chimpanzee), dog, and hamster. In one embodiment, the mammalian promoter is a non-human promoter, e. g. mouse, rat, non-human primate (e. g. monkey, baboon, ape, and chimpanzee), dog, and hamster. In one embodiment, the mammalian promoter is a human promoter.

In one embodiment of the methods, the engineered DNA construct, modified promoter or engineered promoter described herein, the TFRE is for a TF selected from a group of consisting of homeo-domain type, nuclear hormone receptor type, basic helix-loop-helix (bHLH), basic-leucine zipper type (bZIP), winged helix type, zinc binding type, and heat-shock type TFs.

In one embodiment, the TF is a homeo-domain type TF. In one embodiment, the homeo-domain type TF is a hepatocyte nuclear factor 1 alpha (HNF1A) or (HNF1α) TF.

In one embodiment, the TF is a nuclear hormone receptor type TF. In one embodiment, the nuclear hormone receptor type TF is a hepatocyte nuclear factor 4 alpha (HNF4A) or (HNF4α).

In one embodiment, provided herein is a vector comprising an engineered DNA construct, engineered promoter or modified promoter construct described herein. In one embodiment, the vector is a gene therapy vector or a vector adapted for gene therapy.

In one embodiment, provided herein is a cell comprising a vector of any one embodiments of the engineered DNA construct, engineered promoter or modified promoter construct described herein.

DEFINITIONS

As used herein, the term "native" as in "native promoter" refers to a promoter that is naturally and/or originally present in a cell and it is typically designated for the expression of a particular gene. In one embodiment, "native promoter" is encoded in the natural original genome of the cell. In one embodiment, no extra ordinary measures have been taken by another organism to insert the promoter artificially into the cell. A non-native promoter would be a promoter is not originally present in a cell and it has been inserted artificially into the cell. In one embodiment, a non-native promoter of a gene is one that that is not naturally associated with the gene. For example, the mouse hepatocyte nuclear factor 1α Dup4× H4RE (Hnf1α$^{Dup4 \times H4RE}$) promoter was operably linked with a human hepatocyte nuclear factor 1 alpha (HNF1 alpha) cDNA. The Hnf1α$^{Dup4 \times H4RE}$ is a non-native promoter.

As used herein, "the native response element (RE)" or the "native promoter (RE)" refers to the RE that is naturally present in the promoter DNA sequence. For example, the human apolipoprotein C3 (ApoC3) gene is expressed from a HNF4 alpha (HNF4A) transcription factor dependent ApoC3 promoter which has two REs for HNF4A. The two REs for HNF4A (H4RE) are the native RE of the ApoC3 promoter Likewise, the hepatocyte nuclear factor 1 alpha (HNF1A) transcription factor dependent human HNF4A P2 promoter has one RE for HNF1alpha (H1RE). The H1RE in the native RE of the human HNF4A P2 promoter.

As used herein, the term "fragment" as in "promoter fragment" refers a part or portion of the promoter sequence that is in the genome.

As used herein, the term "forward direction", "forward orientation" or "forward configuration" with respect to a response element DNA sequence in a promoter refers to the orientation of the DNA sequence. It is typically the most common orientation of that family/class of RE with respect to the transcription start site on the sense strand of DNA of the gene or with respect to the direction of transcription of the associated gene. For example, the most common orientation and therefore the consensus binding site sequence for the TATA-binding protein (TBP) is TATAAAA. This is in forward direction. TTTTATA is the reverse or backward direction. Regardless of the orientation of the transcription factor response element (TFRE), transcription factors generally still bind to their respective TFRE and are able to activate and stimulate gene expression.

As used herein, the term "chimeric" with reference to the mini gene cassettes or promoters described herein refers to being composed of DNA sequences from different origins. For example, the Hnf1α$^{Dup4 \times H4RE}$/HNF4α3$^{HA}$ mini gene is composed of the HNF4α3 gene (cDNA) translationally fused a DNA sequence encoding the HA-tag at the C-terminus of HNF4α3. The promoter DNA sequence for transcribing the chimeric gene HNF4c6HA is composed of mouse Hnf1α promoter sequence and eight H4REs of different genes, e. g. from mouse Hnf1α, human G6Pase (located on Chromosome 17 at −236/−218 and −78/−60 from RefSeq: NM_000151) and human HNF1B (TCF2) genes (located on Chromosome 17 (Ch17)at −214/−196 from RefSeq: NM_000458; the negative numbering is with respect to the first nucleotide in the RefSeq and is to the left of that first nucleotide on the chromosome. The RefSeq provides the transcribed sequence from the gene and represents the putative transcriptional start site on the chromosome).

As used herein, the term "chimeric minigene cassette" with reference to the mini genes described herein refers to a expression gene being composed of DNA sequences from different origins, the DNA sequences each having different functions within the gene (e. g. transcriptional regulatory, ribosome binding, promoter sequences etc), and the chimeric minigene cassette has all the necessary sequences to expresse the gene within, and it expresses a single gene product, e. g. a protein. For the Hnf1α$^{Dup4 \times H4RE}$/HNF4α3$^{HA}$ minigene cassette, the HNF4α3$^{HA}$ protein is expressed. The different DNA sequences are operably linked to the gene.

As used herein, the term "upstream" is used in reference to a DNA sequence with respect to a specific site on a DNA sequence. It indicates that the DNA sequence to the left side of the specified site wherein the DNA sequence is oriented in a 5' to 3' direction. An example of a specific site of reference is the ATG start codon in a gene. Typically, the specific site is numbered as "one" and upstream location of the DNA sequence with respect to the specific site is numbered in the negative, e. g. −213 nt or by of the specific site. Another example of a specific site of reference is the transcription start site of the gene. Typically, the specific site is numbered as zero and upstream location of the DNA sequence with respect to the specific site is numbered in the negative, e. g. −213 nt or by of the transcription start site of the gene. For example, the RE of the human G6Pase gene is located on Chromosome 17 at −236/−218 and −78/−60 from RefSeq: NM_000151. The RefSeq provides the transcribed sequence from the gene and represents the putative transcriptional start site of the human G6Pase gene on the chromosome. This putative transcriptional start site is numbered as "one" or +1. Therefore, the RE of the human G6Pase gene is located −236/−218 and −78/−60 from this +1 start site on the chromosome.

As used herein, the term "nucleotide" is abbreviated "nt".

As used herein, the term "base-pair" is abbreviated "bp".

In the context of the engineered DNA constructs, engineered promoter and modified promoters wherein the transcription factor response element (TFRE) are separated by 9-15 bp, or when the TFRE segments are separated by 200-700 bp, it is understood that the engineered DNA constructs, engineered promoter and modified promoters comprise double DNA sequences and the nucleotides on one strand are base paired with those on the corresponding strand in the standard Watson and Crick base pairing. In the occasion when single-stranded DNA sequences are used, e. g. in PCR primers, one skilled in the art would recognize then that the TFRE would be separated by 9-15 nt or 200-700 nt.

As used herein the term "comprising" or "comprises" is used in reference to DNA sequence and methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to DNA sequence and methods, and respective components thereof as described herein, which are exclusive of any element not recited in that description of the embodiment.

The term "gene" or "coding sequence" means the nucleic acid sequence which is transcribed (DNA) and translated (mRNA) into a polypeptide in vitro or in vivo when operably linked to appropriate regulatory sequences, e. g. transcription factor response elements (TFRE). The gene may or may not include regions preceding and following the coding region, e.g. 5' untranslated (5'UTR) or "leader" sequences and 3' UTR or "trailer" sequences, as well as intervening sequences (introns) between individual coding segments (exons). In one embodiment, a gene refers to a complementary DNA (cDNA) that is derived from a messenger RNA (mRNA) of the gene.

As used herein, "identity" means the percentage of identical nucleotide at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., Oxford University Press, New York, 1988. Methods to determine identity are designed to give the largest match between the sequences tested. Moreover, methods to determine identity are codified in publicly available computer programs such as BLASTP.

The terms "identical" or percent "identity", in the context of two or more nucleic acid sequences, refers to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This term also refers to, or can be applied to, the complement of a DNA sequence or a messenger RNA (mRNA). The term also includes sequences that have deletions and/or additions, as well as those that have substitutions.

As used herein, the term "DNA sequence" refers to any nucleic acid molecule, preferably a polymeric molecule, incorporating units of deoxyribonucleic acid. The nucleic acid can be either single-stranded or double-stranded. "DNA sequence", "polynucleotide molecule" and "nucleic acid" are use interchangeably.

The term "operably linked" means generally that the regulatory elements and promoter in a DNA sequence or nucleic acid construct are in-frame with a nucleic acid coding sequence for a protein or peptide. Accordingly, the term typically refers to an arrangement wherein the first polynucleotide molecule is connected with the second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the phrase "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art.

As used herein, the term "promoter" refers to a polynucleotide molecule that in its native state (i. e. as is naturally in the genome of an organism) is located upstream or 5' to a translational start codon of an open reading frame (or protein-coding region) or the transcription start site and that is involved in the recognition and binding of RNA polymerase II and other proteins (trans-acting transcription factors) to initiate transcription. Generally, a promoter is used as a 5' regulatory element for modulating expression of a particular gene or genes operably associated or linked thereto. When operably linked to a transcribable polynucleotide molecule, a promoter typically causes the transcribable polynucleotide molecule to be transcribed in a manner that is similar to that of which the promoter is normally associated. A "core basic promoter" is one that will transcribe any transcribable polynucleotide molecule that is operably linked to it. Transcription takes place as long as the transcription machinery (ribosome etc) and raw materials for transcription (RNAs) are available. In one embodiment, the transcription for a "core basic promoter" is on all the time or constitutive. In some embodiments, the "core basic promoter" can comprise addition transcription factor (TF) response elements (TFRE) and/or enhancer elements (collectively known as regulatory elements) that allow the transcription of the transcribable polynucleotide molecule to be regulated. The regulation is by the presence or absence of transcription factors or enhancers binding to the elements comprising the promoter. For examples, transcription only occurs in the presence of the factor or transcription is further increased in the presence of the enhancer. Promoter databases and computer softwares are available for predicting the location of promoter sequences of genes in the genome of an organism, e. g. at Wormbase, the Cold Spring Harbor Laboratory, Molbio-Tools, Weizmann Institute of Science and Wellcome Trust Sanger Institute. One of ordinary skill in the art would be able to identify and/or locate promoter sequences of genes of interest using these and other methods/tools known in the art.

A transcription factor (TF) (sometimes called a sequence-specific DNA binding factor) is a protein that binds to specific DNA sequences and thereby controls the transfer (or transcription) of genetic information from DNA to mRNA. TFs perform this function alone or with other proteins in a complex, by promoting (as an activator), or blocking (as a repressor) the recruitment of RNA polymerase (the enzyme that performs the transcription of genetic information from DNA to RNA) to specific genes. The specific DNA sequences to which a TF binds is known as a response element (RE) or regulatory element. Other names include cis-element and cis-acting transcriptional regulatory element.

Transcription factors (TFs) are classified based on many aspects. For example, the secondary, tertiary and quaternary structures of the protein structures DNA-binding sequence and properties, the interaction with the double helix of the DNA, and the metal and other binding characteristics. TFs are grouped into superclasses which are then divided into classes which are further divided into families and subfamilies. Databases of TFs are available at the World Wide Web at several websites, e. g. BIOBASE Gene Regulation (TRANSFAC® 7.0 Public 2005), the Ohio State University AtTFDB—Arabidopsis transcription factor database, TFSEARCH, and the RIKEN Genomic Sciences Center (GSC) in Japan. The major superclass: basic domains, zinc-coordinating DNA-binding domains, helix-turn-helix, beta-Scaffold Factors with minor groove contacts, and other transcription factors. The major classes are leucine zipper factors (bZIP), helix-loop-helix factors (bHLH), Helix-loop-helix/leucine zipper factors (bHLH-ZIP), NF-1, RF-X, bHSH, Cys4 zinc finger of nuclear receptor type, Cys4 zinc finger of nuclear receptor type, Cys2His2 zinc finger domain, Cys6 cysteine-zinc cluster, Homeo domain, Paired box, Fork head/winged helix, heat shock factors, tryptophan clusters, Ets-type, RHR (Rel homology region), STAT, p53, MADS box, beta-Barrel alpha-helix transcription factors, TATA-binding proteins, HMG, Heteromeric CCAAT factors, Grainyhead, Cold-shock domain factors, Copper fist proteins, HMG (high mobility group), Pocket domain, E1A-like factors, AP2/EREBP-related factors, EREBP and AP2/B3.

As used herein, the term "response element" (RE) refers to the DNA sequence to which a transcription factor binds to and confers an aspect of control of gene expression. A RE binds transcription factors, trans-acting protein factors that regulate transcription. Some REs bind more than one transcription factor, and transcription factors may interact with different affinities with more than one RE. The modified promoters of the present invention desirably contain REs that can enhance gene expression. REs can be identified by a number of techniques known in the art, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. In some embodiments, the RE sequences are palindromes. Generally, RE sequences are orientated in the forward or the reverse direction, and the respective transcription factors will bind their respective RE regardless of the orientation. Examples of some native REs for use with the methods, engineered DNA constructs, engineered promoters, modified promoters are show in Tables 1-6 which provide the native genes and their respective RE, the gene reference (RefSeq) number in the public GENBANK™, the location of the native RE on the native promoter/gene, the sequence of the REs, and the cells for expressing the respective genes using the methods, engineered DNA constructs, engineered promoters, modified promoters described herein. In the tables 1-4 and 6, and described herein, the RefSeq provides the transcribed sequence from the gene and represents the putative transcriptional start site of the respective gene on the respective chromosome. This putative transcriptional start site is numbered as "one" or +1. The negative numbering of the RE means that the RE is on the left side or upstream of the +1 of the gene's putative transcriptional start site location on the chromosome.

Transcription factors interact with their binding sites or RE using a combination of electrostatic (of which hydrogen bonds are a special case) and Van der Waals forces. Due to the nature of these chemical interactions, most transcription factors bind DNA in a sequence specific manner. However, not all bases in the transcription factor-binding site may actually interact with the transcription factor. In addition, some of these interactions may be weaker than others. Thus, transcription factors do not bind just one sequence but are capable of binding a subset of closely related sequences, each with a different strength of interaction. The closely related sequences have a core RE binding motif. For example, although the consensus binding site for the TATA-binding protein (TBP) is TATAAAA, the TBP transcription factor can also bind similar sequences such as TATATAT or TATATAA. The core RE binding motif is "TATA". For example, the human transcription factor FOXL1 is a winged helix-turn-helix/forkhead type TF. It has a core RE binding motif of "ATA" and a consensus sequence of nnnnnATA. The human TF GATA2 and GATA3 are zinc-binding type TFs and they have a core RE binding motif of "GAT". The consensus sequence for GATA2 is n(G/C)ATn and the consensus sequence for GATA3 is (A/T)GAT(A/T)n. The rat, mouse and human TF CREB1 is a basic leucine zipper type TF. It has a core RE binding motif of "TGACGT" and the consensus sequence is (T/G/C)(G/C)A(C/G)(G/A)(T/C)(C/A/T)(A/T). The "n" can be any one of the four standard nucleotide bases A, T, C, G that make up a DNA sequence.

The JASPAR database and TRANSFAC (TRANSFAC® 7.0 Public 2005) are two web-based transcription factor database on transcription factors, their experimentally-proven binding sites, and regulated genes. Its broad compilation of binding sites allows the derivation of positional weight matrices. Web based research engines for transcription factor binding sites are also available, e. g. MatInspector, SIB-HTPSELEX Database and TRANSFAC. One can also search for putative TFRE sites in the upstream promoter region of a gene or even within the gene using search tool such as TFSEARCH, MatInspector, Transcription Element Search Software (TESS) from the University of Pennsylvania, and jPREdictor which predicts cis-regulatory elements from Bielefeld University, Germany and other tools known in the art.

As used herein, the term "responsive" or "stimulated" when used with HNF4α3 or HNF1α and HNF4α3- or HNF1α regulated or dependent gene refers to the increased gene transcription from a promoter that is regulated by these respective transcription factors when the these respective transcription factors are present or provided. The increase is above that seen in the absence of the transcription factors.

As used herein, the term "enhancing expression of a gene" refers to increasing the level of transcription of the gene; the increase is above the level that is normally seen for transcription from the native promoter of the gene.

As used herein, the term "transcription factor response element (TFRE) segment" refers to a DNA sequence that comprises TFRE within. In one embodiment, the segment can also comprise other DNA sequences that are not used for transcription of a gene if the gene is operably linked to the segment.

As used herein, the term "construct" refers to any recombinant polynucleotide molecule such as a plasmid, cosmid, virus, autonomously replicating polynucleotide molecule, phage, or linear or circular single-stranded or double-stranded DNA polynucleotide molecule, derived from any source comprising a polynucleotide molecule where one or more polynucleotide molecule has been linked in a functionally operative manner.

A "DNA construct" would be a recombinant DNA polynucleotide molecule.

An "engineered DNA construct" refers to a recombinant DNA polynucleotide molecule that does not exist naturally but is constructed artificially by molecular techniques. In one embodiment, an "engineered DNA construct" comprises DNA sequences of various origins, much like a chimeric DNA polynucleotide molecule.

An "engineered promoter" refers to an "engineered DNA construct" that can function as a promoter in transcription initiation of a gene that is operably linked to the "engineered promoter". An example of such is mHnf1α$^{Dup4\times H4RE}$ described herein (SEQ. ID. NO: 5).

A "modified promoter" refers to a native promoter in which some changes have been artificially incorporated within. The changes can include deletion and addition of sequences to the promoter. In some embodiments, the changes are designed to alter the transcription activity of the promoter and thereby affect the expression of the gene that is operably linked to it. In some aspects, a "modified promoter" can be considered an "engineered promoter".

The term "vector", as used herein, refers to a nucleic acid construct designed for transfer between different host cells. In one embodiment, a "vector" is referred broadly to any plasmid, phagemid or virus encoding an exogenous nucleic acid. In another embodiment, the term is also be construed to include non-plasmid, non-phagemid and non-viral compounds which facilitate the transfer of nucleic acid into virions or cells, such as, for example, poly-lysine compounds and the like. The vector may be a viral vector that is suitable as a delivery vehicle for delivery of the nucleic acid, or mutant thereof, to a cell, or the vector may be a non-viral vector which is suitable for the same purpose.

An "expression vector" or expression construct" refers to a vector that has the ability to incorporate and express exogenous DNA fragments in a foreign cell. A cloning or expression vector may comprise additional elements, for example, the expression vector may have two replication systems, thus allowing it to be maintained in two organisms, for example in human cells for expression and in a prokaryotic host for cloning and amplification. The term vector may also be used to describe a recombinant virus, e.g., a virus modified to contain the coding sequence for a therapeutic compound or factor. As used herein, a vector may be of viral or non-viral origin. Examples of viral and non-viral vectors for delivery of DNA to cells and tissues are well known in the art and are described, for example, in Ma et al. (1997, Proc. Natl. Acad. Sci. U.S.A. 94: 12744-12746). Examples of viral vectors include, but are not limited to, a recombinant Vaccinia virus, a recombinant adenovirus, a recombinant retrovirus, a recombinant adeno-associated virus, a recombinant avian pox virus, and the like (Cranage et al., 1986, EMBO J. 5: 3057-3063; International Patent Application No. W094/17810, 1994; International Patent Application No. W094/23744, 1994). Examples of non-viral vectors include, but are not limited to, liposomes, polyamine derivatives of DNA, and the like.

A "gene therapy vector" refers to an expression vector that is engineered to incorporate and express DNA sequences or gene products (e. g. mRNA or siRNA) in a host cell for the purpose of correcting a defect or deficiency in that cell. In other words, a "gene therapy vector" is an expression vector adapted for transfer and expression of DNA sequences into a host cell for the purpose of correcting a defect or deficiency in that cell or the organism having the host cell. The product from the expressed DNA sequences functions to correct the defect or deficiency or they cam be used for the treatment of diseases and disorders. For example, there is a deficiency in expression of a particular enzyme in a cell or tissue due to a nonsense mutation in the native gene in the cell. A gene therapy vector is engineered with the correct gene and is inserted into the cell of the tissue having the defect. Expression from the correct gene in the gene therapy vector will produce functional enzyme, replacing the missing enzyme in the cells and tissue. There are gene therapy vectors for use with animal model experiments that utilize the cytomegalovirus immediate early CMV-IE promoter (e.g. pCI-neo cloning vector CVU47120, nts 1-750). This promoter contains numerous response elements to a variety of ubiquitously expressed TFs (e.g. SP1, AP-1, CREBP, SRF, etc.). The "CAG" promoter, composed of the core chicken beta-actin promoter fused the CMV enhancer, a variation that has been used to express TFs (e.g. Klf4, Oct3/4, c-myc, Sox2) capable of reprogramming somatic cells into "induced pluripotent stem cells" (iPS cells). There are limited studies on identifying the REs responsible for activities of these promoters.

As used herein, the term "target gene" in a gene that one wants to enhance gene expression is a host cell when an expression vector or a gene therapy vector is transduced, transfected or inserted into the host cell.

As used herein, a host cell is any cell that is transfected with a vector. In one embodiment, the host cell is selected from a group consisting of hepatocytes, pancreatic beta cells, intestinal mucosal cells, intestinal mucosal cells, renal proximal tubule cells, hematopoietic cells, epidermal cells, endothelial cell, pre-myocytes, myocytes, and muscle cells. In some embodiments, the host cells are any stem cells, of any species, mammalian or non-mammalian. In one embodiment, the host cell is a human cell. In other embodiments, the host cells are any cell within the body of an organism, e.g. when a gene therapy vector or construct is used. The organism can be of any species, mammalian or non-mammalian, including human. In other embodiments, the host cells are the type of cells used for the bioprocess production of commercial therapeutic biologics, e. g. therapeutic antibodies, proteins and peptides. For example, Chinese hamster ovary (CHO) cells and mouse myeloma cells. In other embodiments, the host cell is a cell selected from Tables 1-4.

BRIEF DESCRIPTION OF THE DRAWINGS

FIG. 4C shows the effects of modifications to the human HNF4A P2 promoter in the reporter plasmid pGL3 transfected into HEK-293 cells. Data are presented as fold stimulation vs. pGL3-Basic.

FIG. 6C shows the effect of duplicating the 4×H4RE in the ApoC3 promoter in rat INS-1 β cells and the effects of the size of the spacting between the duplicates of the 4×H4REs upon HNF4α3 stimulation (n=3).

The mutation of the putative Nkx-2.2 element is shown in the mutated sequence (SEQ. ID. NO: 7). The Nkx-2.2 site was mutated by changing all 7 nucleotides (bold underline).

Figure 7E:
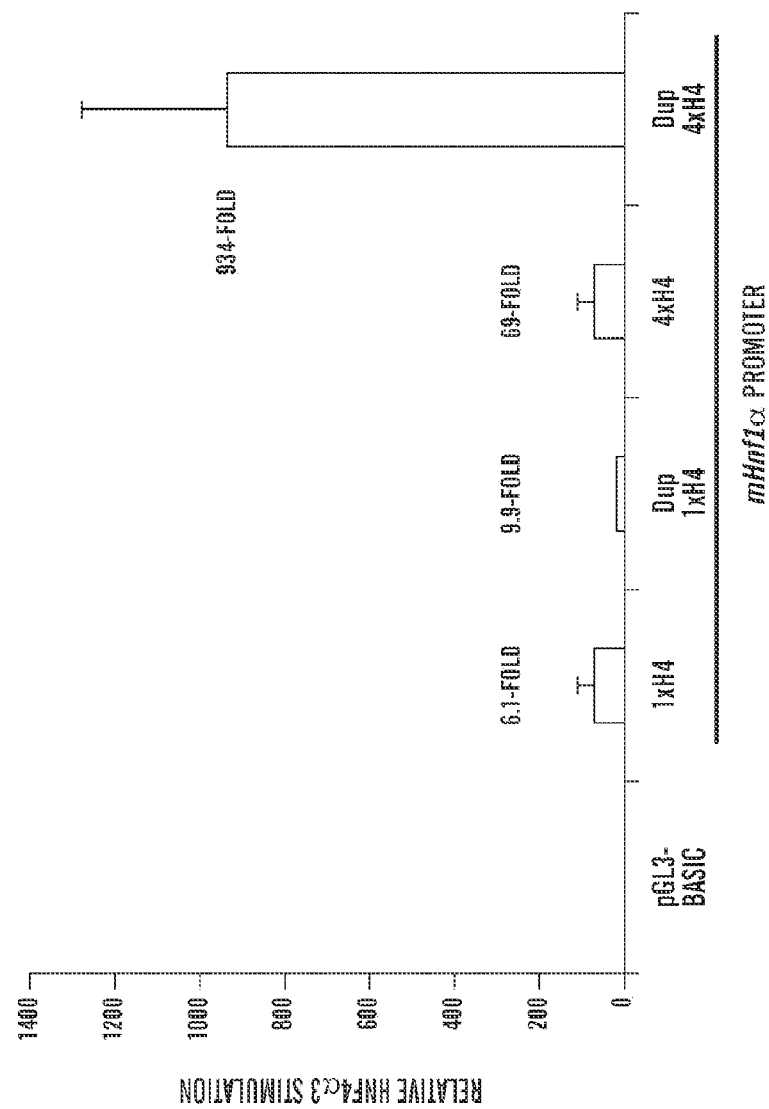
FIG. 7E shows the effects of StuI/NheI duplication on the HNF4α3 stimulated activity of the native mHnf1α promoter.
Figure 7G:
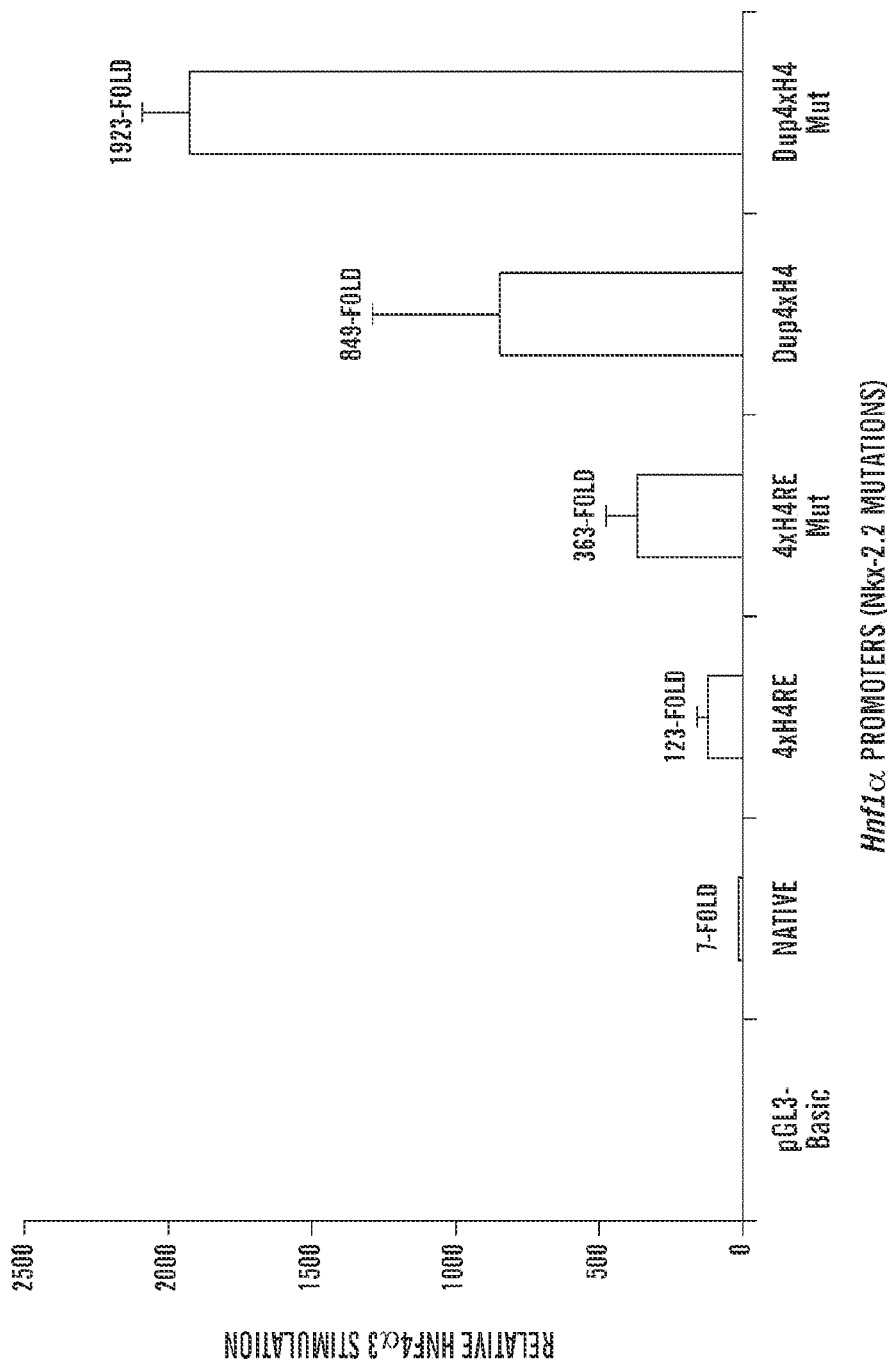
FIG. 7A shows the sequence of the mouse Hnf1α0.7ATG promoter comprising the 692 nucleotide (nt) upstream of the ATG start codon are shown (SEQ. ID. NO: 1). (NM_009327/mouse Hnf1a gene; shown is Mus musculus Chromosome 5: 115,420,851-115,421,545, reverse orientation, with "GAGCT" added to 5-prime end to create SacI site. The native H4RE is boxed and in bold.
FIG. 7B shows the DNA sequences of the synthetic oligonucleotides (SEQ. ID. NO: 2 and 3 in the order of appearance) used to insert 3 additional H4REs (3×H4RE) at the BlpI site on Chromosome 5: 115,420,800 of FIG. 7A. Underlined sequences are H4REs derived from the human G6Pase gene (2 elements on Ch17: −236/−218 & −78/−60 from RefSeq NM_000151) flanking the human HNF1B element (TCF2; −214/−196 from RefSeq: NM_000458).
FIG. 7C shows the sequence of the mouse Hnf1α$^{0.7ATG4\times H4RE}$ promoter with the 3 additional H4REs (boxed) inserted downstream of the original native H4RE (boxed and bold) (SEQ. ID. NO: 4). This is a combination of mouse genomic sequence of FIG. 7A (Ch 5: 115,420,851-115,421,259, reverse orientation, plus the inserted synthetic sequence of FIG. 7B.
FIG. 7D shows the sequence of the mHnf1α$^{Dup4\times H4RE}$ promoter with the 4×H4RE duplicated in tandem and separated by 252 base-pairs (bp) (SEQ. ID. NO: 5). The 338 base pairs (in italic) were duplicated and inserted immediately downstream of the NheI site ("GCTAGC") ending with the 2nd NheI site that is closer to the ATG start codon.
FIG. 7F shows the position of the putative Nkx-2.2 element (double underlined) on the native mHnf1α promoter sequence with respect to the H4RE (boxed) (SEQ. ID. NO: 6) Nkx-2.2 site (bold underline; wild type sequence) in mouse Hnf1α promoter (the region shown is Ch 5: 115,421,112-115,421,260, reverse orientation; the Nkx-2.2 site is located from 115,421,159-115,421,165 (also reverse orientation). Flanking StuI and BlpI sites are underlined and the native H4RE is boxed.

FIG. 7G shows the effects of a mutation of the putative Nkx-2.2 site on the HNF4α3 stimulated activity of the native mHnf1α promoter.

FIG. 8A shows the DNA sequence of the human ApoC3 promoter (SEQ. ID. NO: 8). Sequence −706/−8 with respect to NM_000040 (Chr11:116,700,624-116,703,787), containing 5' GGTACC KpnI site and 3' AGATCT BglII site introduced during PCR cloning, distal H4RE at −702/−690 (box and bold), NdeI site (GCTAGC) introduced at −88/−83, and reversed H4RE at −82/−70 (box and bold).

FIG. 8B shows the DNA sequence of the ApoC3$^{Dup4\times H4RE0.61}$ and the PCT sequences having the 3×H4RE used to construct the modified the human ApoC3 promoter with duplicated 4×H4REs (SEQ. ID. NO: 9, 10, 11 in accordance to appearance). The REs are boxed and bold.

FIG. 8C shows the DNA sequence of the ApoC3$^{Dup4\times H4RE0.3}$ (SEQ. ID. NO: 12). The REs are boxed and bold.

FIG. 9A shows the DNA sequence of the human HNF4A P2 promoter with 1×H1RE (SEQ. ID. NO: 13).

FIG. 9B shows the DNA sequence of the human HNF4A P2 promoter with a duplicated 1× H1RE (SEQ. ID. NO: 14, 15, 16 in the order of appearance) and the sequences of the PCR primers for duplication the H1RE.

FIG. 9C shows the DNA sequence of the human HNF4A P2 promoter with the duplicated 4× H1RE and the 0.84 bp spacing (SEQ. ID. NO: 17, 18, 19 in the order of appearance) and the sequences of the PCR primers for duplication the H1REs.

FIG. 9D shows shows the DNA sequence of the human HNF4A P2 promoter with the duplicated 4× H1RE and the 0.23 bp spacing (SEQ. ID. NO: 20) and the sequences of the PCR primers for duplication the H1REs.

DETAILED DESCRIPTION OF THE INVENTION

The present invention relates to methods, engineered DNA constructs, engineered promoters, modified promoters and DNA sequences to enhance the transcriptional activity of a promoter fragment in mammalian expression vectors while retaining the natural transcription factor dependence or regulation control of the native mammalian promoter or promoter fragment for transcription.

The described engineered promoter enhancement constructs and methods provide safe, normally regulated promoters capable of expressing therapeutic proteins for, for example, new gene transfer and/or gene therapy vectors as well as currently available gene transfer and/or gene therapy vectors and techniques.

In some embodiments, the methods and DNA sequences described herein provide ways to generate safe, normally regulated promoters capable of expressing therapeutic proteins from gene expression vectors. The promoters can be native promoters.

To achieve effective control of gene expression in vivo, higher eukaryotes generally utilize extensive promoter/enhancer/locus control regions spanning many kilobases of DNA, and encompass multiple discrete binding sites for transcription factors that in combination dictates specificity of gene transcription. The extensive enhancer/locus control regions form the regulatory elements of a gene.

The inventors tested several strategies to enhance activity of the hepatocyte nuclear factor HNF4α-dependent Hnf1α promoter (20-23), which was chosen as a prototype due to the key role of the HNF1α transcription factor (TF) in β-cell differentiation and function in the pancreas. The inventors also tested the method with a H1RE-dependent promoter, the HNF4A P2 promoter. The HNF1A (TCF1) and HNF4A genes are mutated in maturity onset diabetes of the young MODY3 (24) and MODY1 (25), respectively, and have been proposed to constitute a bi-stable transcriptional couple in pancreatic β cells (26, 27).

The prototype mammalian promoters and the transcription response elements used by the inventors are examples only, and the same strategy can be applied to any mammalian promoter construct. Therefore, the invention is not limited to the specific exemplary constructs prepared thus far, e.g., HNF4α-dependent and H1RE-dependent promoters. These exemplary promoters are used as examples and for proof-of-concept demonstrations only.

By introducing three more HNF4 REs (H4REs) into the Hnf1α promoter in addition to its existing H4RE to create a 4×H4RE motif or segment, the inventors were able to significantly enhance the HNF4α-stimulated activity. The inventors also added another manipulation duplicating a several hundred nucleotide fragment containing the 4×H4RE to generate non-adjacent 4×H4RE motifs or segments. This duplication step further increased the HNF4α induction to a thousand-fold (See FIG. 2B).

A similar enhancement in HNF4α-stimulated activity was observed by converting the two non-adjacent H4REs in the ApoC3 promoter (28) to 4×H4RE motifs, which resulted in similar enhanced HNF4α-stimulated activity.

Also, comparable enhanced HNF1α-stimulated activity of the HNF1-dependent HNF4A P2 promoter was demonstrated by introducing non-adjacent 4×H1RE motifs (HNF1 REs) in the HNF4A P2 promoter.

HNF4α is nuclear protein receptor type TF and the HNF1α is a homeodomain type TF. The demonstration of this method in three different mammalian promoters which are respectively dependent on different types of TF shows that this method is not limited to homeo-domain type TF or nuclear protein receptor type TF promoters but rather that the method is applicable to any other TF dependent mammalian promoter.

Accordingly, the present disclosure provides a method of enhancing expression of a gene comprising operably linking the gene to an engineered promoter forming a gene expression construct, wherein the engineered promoter comprises at least one transcription factor response element (TFRE) segment, wherein the TFRE segment comprises four to 16 TFREs; wherein all of the TFREs are response elements (REs) of one transcription factor (TF), and wherein each of the TFRE is in forward orientation, and wherein each of the four to 16 TFREs are separated by 9-15 base pairs, and wherein the at least one TFRE segment is inserted upstream (5') of the ATG start codon of the mammalian gene.

In one embodiment, provided herein is a method for enhancing gene expression from a transcription factor (TF) dependent promoter comprising: (a) engineering a DNA construct comprising a transcription factor response element (TFRE) segment comprising between four and 16 consecutive TFRE sequences in a forward orientation, wherein each of the TFRE is separated by 9-15 base-pairs (bp), and wherein all of the TFREs are response elements (REs) of one transcription factor (TF); (b) operably linking the engineered DNA construct upstream (5') of an ATG start codon of a gene regulated by the TF dependent promoter that is operably linked to the gene to make a gene expression construct; and (c) transducing a cell with the gene expression construct.

In one embodiment, the disclosure herein provides a method for enhancing gene expression from a transcription factor (TF) dependent promoter comprising: (a) engineering a first DNA construct comprising a transcription factor response element (TFRE) segment comprising between four and 16 consecutive TFRE sequences in a forward orientation, wherein each of the TFRE is separated by 9-15 base-pairs (bp), and wherein all of the TFREs are response elements (REs) of one transcription factor (TF); (b) engineering a second DNA construct to further comprise at least two TFRE segments of step (a), wherein the TFRE segments are separated by 200-700 base pairs; (c) operably linking the engineered second DNA construct upstream (5') of an ATG start codon of a gene regulated by the TF dependent promoter that is operably linked to the gene to make a gene expression construct; and (d) transducing a cell with the gene expression construct.

In one embodiment, provided herein is a method for modifying a promoter to enhance gene expression from a transcription factor dependent promoter comprising: (a) identifying a native transcription factor response element (TFRE) in a DNA sequence comprising the promoter that is located upstream (5') of an ATG start codon of a gene that is operably linked to the transcription factor dependent promoter; (b) engineering a DNA construct comprising a transcription factor response element (TFRE) segment comprising between four and 16 consecutive native transcription factor RE sequences in forward orientation, wherein each of the TFREs are separated by 9-15 base-pairs (bp); and wherein all of the TFREs are response elements (REs) of a transcription factor (TF) that binds the native TFRE; and (c) operably linking the engineered second DNA construct upstream (5') of the ATG start codon of the gene regulated by transcription factor dependent promoter that is operably linked to the gene to make a gene expression construct.

In one embodiment, provided herein is a method for modifying a promoter to enhance gene expression from a transcription factor dependent mammalian promoter comprising: (a) identifying a native transcription factor response element (TFRE) in a DNA sequence comprising the promoter that is located upstream (5') of an ATG start codon of a gene that is operably linked to the transcription factor dependent promoter; (b) engineering a first DNA construct comprising a transcription factor response element (TFRE) segment comprising between four and 16 consecutive native transcription factor RE sequences in forward orientation, wherein each of the TFREs are separated by 9-15 base-pairs (bp); and wherein all of the TFREs are response elements (REs) of a transcription factor (TF) that binds the native TFRE; (c) engineering a second DNA construct to further comprise at least two TFRE segments, wherein the TFRE segments are separated by 200-700 base pairs; and (d) operably linking the engineered second DNA construct upstream (5') of the ATG start codon of the gene regulated by transcription factor dependent promoter that is operably linked to the gene to make a gene expression construct.

In one embodiment, provided herein is a modified promoter comprising at least one transcription factor response element (TFER) segment, wherein the TFRE segment comprises 4-16 TFREs, wherein all of the TFREs are response elements (REs) of one transcription factor (TF) native to a promoter, wherein the TFREs are in forward configuration, wherein each of the 4-16 TFREs are separated by 9-15 base pairs (bp).

In one embodiment, the disclosure herein provides an engineered DNA construct for increasing gene expression from a transcription factor (TF) dependent promoter comprising at least one transcription factor response element (TFRE) segment, wherein the segment comprises between four and 16 consecutive TFREs in forward direction, wherein each of the TFRE is separated by about 9 to 15 base-pairs (bp), and wherein all of the TFREs are response elements (REs) for one transcription factor (TF).

In some embodiments, the promoters are mammalian promoters. In other embodiments, the promoters are non-mammalian promoters. In other embodiments, the promoters are synthetically made promoter made of parts from many non-related sources, much like a chimeric promoter described in the examples.

In some embodiments, the TFREs are in forward configuration, forward direction or forward orientation. In some embodiments, the TFREs are in reverse configuration, reverse direction or reverse orientation. In one embodiment, all the TFREs in a segment are in the same direction. In other embodiments, the TFREs in a segment have a mixed forward and reverse orientation.

In some embodiments, the TFRE segment of the engineered DNA construct, modified promoter or engineered promoter comprise four, five, six, seven, eight, nine, 10, 11, 12, 13, 14, 15, or 16 TFREs. The multiples of TFRE have to be for the same and one TF but they need not be the native TF, nor do they have to be the same sequence. The TFRE segment can be made by reproducing the native promoter RE, adding consensus REs, or building the multi-copy RE by combining several REs from other highly responsive promoters. One skilled in the art would be able to selected, mix and match TFREs to form the segment as the inventors demonstrated.

Figure 4A:
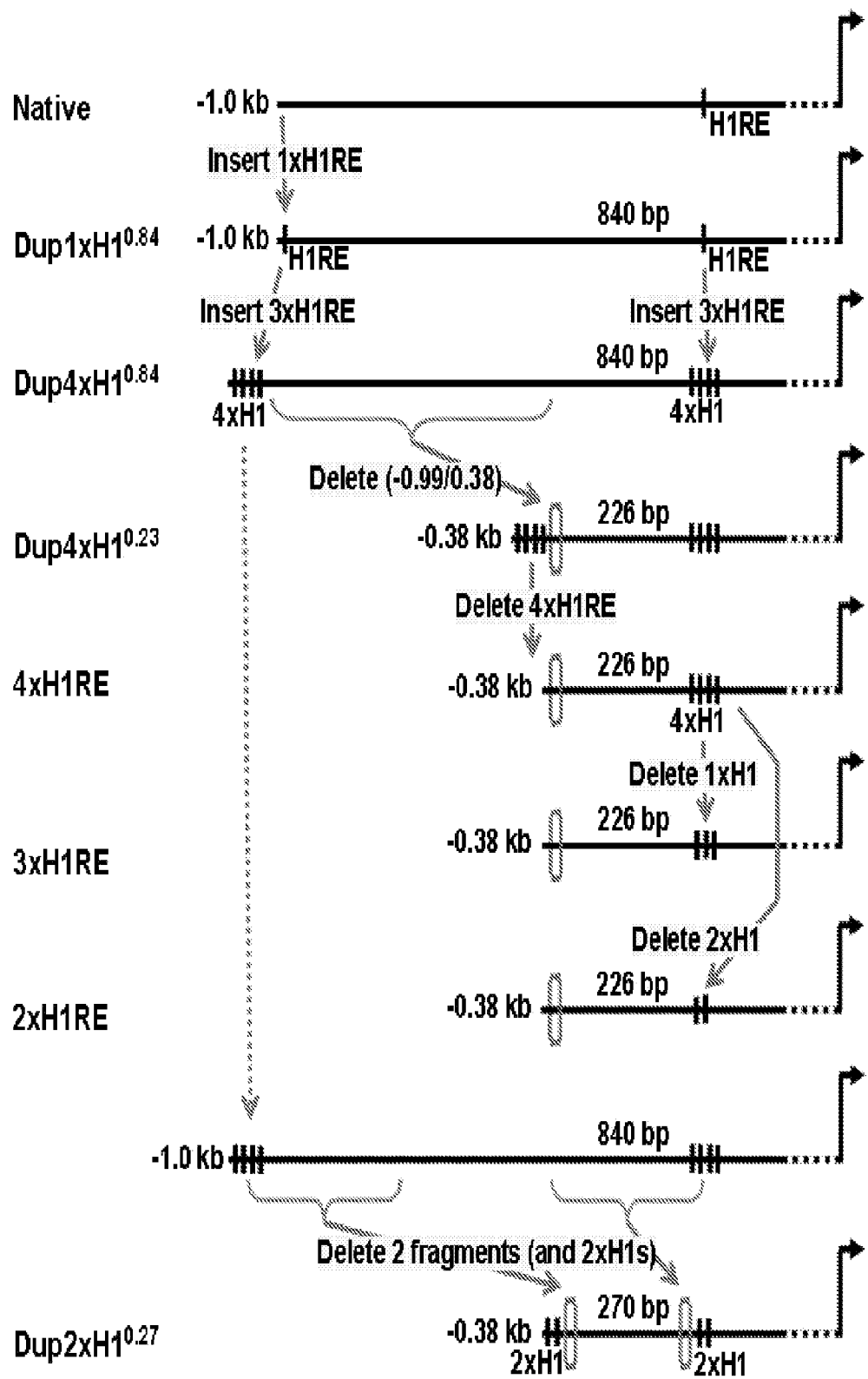
FIG. 4A shows the schematic of modifying native 1.0-kb human HNF4A P2 promoter.
Figure 4B:
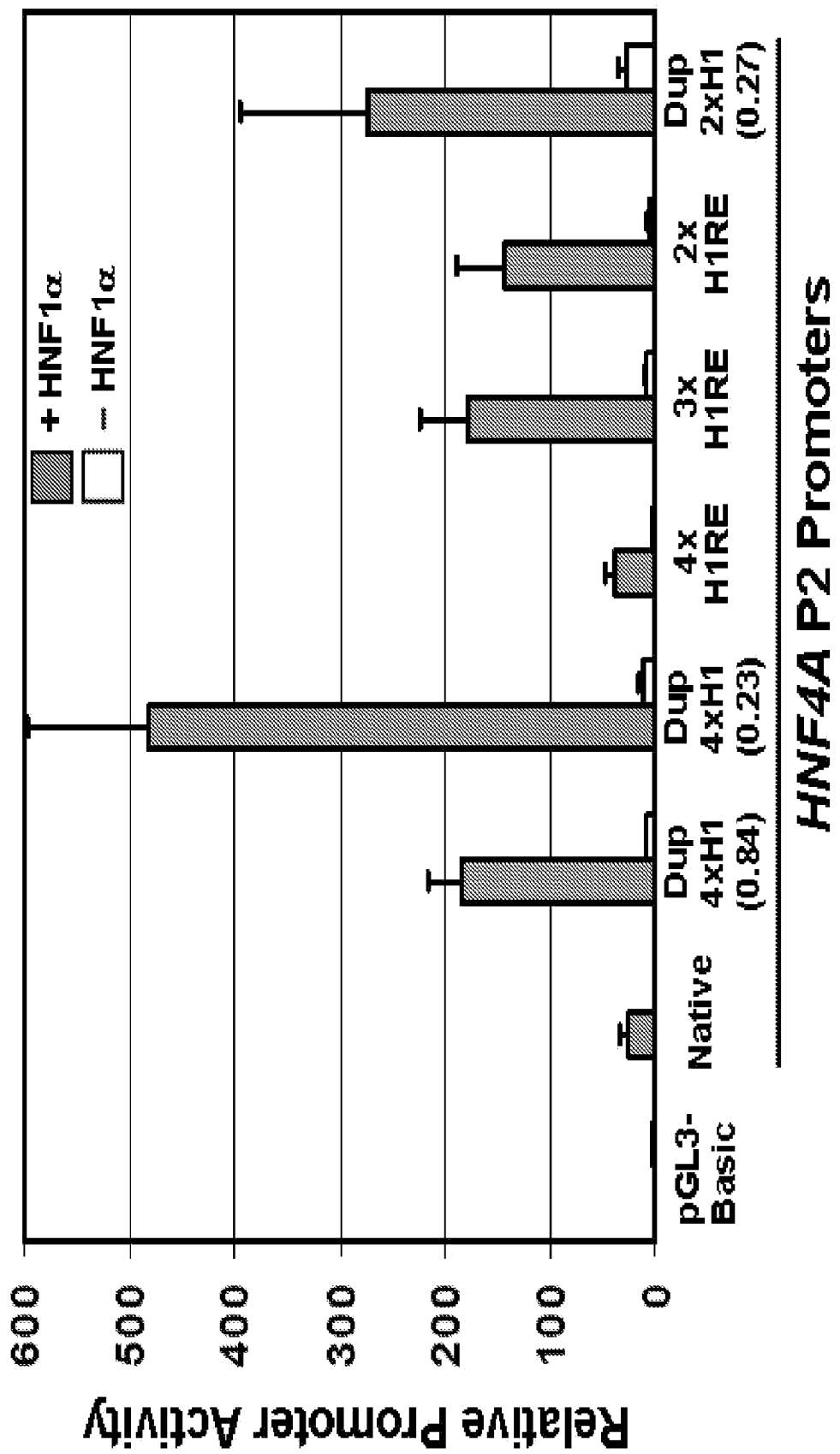
FIG. 4B shows the effects of modifications to the human HNF4A P2 promoter in the reporter plasmid pGL3 transfected into HEK-293 cells. Data are presented as fold stimulation vs. pGL3-Basic (n=5-6).

In some embodiments, the ranges of TFRE in a segment is between 4-5, 4-6, 4-7, 4-8, 4-9, 4-10, 4-12, 4-14 or 4-16. The inventors have shown that simply having two REs can increase the TF stimulated activity (FIG. 4B and 4C). Accordingly, in one embodiment, the TFREs in a segment is two REs. In another embodiment, the ranges of TFRE in a segment is between 2-16, e. g. 2-4, 2-6, 2-8, 2-10, 2-12, 2-14, and 2-16. The inventors have shown that having more REs do not necessary result in a further increased in the TF stimulated activity (FIG. 1B). For the Hnf1α promoter shown in the example, the maximum number of H4RE appears to be ten before there is some negative effects on the stimulated activity.

In addition, the inventors that duplicating the native RE and also duplicating the TFRE segment resulted in increase the TF stimulated activity (FIG. 2B, 4B, 4C, 6D, and 7E).

In one embodiment, the multiple TFREs in a TFRE segment are separated by about 9, 10, 11, 12, 13, 14, or 15 bps. The 9-15 bps are used to space the TFRE apart in a segment. The sequences of the 9-15 bps is not important and can be any of the A, T, C, G nucleotide in a DNA sequence. This range of spacing is approximately that of a single helical DNA turn of 10-11 bp. Such a spacing of 9-15 bp between the multiple REs will have the DNA binding sites on one and the same side of the helix DNA. There are evidences that in situations where multiple TFs are binding on the same side of a DNA helix, they (i. e. the TFs) tend to work cooperatively better to enhance gene expression. Therefore, the 9-15 bp spacing is crucial to the arrangement of the TFREs in the segments described herein.

In some embodiments, the engineered DNA construct, modified promoter and/or engineered promoter described herein are used to form gene expression constructs. In some embodiments, the engineered DNA construct, modified promoter or engineered promoter described herein is a gene expression construct. In some embodiments, the engineered DNA construct, modified promoter or engineered promoter described herein are operably linked to a gene to form a mini gene cassette. In some embodiments, the engineered DNA construct, modified promoter or engineered promoter described herein is a mini gene cassette. The inventors show two such mini gene cassettes, see FIG. 5A in the example.

In one embodiment of the methods, engineered DNA construct, modified promoter or engineered promoter described herein, the gene expression construct is further transduced into a host cell. In another embodiment of the methods, engineered DNA construct, modified promoter or engineered promoter described herein, the mini gene cassette is further transduced into a host cell.

In one embodiment, the host cell is selected from a group consisting of hepatocytes, pancreatic beta cells, intestinal mucosal cells, intestinal mucosal cells, renal proximal tubule cells, hematopoietic cells, epidermal cells, endothelial cell, pre-myocytes, myocytes, and muscle cells. In one embodiment, the host cell expresses the respective TF that binds the TFREs in the segment and thereby regulate the expression of the operably linked gene.

In some embodiments, the host cells are stem cells. For example, adult stem cells, embryonic stem cells, induced pluripotent stem cells, etc. In one embodiment, engineered DNA construct, modified promoter or engineered promoter described herein are used to enhance to expression of differentiating or programming factors in the stem cell.

In other embodiments, the host cells are any cell within the body of an organism, e.g. when a gene therapy vector or construct is used. In some embodiments, the methods, engineered DNA construct, modified promoter or engineered promoter described herein are used to correct a defect or deficiency in a cell or tissue comprising the cell or for treating a disease or disorder.

In some embodiments, the methods, engineered DNA construct, modified promoter or engineered promoter described herein are used for enhancing commercial production of therapeutic biologics. In other embodiments, the host cells are any of the type of cells used for the bioprocess production of commercial therapeutic biologics, e. g. therapeutic antibodies, proteins and peptides. Such cells are well known in the art and one skilled in the art would be able to select an appropriate host cell. For example, Chinese hamster ovary (CHO) cells and mouse myeloma cells are the typical cells used for commercial production of therapeutic biologics. When the methods and constructs are used to enhance gene expression for the commercial production of therapeutic biologics, then one should select from the CHO or mouse myeloma derived cell lines. In other embodiments, the host cell is a cell selected from Tables 1-4.

In one embodiment, the expression of the gene is in vivo. For example, the genes are expressed in the host cells (e. g. the hepatocytes, pancreatic beta cells, intestinal mucosal cells, intestinal mucosal cells, renal proximal tubule cells, hematopoietic cells, epidermal cells, endothelial cell, pre-myocytes, myocytes, muscle cells and stem cells such as adult stem cells, embryonic stem cells, induced pluripotent stem cells, etc. within a mammal, e. g. a mouse or a human.

In one embodiment, the expression of the gene is in vitro. For example, the genes are expressed in the cells (e. g. hepatocytes, pancreatic beta cells, intestinal mucosal cells, intestinal mucosal cells, renal proximal tubule cells, hematopoietic cells, epidermal cells, endothelial cell, pre-myocytes, myocytes, and muscle cells) that are extracted or isolated from a mammal. The cells are cultured ex vivo in tissue culture conditions.

In one embodiment, the engineered DNA construct described herein is operably linked upstream (5') of an ATG start codon of a gene that is operably linked to a TF dependent promoter. In one embodiment, the modified promoter or engineered promoter described herein is operably linked upstream (5') of an ATG start codon of a gene.

In one embodiment, the engineered DNA construct described herein is operably linked upstream (5') of a transcriptional start site of a gene that is operably linked to a TF dependent promoter. In one embodiment, the modified promoter or engineered promoter described herein is operably linked upstream (5') of a transcriptional start site of a gene.

In one embodiment, the gene product of the gene is a protein. In another embodiment, the gene product of the gene is not a protein, e. g. an RNA such as a microRNA.

In one embodiment, the engineered DNA construct, modified promoter or engineered promoter described herein comprises at least two TFRE segments, wherein the two TFRE segments are separated by 200-700 bp. In another embodiment, the engineered DNA construct, modified promoter or engineered promoter described herein comprises up to four TFRE segments, wherein the TFRE segments are separated by 200-700 bp. In one embodiment, the engineered DNA construct, modified promoter or engineered promoter described herein comprises two, three or four TFRE segments. In another embodiment, all the TFRE segments have TFRE that are for the same and one TF.

Figure 3A:
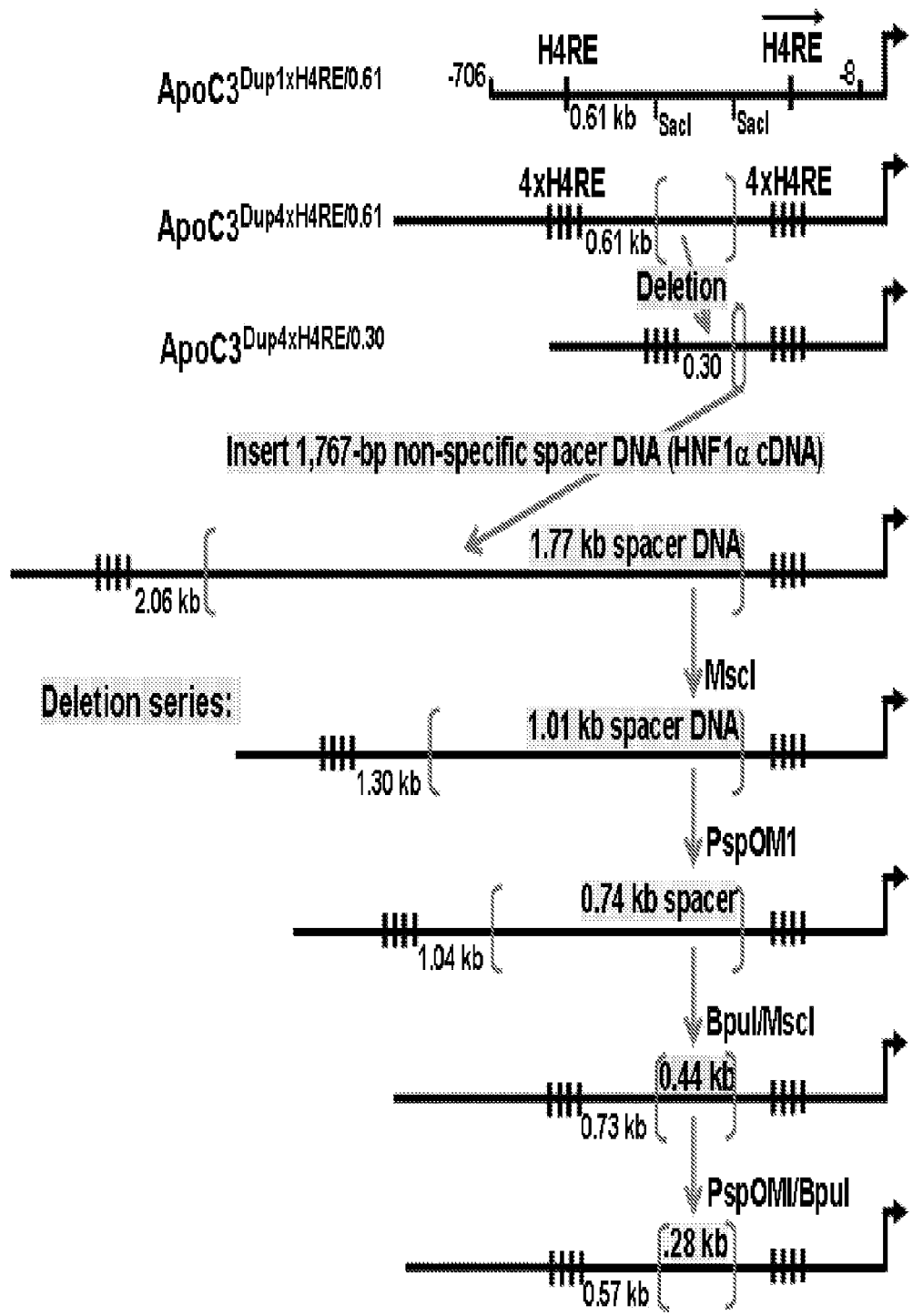
FIG. 3A shows the schematic of modifying the native ApoC3 promoter by inverting the proximal H4RE (ApoC3$^{Dup1\times H4RE/0.61}$), converting both to 4×H4RE motifs retaining the 607-bp spacing (ApoC3$^{Dup4\times H4RE/0.61}$), and then bringing the motifs closer by deleting an intervening 312-bp SacI fragment (ApoC3$^{Dup4\times H4RE/0.30}$). Motif spacing was increased to 2.06 kb by inserting a 1.77-kb human HNF1α cDNA fragment into the SacI site and then sequentially reduced by deleting indicated restriction fragments.
Figure 3B:
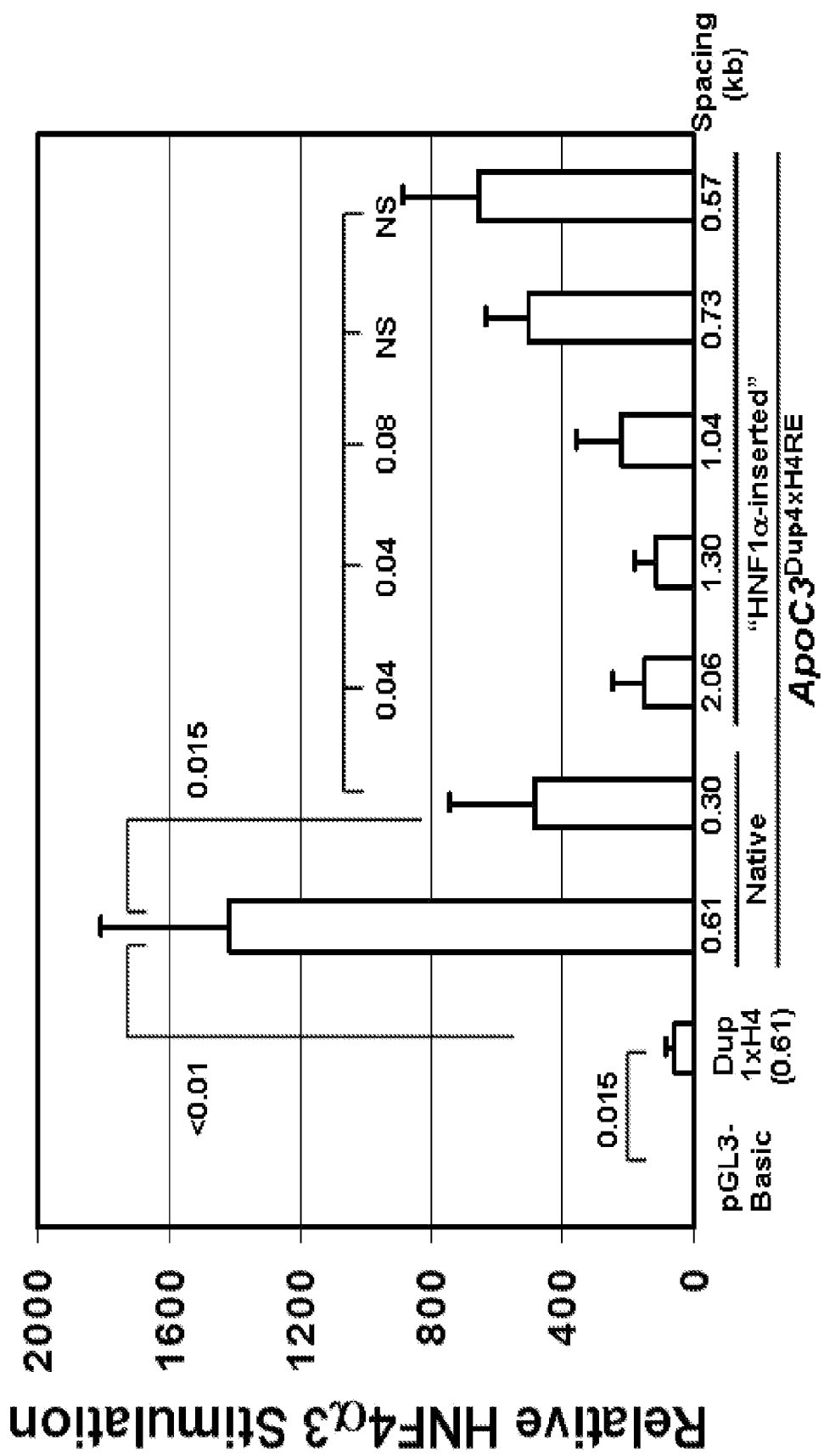
FIG. 3B shows the effect of introducing 4×H4RE motifs into the ApoC3 promoter in the reporter plasmid pGL3 transfected into HEK-293 cells. Data also show the effects of the size of the spacting between the duplicates of the 4×H4REs. Data are presented as fold stimulation vs. pGL3-Basic (n=5-6). Numbers above the histograms indicate p values between activities.

In one embodiment, the multiple TFRE segments are separated by about 200, 250, 300, 350, 400, 450, 500, 550, 600, 650, or 700 bps, including all the whole integer number of by between 200 and 700. The 200-700 bps are used to space the TFRE segment apart in a engineered DNA construct, modified promoter or engineered promoter. In some embodiments, the separation is between 200-300, 200-400, 200-500, 200-600, 300-400, 300-500, 300-600, 300-700, 400-500, 400-600, 400-700, 500-600, 500-700, or 600-700 bp. The sequences of the 200-700 bps is not important and can be any of the A, T, C, G nucleotide in a DNA sequence. The ideal range is between 200-700 bps and it varies with the gene. In the example, the inventors show that a reduction in the size from 0.84-0.23 kilo by increased the TF stimulated activity for the HNF4A promoter (FIG. 4B) while a reduction in the size from 0.61-0. 30 kilo by decreased the TF stimulated activity for the ApoC3 promoter (FIG. 3B). One skilled in the art would be able to experiment to determine the optimum segment spacing for the gene of interest using the methods described in the examples and other methods known in the art.

In one embodiment, at least one TFRE of the TFRE segment is the native to the promoter of the gene, otherwise known as the native promoter TFRE. In another embodiment, the native RE is duplicated in the TFRE segment. In one embodiment, the segment comprises identical TFREs. In another embodiment, the segment comprises all native promoter REs. In other embodiments, none of the TFRE of the TFRE segment is native to the promoter of the gene. In some embodiments, the TFREs of a segment are made up of TFRE from other genes and they are all REs for the same and one TF. In the Example, the segment comprises one native TFRE of the mouse Hnf1 alpha gene, two REs of the human G6Pase gene and one RE from the human HNF1B (TCF2) gene.

In one embodiment, at least one TFRE of the engineered DNA construct, modified promoter or engineered promoter described herein is the native promoter TFRE. In one embodiment of the engineered DNA construct, modified promoter or engineered promoter described herein, all the TFREs are identical. In another embodiment, the engineered DNA construct, modified promoter or engineered promoter described herein comprises all native promoter REs. In other embodiments, none of the TFRE of the of the engineered DNA construct, modified promoter or engineered promoter described herein is native to the promoter of the gene. In some embodiments, the TFREs of engineered DNA construct, modified promoter or engineered promoter described herein are made up of TFRE from other genes and they are all REs for the same and one TF.

In one embodiment of the engineered DNA construct, modified promoter or engineered promoter described herein, the TFRE segment is repeated at least twice and up to four times. In one embodiment, the TFRE segment is duplicated in tandem in the engineered DNA construct, modified promoter or engineered promoter described herein. In another embodiment, the TFRE segment is triplicated in tandem in the engineered DNA construct, modified promoter or engineered promoter described herein. In one embodiment, the TFRE segment is repeated in tandem four times in the engineered DNA construct, modified promoter or engineered promoter described herein.

In one embodiment, the engineered promoter or modified promoter is derived from a native promoter of the gene. In one embodiment, the gene is a mammalian gene. In one embodiment, the engineered promoter or modified promoter is derived from a mammalian promoter. In one embodiment, the mammalian gene is a non-human mammalian gene, e. g. mouse, rat, non-human primate (e. g. monkey, baboon, ape, and chimpanzee), dog, and hamster gene. For example, the mouse hepatocyte nuclear factor 1 alpha (mHNF/alpha). In another embodiment, the mammalian gene is a human gene. For example, the human apolipoprotein C3 (ApoC3), human hepatocyte nuclear factor 4 alpha (HNF4alpha) and human elongation factor 1 alpha (EF1alpha).

In one embodiment, the mammalian promoter is selected from a group consisting human, mouse, rat, non-human primate (monkey, baboon, ape, and chimpanzee), dog, and hamster. In one embodiment, the mammalian promoter is a non-human promoter, e. g. mouse, rat, non-human primate (monkey, baboon, ape, and chimpanzee), dog, and hamster. In one embodiment, the mammalian promoter is a human promoter. Examples include but are limited to the human U6, H1, tRNA, beta-actin, alpha-actin and EF1 alpha promoters.

In one embodiment of the methods, the engineered DNA construct, modified promoter or engineered promoter described herein, the TFRE is for a TF selected from a group of consisting of homeo-domain type, nuclear hormone receptor type, basic helix-loop-helix (bHLH), basic-leucine zipper type (bZIP), winged helix type, and heat-shock type TFs.

In one embodiment, the TF is a homeo-domain type TF. In one embodiment, the homeo-domain type TF is a hepatocyte nuclear factor 1 alpha (HNF1α) TF. In one embodiment wherein the TF is a HNF1α, the gene operably linked to the engineered DNA construct, engineered promoter or modified promoter is a gene selected from the group consisting of hepatocyte nuclear factor 4 alpha (HNF4A), sodium-glucose cotransporter (SLC5A1) and albumin (ALB). In one embodiment wherein the TF is a HNF1α and the gene expression construct or mini gene cassette is transduced into a host cell, the cell is selected from a group consisting of stem cells (e. g. adult stem cells, embryonic stem cells, induced pluripotent stem cells, etc.), hepatocytes, pancreatic beta cells, intestinal mucosal cells, intestinal mucosal cells and renal proximal tubule cells.

In one embodiment, the TF is a nuclear hormone receptor type TF. In one embodiment, the nuclear hormone receptor type TF is a hepatocyte nuclear factor 4 alpha (HNF4α). In one embodiment, wherein the TF is HNF4cc, the gene operably linked to the engineered DNA construct, engineered promoter or modified promoter is a gene selected from the group consisting of Coagulation Factor VIII (procoagulant component), Acyl CoA dehydrogenase, UDP-glucuronosyltransferase 1, ATP-binding cassette, sub-family C (ABCC), Apolipoprotein C3 and hepatocyte nuclear factor 1 alpha (HNF1A). In one embodiment wherein the TF is a HNF4α and the gene expression construct or mini gene cassette is transduced into a host cell, the cell is selected from a group consisting of stem cells (adult stem cells, embryonic stem cells, induced pluripotent stem cells, etc.), hepatocytes, hematopoietic cells, epidermal cells, and endothelial cells.

In one embodiment, the TF is a bHLH type TF. In one embodiment, the bHLH type TF is a MyoD. In one embodiment, wherein the TF is MyoD, the gene operably linked to the engineered DNA construct, engineered promoter or modified promoter is a gene selected from the group consisting of actin, alpha 1, skeletal muscle (ACTA1), myocyte enhander factor 2A (MEF2A) and Catenin beta (CTNNB1). In one embodiment wherein the TF is a bHLH and the gene expression construct or mini gene cassette is transduced into a host cell, the cell is selected from a group consisting of stem cells (adult stem cells, embryonic stem cells, induced pluripotent stem cells, etc.), pre-myocytes, myocytes, and muscle cells.

In one embodiment, the TF is a bHLH type TF. In one embodiment, the bHLH type TF is a neurogenin-3 (Ngn-3). In one embodiment, wherein the TF is Ngn-3, the gene operably linked to the engineered DNA construct, engineered promoter or modified promoter is a OVO homologue-like 1 (OVOhL1) gene. In one embodiment wherein the TF is a bHLH and the gene expression construct or mini gene cassette is transduced into a host cell, the cell is a pancreatic beta cell or stem cells (adult stem cells, embryonic stem cells, induced pluripotent stem cells, etc.).

In one embodiment, the TF is a bZIP type TF. In one embodiment, the bZIP type TF is cyclic AMP (cAMP) RE (CRE). In one embodiment, wherein the TF is CRE, the gene operably linked to the engineered DNA construct, engineered promoter or modified promoter is pyruvate carbolylase. In one embodiment wherein the TF is a bZIP type TF and the gene expression construct or mini gene cassette is transduced into a host cell, the cell is a hepatocyte or stem cells (adult stem cells, embryonic stem cells, induced pluripotent stem cells, etc.).

In one embodiment, provided herein is a vector comprising an engineered DNA construct, engineered promoter or modified promoter construct described herein. In one embodiment, the vector is a gene therapy vector.

In one embodiment, provided herein is a cell comprising a vector of any one embodiments of the engineered DNA construct, engineered promoter or modified promoter construct described herein.

In one embodiment, the engineered DNA construct or modified mammalian promoter is mHnf1α$^{4 \times H4RE}$ or a nucleic acid sequence that is at least 80%, 85%, 90%, 95% or 99% identical to SEQ. ID. NO: 4 which is the DNA sequence depicted in FIG. 7C. The construct was made by the combination of 254 nts upstream of NM_009327 (Chr5: 115,398, 989-115,421,071) and the 1st 219 nts of with the synthetic 3×H4RE segment (FIG. 7B; italicized portion) inserted 50 nts upstream of NM_009327.

In one embodiment, the engineered DNA construct or modified mammalian promoter is mHnf1α$^{Dup4 \times H4RE}$ or a nucleic acid sequence that is 80%, 85%, 90%, 95% or 99% identical to SEQ. ID. NO: 5 which is the DNA sequence depicted in FIG. 7D which is equivalent to the sequence in FIG. 7C except for duplication of the italicized portion 339 nts]

In one embodiment, the engineered DNA construct or modified mammalian promoter is human ApoC3$^{Dup1 \times H4RE}$ or a nucleic acid sequence that is 80%, 85%, 90%, 95% or 99% identical to SEQ. ID. NO: 8 which is the sequence shown in FIG. 8A comprising composite of the nts −706/−8 from human ApoC3 gene [NM_000040 (Chr11:116,700,624-116, 703,787), flanked by incorporated KpnI (GGTACC) and BglII (AGATCT) sites, converting nts −88/−83 (AGCAGG) to an NheI site (GCTAGC), and reversing the proximal H4RE at −82/−70 with regard to NM_000040].

In one embodiment, the engineered DNA construct or modified mammalian promoter is human ApoC3$^{Dup4 \times H4RE/0.6}$ or a nucleic acid sequence that is 80%, 85%, 90%, 95% or 99% identical to SEQ. ID. NO: 9 which is the sequence shown in FIG. 8B which made by the synthetic 69-bp 3×H4RE segment inserted between KpnI site and promoter at nt −706 and synthetic 85-bp 3×H4RE segment inserted into promoter created NheI site at nt −88 from NM_000040 (see FIG. 8B). The two GAGCTC SacI sites are bold.

In one embodiment, the engineered DNA construct or modified mammalian promoter is human ApoC3$^{Dup4 \times H4RE/0.29 \text{ or } 0.3}$ or 80% identical to SEQ. ID. NO: 12 which is the sequence shown in FIG. 8C. The 312 bp between the two SacI sites deleted by restriction enzyme digestion. The ApoC3$^{Dup4 \times H4RE/0.29}$ and ApoC3$^{Dup4 \times H4RE/0.3}$ are used interchangeably.

In one embodiment, the engineered DNA construct or modified mammalian promoter is human HNF4A P2$^{1 \times H1RE}$ or a nucleic acid sequence that is 80%, 85%, 90%, 95% or 99% identical to SEQ. ID. NO: 13 which is the sequence shown in FIG. 9A, where nts −1013/−11 with respect to NM_175194 (Chr20:42,982,441-43,058,311) with KpnI/SacI and XhoI sites incorporated at 5' and 3' ends, respectively, via PCR primers.

In one embodiment, the engineered DNA construct or modified mammalian promoter is human HNF4A P2$^{Dup1 \times H1RE}$ or a nucleic acid sequence that is 80%, 85%, 90%, 95% or 99% identical to SEQ. ID. NO: 14 which is the sequence shown in FIG. 9B. A 20-bp fragment containing a putative H1RE located −8.41 kb upstream from NM_175194 was inserted between the KpnI & SacI sites with the forward PCR primer (H1RE boxed). The downstream reverse primer introduced an NdeI site immediately upstream of the proximal H1RE.

In one embodiment, the engineered DNA construct or modified mammalian promoter is human HNF4A P2$^{Dup4 \times H1RE/0.84kb}$ or 80% identical to SEQ. ID. NO: 17 which is the sequence in FIG. 9C. Modified to the sequence is by inserting a 3×H1RE segment adjacent to each H1RE with the primers shown in FIG. 9C. The three H1REs inserted immediately downstream of the upstream H1RE were derived from the human α1-antitrypsin, β-fibrinogen, and albumin genes, respectively.

The human albumin H1RE was derived from nts −322/−310 with respect to NM_000477 (Chr4:74,268,972-74,287, 627), the human α1-antitrysin H1RE was derived from nts +139/+151 with respect to NM_000295 (Chr14:94,843, 085-94,855,153), and the β-fibrinogen H1RE was derived from nts −58/−46 with respect to NM_005141 (Chr4:155, 484,132-155,493,915).

In one embodiment, the engineered DNA construct or modified mammalian promoter is human HNF4A P2Dup4× H1RE/0.23 kb or 80% identical to SEQ. ID. NO:20 which is the sequence shown in FIG. 9D The 609 bp of DNA was deleted between the BsrGI and PflMI sites.

In practicing the methods and DNA constructs described herein, one would first decide on a gene to which one wishes to increased expression, perhaps in the native cell (e. g. a mammalian cell) of the gene or in a cell used for commercial production of therapeutic biologics. After identifying the native RE of the promoter of the gene (e.g. using genomic data and predicting software known in the art and those described herein), one can construct a DNA construct or modify the native promoter with TFRE segments as described herein. Then, one would operably link the DNA constructs or modified promoter with TFRE segments to the gene of interest, and transduce the resulting construct into a host cell, e. g. the native cell.

In another embodiment, one can choose to make a synthetic DNA construct comprising several REs from different genes, preferably those sequences that have relatively high binding affinity for the chosen TF. The RE of different genes can be from different organisms, e. g. RE from the nematode worm, the fruit fly, and from human.

Transcription factors are proteins that bind to the enhancer or promoter regions and interact such that transcription occurs from only a small group of promoters in any cell. Most transcription factors can bind to specific DNA sequences, and these trans-regulatory proteins or transcription factors (TFs) can be grouped together in families based on similarities in structure. Within such a family, proteins share a common framework structure in their respective DNA-binding sites, and slight differences in the amino acids at the binding site can alter the sequence of the DNA to which it binds. In addition to having this sequence-specific DNA-binding domain, TFs contain a domain involved in activating the transcription of the gene whose promoter or enhancer it has bound. Usually, this trans-activating domain enables that TF to interact with proteins involved in binding RNA polymerase. This interaction often enhances the efficiency with which the basal transcriptional complex can be built and bind RNA polymerase II. There are several families of transcription factors, and those discussed here are just some of the main types.

Homeo domains are conserved DNA-binding domains found in the transcription factors of a wide variety of organisms. There are also known to play an important role in embryogenesis. Homeodomains are about 60 amino acid residues long, and structurally, they consist of three alpha-helices and one flexible N-terminal arm. Homeodomains all bind to DNA at a TAAT core motif. The in vitro the common consensus DNA site that contains the motif (C/G)TAATTG. An example of homeo domain TF is Msx-1 which is encoded by a subfamily of homeobox genes. In a developing embryo, these genes are expressed in craniofacial structures, the neural tube, and in the limbs. Msx-1 specifically interacts with DNA at the sequence (C/G)TAATTG. Biologically, Msx-1 acts as a transcriptional repressor. Another example is the heterodimers between the Pbx/Exd and Hox/HOM-C classes of homeodomain proteins. They are bind regulatory elements in tissue-specific and developmentally regulated genes. The Pbx-Hox heterodimers bind a prototypic element of TGATTAAT.

Basic helix-loop-helix leucine zipper transcription factors are, as their name indicates, transcription factors containing both Basic helix-loop-helix and leucine zipper motifs. An example is Microphthalmia-associated transcription factor. Another example is the sterol regulatory element binding protein (SREBP)

Basic Helix-Loop-Helix (bHLH) Transcription Factors are proteins bind to DNA through a region of basic amino acids (typically 10 to 13 residues) that precedes the first α-helix. The helices contain hydrophobic amino acids at every third or fourth position, so that the helix presents a surface of hydrophobic residues to the environment. This enables the protein to pair by hydrophobic interaction with the same protein or with a related protein that displays such a surface. The muscle-specific transcription factors MyoD and myogenin are examples of TF having this structural motif bHLH. The MyoD family of proteins is active in promoting myogenesis when complexed to either the E12 or E47 proteins—two ubiquitous bHLH proteins). Muscle development is inhibited, though, when the MyoD, E12, or E47 proteins are bound to the Id (inhibitor of differentiation) protein. The Id protein contains the HLH motif, but lacks the basic region that binds to the DNA. Dimerization of Id with MyoD, E12, or E47 interferes with the ability of these proteins to bind DNA, and the expression of Id in cells prevents the activity of the MyoD proteins. The Id protein is made while the muscle cell precursors are still dividing, and they disappear when the myoblasts leave the cell cycle to begin differentiating into myotubes. If Id is overexpressed in cultured myoblasts, they will not differentiate into myotubes.

The structure of basic leucine zipper (bZip) transcription factors is very similar to that of the bHLH proteins. The bZip proteins are dimers, each of whose subunits contains a basic DNA-binding domain at the carboxyl end, followed closely by an a helix containing several leucine residues. These leucines are placed in the helix such that they interact with similarly spaced leucine residues on other bZip proteins to form a "leucine zipper" between them, causing dimers to form. This domain is followed by a regulatory domain that can interact with the promoter to stimulate or repress transcription The C/EBP, AP1, and yeast GCN4 transcription factors are members of the bZip family. Genetic and X-ray crystallographic methods have converged on a model of DNA binding where two alpha helices containing the DNA-binding region are inserted into the major groove of the DNA, each helix finding an identical DNA sequence. The resulting binding looks like that of a scissors or hemostat. Several bZIP proteins bind to the sequence CCAAT; one of the most important is called the CCAAT enhancer-binding protein (C/EBP). C/EBP plays a role in adipogenesis similar to that of the myogenic bHLH proteins in myogenesis.

Zinc finger transcription factors have zinc finger motifs for their DNA-binding domain. Zinc finger proteins include WT-1 (a important transcription factor critical in the formation of the kidney and gonads); the ubiquitous transcription factor Sp1; Xenopus 5S rRNA transcription factor TFIIIA; Krox 20 (a protein that regulates gene expression in the developing hindbrain); Egr-1 (which commits white blood cell development to the macrophage lineage); Krüppel (a protein that specifies abdominal cells in Drosophila); and numerous steroid-binding transcription factors. Each of these proteins has two or more "DNA-binding fingers," a-helical domains whose central amino acids tend to be basic. These domains are linked together in tandem and are each stabilized by a centrally located zinc ion coordinated by two cysteines (at the base of the helix) and two internal histidines. The crystal structure shows that the zinc fingers bind in the major groove of the DNA. The WT-1 protein contains four zinc finger regions, and it is usually expressed in the fetal kidney and gonads. People with one mutant WT1 allele (usually a deletion of the gene or of a zinc finger region) have urogenital malformations and develop Wilm's tumor of the kidney. In mice, both WT1 genes can be deleted by gene targeting, and the resulting mice die in utero, having neither kidneys nor gonads. The WT1 factor binds to the regulatory regions of several genes that are active during kidney development and also is thought to inhibit the expression of certain growth factors.

Nuclear hormone receptors and their hormone-responsive elements. Specific steroid hormones are known to increase the transcription of specific sets of genes. Once the hormone has entered the cell, it binds to its specific receptor protein, converting that receptor into a conformation that is able to enter the nucleus and bind particular DNA sequences. The family of steroid hormone receptors includes proteins that recognize estrogen, progesterone, testosterone, and cortisone as well as nonsteroid lipids such as retinoic acid, thyroxine, and vitamin D. The DNA sequences capable of binding nuclear hormone receptors are called hormone-responsive elements, and they can be in either enhancers or promoters. One set of steroids includes the glucocorticoid hormones (cortisone, hydrocortisone, and the synthetic hormone dexamethasone). These bind to the glucocorticoid hormone receptors and enable the bound receptors to bind to the glucocorticoid-responsive elements in the chromosomes. The steroid-hormone-responsive elements are extremely similar to one another and are recognized by closely related proteins. These steroid receptor proteins are similar to chimeric protein molecules. In general, they each contain three functional domains: (1) a hormone-binding domain, (2) a DNA-binding domain that recognizes the hormone-responsive element, and (3) a trans-activation domain, which is involved in mediating the signal to initiate transcription. These functions can overlap, and all domains appear to have some role in activating transcription. Some steroid receptor proteins have their DNA binding domain as inverted palindromes. For transcriptional activation to occur, the receptor has to enter the nucleus and dimerize with a similar hormone-binding protein. The binding of hormone to the hormone-binding domain appears necessary for dimerization, translocation into the nucleus, and the ability of the DNA-binding region to recognize the hormone-responsive element.

There are similarities among hormone receptor proteins and the similarities among hormone-responsive elements. The consensus sequence of the glucocorticoid-response element is AGAACANNNTGTTCT (where N can be any base) (SEQ. ID. NO: 21). Changing as few as two amino acids will change the specificity of the binding protein. The (palindromic) sequence GGTCACTGTGACC (SEQ. ID. NO: 22) is a strong estrogen-responsive enhancer element that will bind the estrogen-containing receptor protein. Two symmetrical mutations in this sequence, making it GGACACTGTGTCC (SEQ. ID. NO: 23), convert this DNA into a glucocorticoid-responsive enhancer.

Unless otherwise explained, all technical and scientific terms used herein have the same meaning as commonly understood by one of ordinary skill in the art to which this disclosure belongs. Definitions of common terms in molecular biology, gene regulation, promoters and transcription factors can be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about."

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined in any of the following alphabetized paragraphs:

[A] An engineered DNA construct for increasing gene expression from a transcription factor (TF) dependent promoter comprising at least one transcription factor response element (TFRE) segment, wherein the segment comprises between four and 16 consecutive TFREs, wherein each of the TFRE is separated by about 9 to 15 base-pairs (bp), and wherein all of the TFREs are response elements (REs) for one transcription factor (TF).

[B] The engineered DNA construct of paragraph [A], wherein the engineered DNA construct is operably linked upstream (5') of an ATG start codon of a target gene that is operably linked to a TF dependent promoter.

[C] The engineered DNA construct of paragraph [A] or [B], wherein the TFRE is in forward direction.

[D] The engineered DNA construct of any one of paragraphs [A]-[C], wherein the promoter is a mammalian promoter.

[E] The engineered DNA construct of any one of paragraphs [A]-[C], wherein the promoter is a non-human mammalian promoter.

[F] The engineered DNA construct of any one of paragraphs [A]-[C], wherein the promoter is a non-mammalian promoter.

[G] The engineered DNA construct of any one of paragraphs [A]-[F], wherein the engineered DNA construct comprising at least two TFRE segments, wherein the two segments are separated by 200-700 base-pairs.

[H] The engineered DNA construct of any of paragraphs [A]-[G], wherein at least one TFRE is native to the promoter of the gene.

[I] The engineered DNA construct of paragraph [D], wherein the mammalian promoter is selected from a group consisting human, non-primate mammal, rat, dog, and hamster.

[J] The engineered DNA construct of any one of claims [A]-[I], wherein the gene is a mammalian gene.

[K] The engineered DNA construct of paragraph [J], wherein the mammalian gene is a non-human mammalian gene.

[L] The engineered DNA construct of paragraph [J], wherein the mammalian gene is a human gene.

[M] The engineered DNA construct of any of the paragraphs [A]-[L], wherein the TF is a selected from a group of consisting of homeo-domain type, nuclear hormone receptor type, basic-leucine zipper type (bZIP), winged helix type, and heat-shock type TF.

[N] The engineered DNA construct of paragraph [M], wherein the TF is a homeo-domain type TF.

[O] The engineered DNA construct of paragraph [N], wherein the homeo-domain type TF is a hepatocyte nuclear factor 1 alpha (HNF1α) TF.

[P] The engineered DNA construct of paragraph [M], wherein the TF is a nuclear hormone receptor type TF.

[Q] The engineered DNA construct of paragraph [P], wherein the nuclear hormone receptor type TF is a hepatocyte nuclear factor 4 alpha (HNF4α).

[R] The engineered DNA construct of paragraph [O], wherein the gene is a gene selected from the group consisting of nuclear factor 4 alpha (HNF4A), sodium-glucose cotransporter (SLC5A1) and albumin (ALB).

[S] The engineered DNA construct of paragraph [Q], wherein the gene is a gene selected from the group consisting of Coagulation Factor VIII (procoagulant component), Acyl CoA dehydrogenase, UDP-glucuronosyl-transferase 1, ATP-binding cassette, sub-family C (ABCC), Apolipoprotein C3 and hepatocyte nuclear factor 1 alpha (HNF1A).

[T] The engineered DNA construct of any of the paragraphs [A]-[S], wherein the engineered DNA construct is a gene expression construct.

[U] A vector comprising the engineered DNA construct of any one of paragraphs [A]-[T].

[V] The vector of paragraph [U], wherein the vector is an expression vector adapted for gene therapy or gene transfer.

[W] A modified promoter comprising an engineered DNA construct of any one of paragraphs [A]-[T].

[X] A vector comprising the modified promoter of paragraph [W].

[Y] The vector of paragraph [X], wherein the vector is an expression vector adapted for gene therapy or gene transfer.

[Z] A cell comprising a vector of any one of the paragraphs [U], [V], [X], and [Y].

[AA] A method of enhancing expression of a target gene comprising operably linking the gene to an engineered DNA construct of any one of paragraphs [A]-[T] or a modified promoter of paragraph [W] to form a gene expression construct.

[BB] A method for enhancing gene expression from a transcription factor (TF) dependent promoter comprising:(a) engineering a first DNA construct comprising a transcription factor response element (TFRE) segment comprising between four and 16 consecutive TFRE sequences, wherein each of the TFRE is separated by 9-15 base-pairs (bp), and wherein all of the TFREs are response elements (REs) of one transcription factor (TF); (b) engineering a second DNA construct to further comprise at least two TFRE segments of step (a), wherein the TFRE segments are separated by 200-700 base pairs; and (c) operably linking the engineered second DNA construct upstream (5') of an ATG start codon of a target gene regulated by the TF dependent promoter that is operably linked to the gene to make a gene expression construct.

[CC] A method for modifying a promoter to enhance gene expression from a transcription factor dependent promoter comprising: (a) identifying a native transcription factor response element (TFRE) in a DNA sequence comprising the promoter that is located upstream (5') of an ATG start codon of a target gene that is operably linked to the transcription factor dependent promoter; (b) engineering a first DNA construct comprising a transcription factor response element (TFRE) segment comprising between four and 16 consecutive native transcription factor RE sequences, wherein each of the TFREs are separated by 9-15 base-pairs (bp); and wherein all of the TFREs are response elements (REs) of a transcription factor (TF) that binds the native TFRE; (c) engineering a second DNA construct to further comprise at least two TFRE segments, wherein the TFRE segments are separated by 200-700 base pairs; and (d) operably linking the engineered second DNA construct upstream (5') of the ATG start codon of the target gene regulated by transcription factor dependent promoter that is operably linked to the gene to make a gene expression construct.

[DD] The method of paragraph [BB] or [CC], wherein the TFRE is in forward direction.

[EE] The method of any of paragraphs [BB], [CC] or [DD], wherein the promoter is a mammalian promoter.

[FF] The method of any of paragraphs [AA]-[EE], wherein the gene expression construct is further transduced into a host cell.

[GG] The method of paragraph [FF], wherein the host cell is selected from a group consisting of stem cells, adult stem cells, embryonic stem cells, induced pluripotent stem cells, hepatocytes, pancreatic beta cells, intestinal mucosal cells, intestinal mucosal cells, renal proximal tubule cells, hematopoietic cells, epidermal cells, endothelial cell, pre-myocytes, myocytes, and muscle cells.

[HH] The method of paragraph [FF], wherein the expression is in vivo.

[II] The method of paragraph [FF], wherein the expression is in vitro.

This invention is further illustrated by the following example which should not be construed as limiting. The contents of all references cited throughout this application, as well as the figures and table are incorporated herein by reference.

EXAMPLE

Effective gene therapy requires regulated gene expression and vector safety. Our goal was to generate safe, normally regulated promoters capable of expressing therapeutic proteins. We developed a method to essentially exponentially increase native promoter activity while retaining inherent regulation by inserting multi-copy response elements (REs) into non-adjacent locations. For the hepatocyte nuclear factor (HNF) 4α-dependent Hnf1α(MODY3) gene, HNF4α stimulation increased from 5-fold to 90-fold by inserting 3 additional HNF4α REs (H4REs). Constructing a promoter with two 4×H4REs 0.25 kb apart by duplicating the 4×H4RE fragment increased stimulation to >1000-fold. HNF4α-induced protein expression by the duplicate 4×H4RE Hnf1α promoter was comparable to a viral promoter. Converting the two Apolipoprotein C3 (ApoC3) H4REs spaced 0.61 kb apart to 4×H4REs achieved a similar result. Increasing spacing to 2.1 kb with non-promoter DNA abolished the augmentation. Converting the HNF1α RE of the HNF4A (MODY1) P2 promoter to 4×H1RE and adding a second 4×H1RE 0.84 kb upstream increased HNF1α stimulation from 26-fold to >200-fold. Deleting intervening DNA to produce 0.23-kb spacing increased stimulation to >500-fold.

Materials and Methods

Cell Lines:

HEK-293 cells were provided by Thomas J. Gardella and were grown in Dulbecco's modified Eagle's medium (DMEM) supplemented with 10% fetal bovine serum, 100 units of penicillin and 50 units of streptomycin. Rat INS-1 insulinoma cells were grown as recommended (29).

Plasmids and DNA Constructs:

Promoters were inserted in pGL3-Basic (Promega, Madison, Wis.) for manipulation and analysis.

Hnf1α:

Because the transcription start site of the mouse Hnf1αgene has not been definitively established (See FIG. 7A), the region 692 bp upstream of the ATG codon was incorporated to ensure inclusion of any functional mouse promoter elements (referred to as mHnf1α$^{0.7ATG}$). FIG. 7A Sequence of the mouse Hnf1α0.7ATG promoter: The 692 nt upstream of the ATG start codon are shown. Relevant features include (with respect to the ATG): restriction sites for StuI (aggcct; −310), BlpI (gctnagc; −267), and NheI (gctagc; −43); H4RE (boxed; −279); and putative transcription start sites for mouse Hnf1α ("a"; −218; RefSeq: NM_009327), Bach, I., et al., 1990, Genomics, 8:155-164) and human Hnf1α("c"; −23; RefSeq: NM_000545), Kuo, C. J., et al., 1990, Proc. Natl. Acad. Sci. U.S.A., 87:9838-9842).

This promoter has comparable activity to the previously studied mHnf1α$^{−497}$ promoter that comprised 510 bp ending 182 bp upstream of the ATG (30). FIG. 7B shows the DNA sequences of the oligonucleotides (SEQ. ID. NO: 2 and 3) used to insert 3 additional H4REs (3×H4RE). The 3-nt BlpI overhang (TnA) allows for directional insertion of DNA fragments. The two complimentary 70-mers were synthesized with unique overhangs to match the Hnf1α promoter site. Potentially useful restriction sites were also incorporated into the sequence. Nucleotides adjacent to the overhangs were chosen to reconstitute the upstream BlpI site while destroying the downstream site following insertion. This design permits sequential insertion of additional fragments to generate 7×H4RE, 10×H4RE, etc.

The mHnf1α$^{0.7ATG}$ promoter was modified in two ways. First, additional sets of three H4RE sequences, derived from the two elements found in the human G6Pase gene flanking the element from the human HNF1B gene (TCF2), separated by 9-15 bp (3×H4RE), were sequentially inserted into the BlpI site 8 bp downstream of the native H4RE. The 3-nt BlpI overhang permitted directional insertion of the 3×H4RE duplex and the oligonucleotides were designed to preserve only the BlpI site adjacent to the native H4RE. FIG. 7C shown the sequence of the mHnf1α$^{0.7ATG4×H4RE}$ promoter with 4 H4REs.

Second, the 0.34-kb fragment containing the 4×H4RE was duplicated between the StuI site 20 bp upstream of the native H4RE and the NheI site 43 bp upstream of the ATG start codon; creating two 4×H4RE motifs separated by ~250 bp. FIG. 7D shows the sequence of the mHnf1α$^{Dup4×H4RE}$ promoter. The mHnf1α$^{4×H4RE}$ promoter was digested with NheI, blunt-ended with Klenow, and further digested with NcoI to obtain a promoter with the proximal 43 bp removed. A StuI/NcoI fragment from the mHnf1α$^{4×H4RE}$ promoter was ligated into this vector, creating two 4×H4RE motifs or segments separated by 252 bp. Only the NheI site is reconstituted at the StuI/NheI junction (bold).

ApoC3 promoter: Several modifications were made to the human ApoC3 promoter (−890/+24), which has two conserved H4REs separated by 607 bp, −70 and −690 from the transcription start site with the proximal H4RE in reverse orientation (31). The proximal element was converted to the forward direction (a). The H4REs were converted to 4×H4RE motifs or segments. The PCR product was digested with Acc65I/NheI and ligated with the proximal element in converted, forward orientation promoter in step (a). Spacing between the 4×H4RE motifs was adjusted by restriction endonuclease digestion (c), insertion of a cDNA, and removal of various lengths of the cDNA.

A shorter −706/−8 promoter fragment was generated by PCR in which both H4REs were converted to forward 4×H4RE motifs. The H4RE is bold and italicized and the restriction enzyme sites are in bold.

The PCR primers used to construct the duplicate 1×H4RE ApoC3 promoter: N/Apoc3/Acc65I/F (forward primer inserts KpnI site immediately upstream of the distal H4RE):

(SEQ. ID. NO: 24)
gagcctggtaccgggaggggcaaaggcc

R/Apoc3/BglII/NheI/R (reverse primer inserts BglII site at 3' terminus, converts proximal H4RE from reverse to forward orientation, and creates adjacent NheI site):

(SEQ. ID. NO: 25)
aaatttAGATCTAGGAGGGTTCTGACCTGTTTTATATCATCTCCAGGGCAGCAGGCACTGAGGA CCCAGGGCGC*TGACCTTTGCCCA*gctagcGACCAGTGGAGATGAGG The PCR primers used to construct the duplicate 4×H4RE ApoC3 promoter: Apoc3/4×H4RE/Acc65I/BsiWI/F (forward primer converts distal H4RE to a 4×H4RE motif with flanking KpnI and BsiWI sites):

(SEQ. ID. NO: 10)
aaattTggtaccAAGCA*GTCCAAAGATCATGAATTCACAATGCCAAAGTTAACGTACGGCTGAG*

*TCCAAAGTTCA*GGTCGAgggaggggcaaaggcctc

Apoc3/3×H4RE/NheI/SpeI/R (reverse primer inserts three H4REs to create a proximal 4×H4RE motif by ligating into duplicate 1×H4RE promoter NheI site):

Downstream 4×H1RE: human albumin—human α1-AT—human β-fibrinogen—proximal H1RE
Sites: BsiWI/Alb/AvrII/α1-AT/NheI/β-fib/NdeI/Prox (SEQ. ID. NO: 11)
```
AAATTTGCTAGCGTCGACTGATCTTTGGACTCACATATGCCTGAACTTTGGACTTGTACTAGTA TTAACTTTGGCATGACCAGTGGAGATGAGGgcc
```

Second, the distance between the two motifs was reduced to ~0.30 kb by deleting 312 bp between the two SacI sites (−522 and −210). Third, a 1.77 kb HNF1α cDNA SacI fragment, encompassing codons 12-600, was inserted into the promoter SacI site in the forward orientation to create a 2.06-kb spacer between the 4×H4RE motifs. Finally, various fragments of the HNF1α cDNA were removed by restriction endonuclease digestion to generate a series of promoters with shorter spacing between the two 4×H4RE motifs: (i) a 757-bp fragment was deleted with MscI (codons 282-533); (ii) a 1,022-bp fragment was deleted with PspOMI (codons 35-375); (iii) a 1,323-bp fragment was removed between the distal Bpu10I site and the proximal MscI site (codons 93-533); and (iv) a 1,484-bp fragment was removed between the distal PspOMI site and the proximal Bpu10I site (codons 35-530).

HNF4A P2 promoter: The native 1.0-kb HNF4A P2 promoter, with one conserved H1RE at −0.15 kb, was initially modified by inserting the H1RE found at −8.41 kb in the HNF4A gene at the 5-prime end to generate a promoter with two H1REs separated by 840 bp (HNF4A-P2$^{Dup1×H1/0.84}$). Subsequently, both H1REs were converted to 4×H1RE motifs (HNF4A-P2$^{Dup4×H1/0.84}$). This promoter was further modified in several ways. First, 0.61 kb of DNA adjacent to the distal motif was deleted to create a 226-bp spacer (HNF4A-P2$^{Dup4×H1/0.23}$). The distal 4×H1RE was deleted from this promoter, followed by sequential removal of proximal H1REs. Finally, an HNF4A-P2$^{Dup2×H1/0.27}$ promoter was constructed from HNF4A-P2$^{Dup4×H1/0.84}$ by deleting two H1REs and adjacent DNA from each motif.

A human HNF4A P2 promoter fragment (−1013/−11) was cloned by PCR and ligated into pGL3-Basic using incorporated SacI and XhoI sites (native 1.0-kb promoter). Putative H1RE located at −8,410 bp was incorporated into the 5-prime end of the native promoter, creating a promoter with duplicate 1×H1RE separated by an 840-bp spacer. Both H1REs were converted to forward 4×H1RE motifs to create a duplicate 4×H1RE promoter with the same spacing. The 4×H1RE motifs were brought closer by removal of the 610-bp BsrGI/PflMI fragment, leaving a 230-bp spacer. Removing the distal 4×H1RE motif from the full-length duplicate 4×H1RE promoter with KpnI/PflMI produced a promoter with a single 4×H1RE motif and 226 bp upstream DNA. From this promoter, one H1RE was removed by BsiWI/AvrII to create a 3×H1RE motif and two H1REs were removed by BsiWI/NheI to create a 2×H1RE motif.

HNF4α-P2 Promoter: KpnI/SacI to XhoI fragment is shown in FIG. 9A (SEQ. ID. NO: 13).

HNF4α-P2$^{Dup4×H1RE}$ Promoter Sequence: Restriction endonuclease deletions are as follows. Deletion of Dup4×H1RE between BsrGI (tgtaca; −0.99, & PflMI (ccannnnntgg; −0.38) gives 0.23-kb spacing. Deletion between KpnI (ggtacc; 5-prime end) & PflMI (ccannnnntgg; −0.38) gives 0.38-kb promoter with single 4×H1RE motif. Deletion of 4×H1RE promoter between BsiWI (cgtacg; −0.19) & AvrII (cctagg; −0.19) gives 0.38-kb promoter with single 3×H1RE motif. Deletion of 3×H1RE promoter between BsiWI (cgtacg; −0.19) & NheI (gctagc; −0.19) gives 0.38-kb promoter with single 2×H1RE motif. Deletion of Dup4×H1RE between MluI (acgcgt; −0.99) & StuI (aggcct; −0.64) and between PflMI (ccannnnntgg; −0.38) & NheI (gctagc; −0.19) gives Dup2×H1RE with 0.27-kb spacing.

HNF4α-P2$^{Dup4×H1RE}$ Promoter Sequences are shown in FIG. 9C and 9D (SEQ. ID. NO: 17 and 20)

CMV Promoter:
The CMV-IE (immediate early) promoter was excised from pcDNA3.1 (Invitrogen) and inserted into pGL3-Basic to assess its activity in comparison to modified native promoters.

CMV Expression Plasmids:
Plasmid pcDNA3.1 (INVITROGEN™) was used for all expression plasmids. Vectors for HNF4α variants were described previously (30, 32). HA-tagged rat HNF4α3 (rHNF4c6$^{HA}$) was constructed by fusing two hemagglutinin epitopes to the C-terminus of the rat HNF4α3 sequence.

HA-Tagged Rat HNF4α3 (rHNF4α3$^{HA}$):
Two copies of the HA epitope (YPYDVPDYA (SEQ. ID. NO: 26)) were inserted separated by 2 Gs (YPYDVPDYA-GG-YPYDVPDYA (SEQ. ID. NO: 27)). The reverse primer contained this coding sequence between an XbaI site and the C-terminus of HNF4α9. Amplification with this primer and an exon 7 forward primer generated a product from which an EcoNI (exon 8)/XbaI fragment could be used to HA-tag any exon 8$^+$ variant. Similarly, the EcoNI/XbaI fragment was used to convert the HNF4α1 coding sequence in pcDNA3.1 (Huang, J., et al., 2008, Diabetes Metab. Res. Rev., 24:533-543) to rHNF4α3$^{HA}$. To construct the augmented P2 promoter HNF4a3 expression plasmid, the rHNF4α3$^{HA}$ cDNA was excised with HindIII/XbaI and inserted into pGL3/HNF4A-P2$^{Dup4×H1RE}$ in place of the Luciferase gene (HNF4α-P2$^{Dup4×H1RE}$/rHNF4a3$^{HA}$). Restriction sites ale single underlined in the sequences below.

Human/h4α9-HA2/XbaI/R (anti-sense):

(SEQ. ID. NO: 28)
```
TTAATCTAGATTAAGCATAGTCCGGGACGTCATAGGGATATCCGCCCGCATAGTCAGGAACATC

GTATGGGTAAGCAACTTGCCCAAAGC
```

Upstream 4×H1RE: distal H1RE—human α1-AT—human β-fibrinogen—human albumin

Sites: KpnI/Distal/SacI/α1-AT/M/uI/β-fib/BssHII/Alb/BsrGI (This is a synthetic polynucleotide containing antisense sequence for the XbaI restriction enzyme site, 2 copies of the HA hemagglutinin epitope separated by 2 glycine residues, and 17 nucleotides complementary to 3' terminus of the cDNA coding frame (to fuse the HA epitope codons to the C-terminal end). The HA epitope codons translate to the Tyr-Pro-Tyr-Asp-Val-Pro-Asp-Tyr-Ala (SEQ. ID. NO: 29) sequence found in HA but the particular combinations used do not occur in any extant influenza virus genome sequenced to date.)

DNA sequence (sense): GCTTTGGGCAAGTTGCT TAC CCA TAC GAT GTT CCT GAC TAT GCG GGC GGA TAT CCC TAT GAC GTC CCG GAC TAT GCT TAA TCTAGAT-TAA(SEQ. ID. NO: 30) This is the DNA sequence that is synthesized by PCR. The triplet codons are separated for easier comprehension. "GGC" and "GGA" both encode glycine to form a spacer between the 2 HA epitopes for improved antibody binding.

Augmented promoter expression plasmids: The human HNF1α coding sequence was excised from pcDNA3.1 with PmeI and XbaI and inserted between the NcoI (blunt-ended) and XbaI sites of the pGL3 plasmid, replacing the Luciferase gene (mHnf1α$^{Dup4 \times H4RE}$/hHNF1α). Similarly, the rHNF4α3$^{HA}$ coding sequence was excised from pcDNA3.1 with HindIII and XbaI and fused to the HNF4A-P2$^{Dup4 \times H1/0.23}$ promoter. up4XH4RE Human HNF1α: Fusion of the human HNF1α cDNA to the mHnf1α$^{Dup4XH4RE}$ promoter: The cDNA was excised from the pcDNA3.1 vector using PmeI (blunt-end) and XbaI and inserted into pGL3-mHnf1α$^{Dup4 \times H4RE}$ in place of the Luciferase gene between the blunt-ended NcoI site and XbaI. Note that the pGL3 ATG start codon is reconstituted but that this codon is in frame with the ATG start codon of the inserted HNF1α cDNA. ATG are in bold in the sequences below.

GTTTAAACTTAAGCTT (pcDNA PmeI/HindIII) (SEQ. ID. NO: 31) This is the pcDNA3.1+ multiple cloning site nts 901-916; PmeI blunt cuts between "T" & "A" of "GTT-TAAAC."

AAGCTTGGCGGTAGAGGAGCCATGG (HNF1α HindIII/ATG) (SEQ. ID. NO: 32) This is the rat HNF1α cDNA NM_012669 nts 136-154 with 5' "AAGCTT" HindIII site for cloning. The ATG at NM_012669 nts 151-153 is the HNF1α start codon.

CCATGAAACTTAAGCTTGGCGGTAGAG-GAGCCATGG (Chimeric ATG/PmeI/HindIII/cDNA) (SEQ. ID. NO: 33). This is the he 1st 5 nts are from pGL3-Basic, nts 86-90 of U57024, part of a "CCATGG" NcoI site containing the ATG start codon for the Luciferase gene. When the 5' overhang of the digested NcoI site is filled in with Klenow, the CCATG is fused to AAAC . . . of pcDNA3.1+nts 905 and following that was created by PmeI digestion.

CC ATG AAA CTT AAG CTT GGC GGT AGA GGA GCC ATG G (Repeated with codon breaks) (SEQ. ID. NO: 34) This is the pGL3-Basic U57024 nts 86-90, pcDNA3.1+ nts 905-916, and rat HNF1α cDNA NM_012669 nts 136-154.

Transfection Analyses

Transient transfections were performed with LIPO-FECTAMINE 2000 REAGENT® (INVITROGEN™, Carlsbad, Calif.) in either 48-well clusters to assess promoter activities by DUAL-LUCIFERASE® (Promega) as previously described (33) or 24-well clusters to measure protein expression by immunoblotting (see below). For reporter assays, a total of 400 ng DNA was added with 200 ng each reporter plasmid (e. g. pGL3-Basic, pGL3-Basic-Hnf4α-P2$^{Dup4 \times H1/0.23}$, pGL3-Basic-mHnf1α$^{4 \times H4RE}$, pGL3-Basic-mHnf1α$^{Dup4 \times H4RE}$, pGL3-Basic-ApoC3$^{Dup4 \times H4RE/0.61}$) and expression vector (e.g. pcDNA-HNF4a3 expression vector) (or empty pcDNA3.1). Reporter assays were performed in triplicate at least twice (n=6-9).

Immunoblot Analyses

Western blotting was performed to assess protein expression from augmented promoter expression plasmids. Plasmids were transiently transfected into HEK-293 cells or INS-1 cells with or without co-transfected pcDNA-HNF4α3 expression plasmid. Extracts were prepared 48 h later with IP buffer (50 ml Tris-HCl, pH 8.0, 100 mM NaF, 30 mM Na-pyrophosphate, 2 mM $Na_2MoO_4$, 1 mM $Na_3VO_4$, 5 mM EDTA plus protease inhibitors). Immunoblotting was performed with 40 µg total protein as described (33) or any method known to one skilled in the art. Primary antibodies used were Anti-HA (mouse monoclonal clone 7, specific for human influenza virus hemagglutinin; H3663; Sigma, St. Louis, Mo.) and Anti-HNF1α (C-19) (sc-6547; Santa Cruz Biotechnology, Inc., Santa Cruz, Calif.). Secondary antibodies were goat anti-mouse IgG-HRP (Santa Cruz) and donkey anti-goat IgG-HRP (Jackson ImmunoResearch Laboratories, Inc., West Grove, Pa.). SUPERSIGNAL West Pico (Pierce, Rockford, Ill.) was also used for detection.

Statistical Analyses

Data are presented as means±SD. Promoter activities were compared by two-tailed paired t tests, with p<0.05 taken as significant. When the number of observations differed, a two-tailed t test assuming unequal variances was substituted.

Results

Impact of H4RE Copy Number on Hnf1α Promoter Activity

Figure 1A:
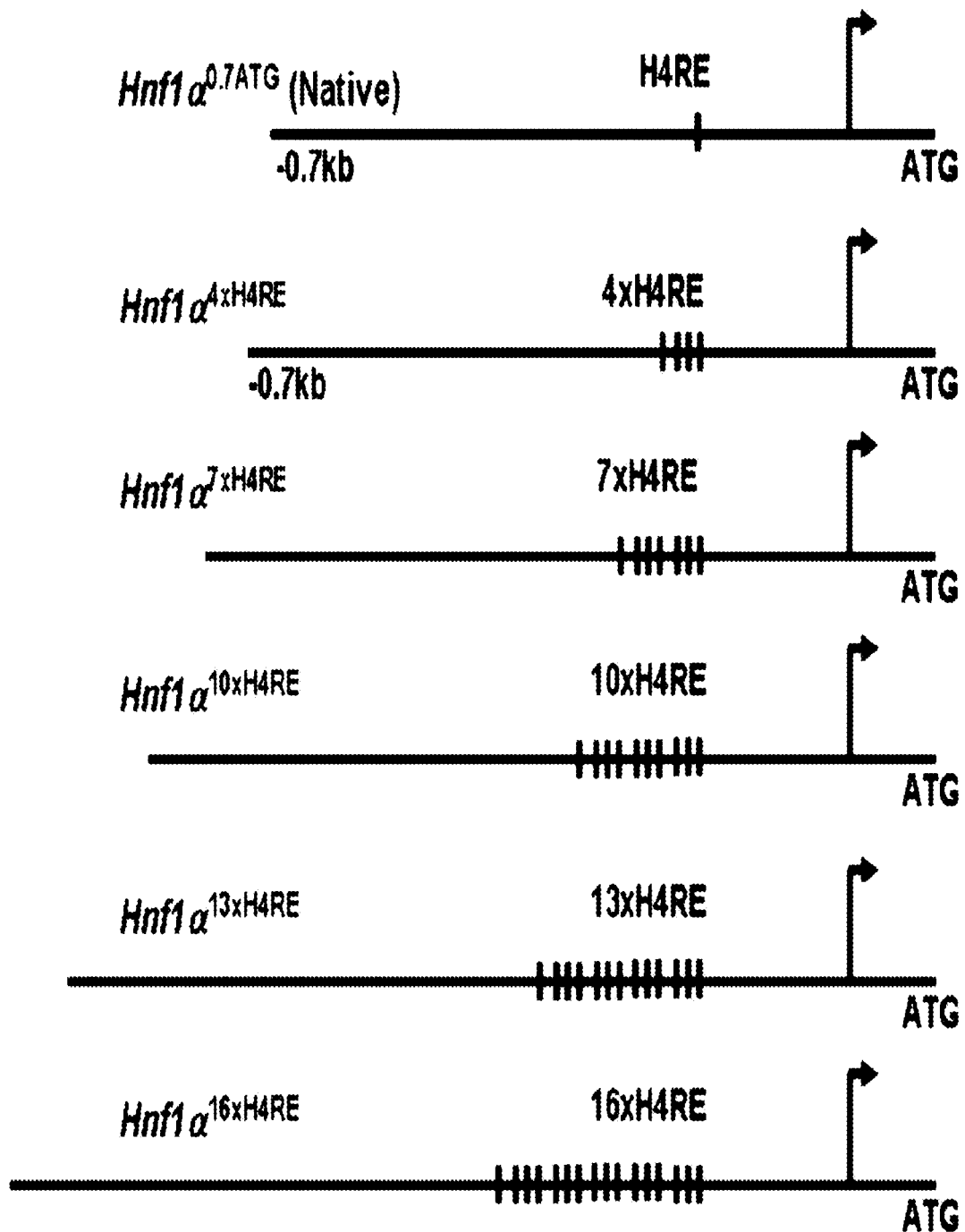
FIG. 1A shows a schematic of the modification of the native mHnf1α promoter and 5-prime UTR (692 bp upstream of the ATG start codon) by inserting additional H4REs in increments of three immediately downstream of the native H4RE. The arrow indicates the transcription start site (not to scale).
Figure 1B:
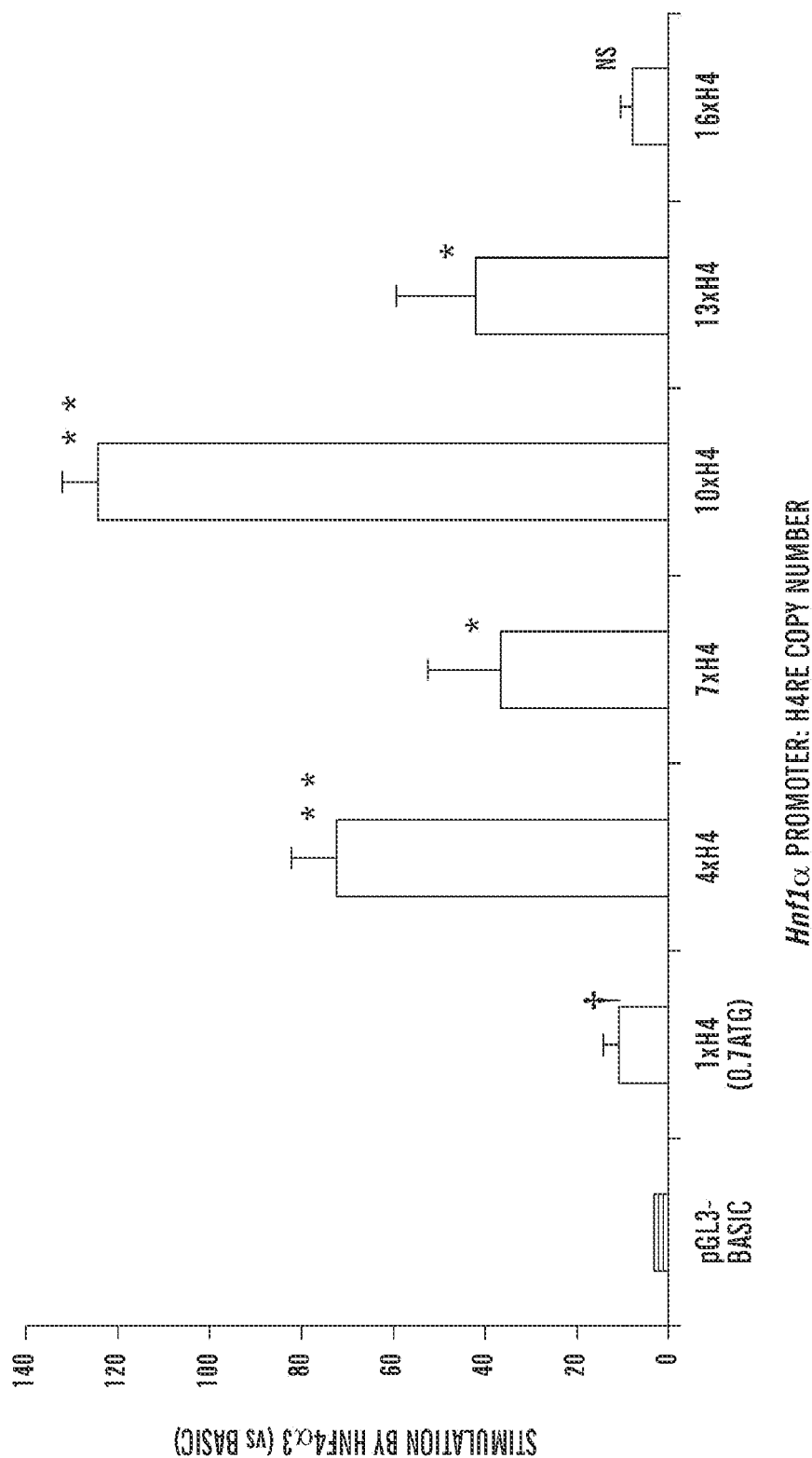
FIG. 1B shows the effect of increasing the number of adjacent H4REs on mHnf1α promoter activity in the reporter plasmid pGL3 transfected into HEK-293 cells.

The mHnf1α$^{0.7ATG}$ promoter, with a conserved H4RE 278 bp upstream of the ATG start codon (30), was modified by inserting up to five sets of three contiguous H4REs into the BlpI site 20 bp downstream of the native H4RE (FIG. 1A; FIG. 7B). The H4RE sequences were derived from the two human G6Pase gene elements (−236/−218 and −78/−60 from RefSeq No.: NM_000151) flanking the human HNF1B element (TCF2; −214/−196 from RefSeq NM_000458).

The multiple H4Res were inserted were separated by 9-15 bp which is the nucleotide spacing close to a single helical DNA turn of 10-11 bp (34,35). Promoter activities were assessed by transient transfection in HEK-293 cells with the indicated mHnf1α promoter reporters (200 ng) alone or in combination with the pcDNA-HNF4a3 expression vector (200 ng).

Activities were measured by DUAL LUCIFERASE®. Data are presented as fold stimulation over the promoter-less pGL3-Basic plasmid p<0.01 vs. Basic; *, p<0.05 vs. 1×H4RE; **, p<0.01 vs. 1×H4RE; NS, not significantly different from 1×H4RE (n=3; this experiment was repeated with nearly equivalent results). Each promoter had low basal activity, comparable to the blank pGL3-Basic. However, co-expression of HNF4α3 stimulated each promoter to a different degree (FIG. 1B). The native i$^{0.7ATG}$ promoter was stimulated 11-fold over baseline but the mHnf1α$^{4 \times H4RE}$ promoter was stimulated further to 72-fold. Incorporating additional H4RE motifs into a segment containing several H4Res enhanced some promoters but did not guarantee further increase in every promoter activity. For example, while the mHnf1α$^{10 \times H4RE}$ promoter was enhanced ~70% more than mHnf1α$^{4 \times H4RE}$ (124-fold), the mHnf1α$^{7 \times H4RE}$ and mHnf1α$^{3 \times H4RE}$ promoters had lower activity (only ~40-fold) and the mHnf1α$^{16 \times H4RE}$ promoter was less active than the native promoter (7-fold). These data indicate that promoter activity is not linearly dependent on the number of adjacent H4REs and indicate that boosting Hnf1α promoter activity with additional H4REs (spaced ~10 bp) has a limit. Thus we believe that the useful number of transcription factor repeats is 4-16, in some cases 4-10, in some cases 4, 5, 6 7, 8, 9, 10, 11, 12, 13, 14 or 15 repeats are useful. In some cases the 4-7 repeats provides the best enhancement. In some cases 4-6 and in some cases 4-5 repeats.

Figure 2A:
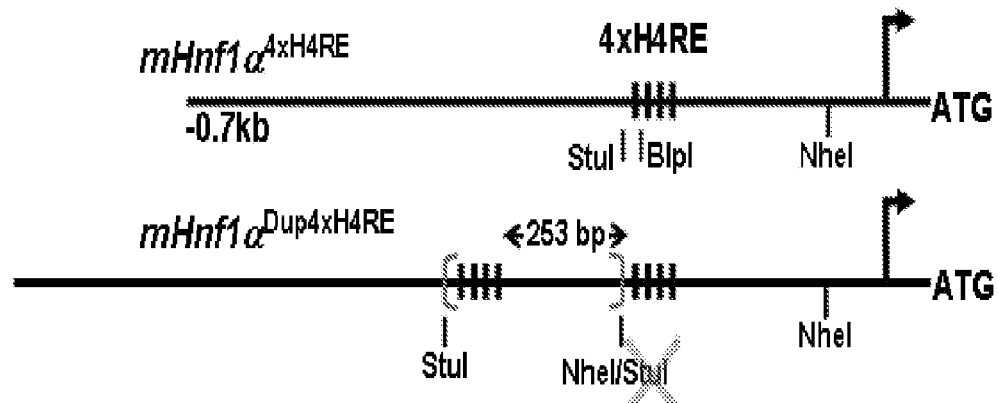
FIG. 2A shows the schematic of duplicating the StuI/NheI fragment containing the 4×H4RE motif to generate mHnf1α$^{Dup4\times H4RE}$. The transcription start site (arrow) corresponds to its position in the human promoter.
Figure 2B:
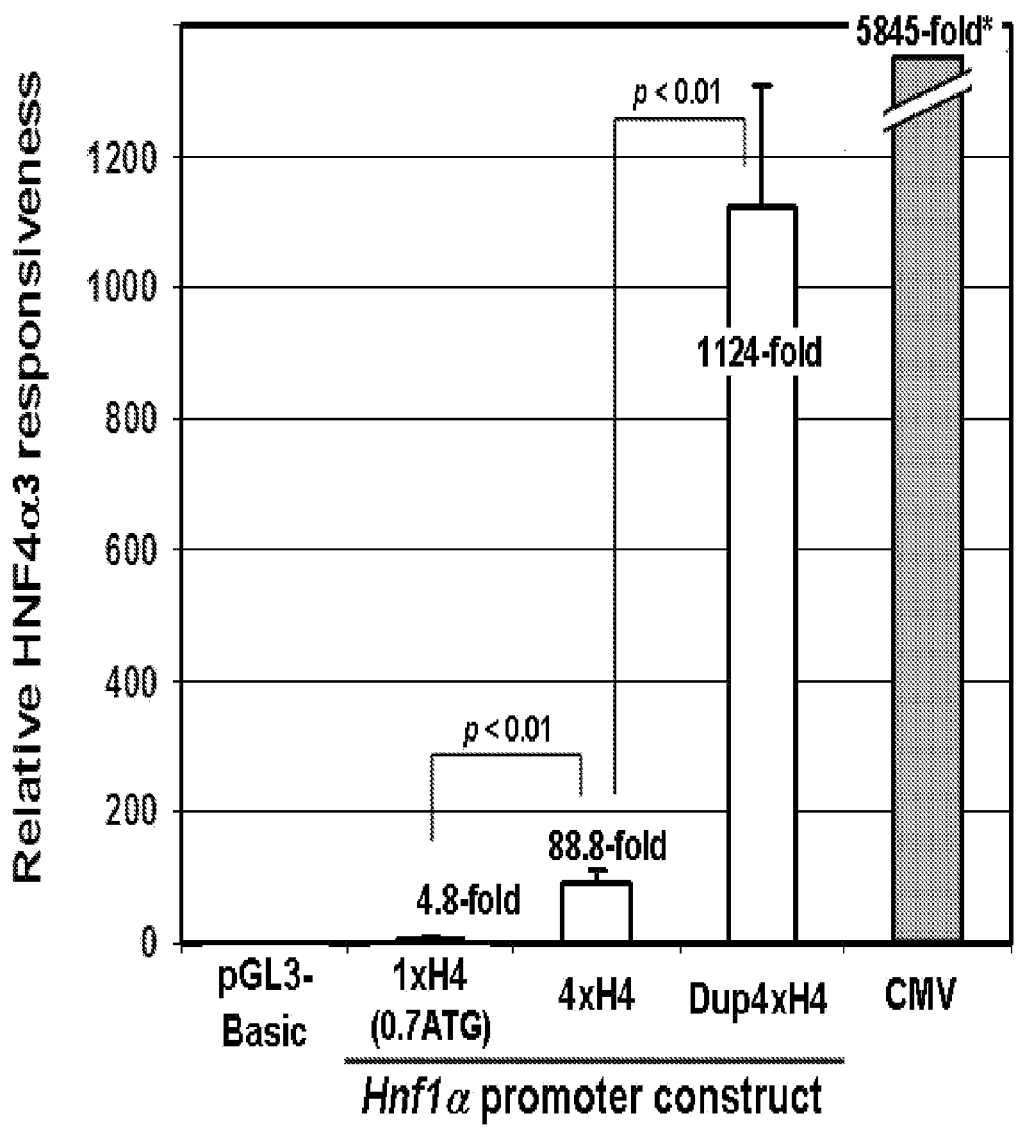
FIG. 2B shows the effect of duplicating the 370-bp mHnf1α$^{4\times H4RE}$ promoter fragment containing the 4×H4RE on promoter activity in the reporter plasmid pGL3 transfected into HEK-293 cells.

Insertion of Non-Adjacent 4×H4RE Motifs Considerably Enhanced Hnf1α Promoter Activity It is possible that the close assemblage of many similar cis elements could cause steric interference or otherwise obstruct the transcriptional machinery. To assess the effect of introducing additional H4REs into non-adjacent locations, the 370-bp StuI/NheI promoter fragment that contained the 4×H4RE motif (mHnf1 dup4×H4RE; FIG. 2A) was duplicated. This "duplicated" mHnf1α$^{Dup4\times H4RE}$ promoter was stimulated by >1100-fold, substantially more than for mHnf1α$^{0.7ATG}$ (~5-fold) or mHnf1α$^{4\times H4RE}$ (88-fold; FIG. 2B). HEK-293 cells were transiently transfected with the indicated mHnf1α promoter reporters (200 ng) alone or in combination with the pcDNA-HNF4a3 expression vector (200 ng). Data are presented as fold stimulation vs. pGL3-Basic (n=3; this experiment was repeated with nearly equivalent results). The numbers above the histograms indicate p values between activities. Constitutive activity of pGL3 containing the CMV immediate early promoter (200 ng) vs. pGL3-Basic is shown for comparison (gray bar; *, without pcDNA-HNF4α3). Stimulated mHnf1α$^{Dup4\times H4RE}$ promoter activity is ~20% that of the CMV promoter (FIG. 2B). Thus, separating two 4×H4RE motifs led to synergistic interaction rather an additive effect.

Two alternatives for the strong enhancement exhibited by mHnf1α$^{Dup4\times H4RE}$ were considered. First, the StuI/NheI fragment was tested for whether it contained elements other than the 4×H4RE that caused the enhancement. However, duplicating this fragment in the native mHnf1α$^{0.7ATG}$ promoter (mHnf1α$^{Dup1\times H4RE}$)did not detectably alter promoter activity. FIG. 7E shows the effects of StuI/NheI duplication in the native mHnf1α promoter: The StuI/NheI fragment was duplicated in the native promoter to generate mHnf1α$^{Dup1\times H4RE}$ The activity of this promoter was compared to the native promoter and 4×H4RE promoters in HEK-293 cells using Dual Luciferase.

Second, a putative Nkx-2.2 element (GCAAGTG, reverse orientation; −82/−88 with respect to NM_009327) 8 bp upstream of the H4RE was tested for whether its duplication contributed to the strong enhancement. A putative Nkx-2.2 site (consensus=GCAAGTG) is found in reverse orientation immediately upstream of the H4RE (box in FIG. 7F). This site in the mHnf1α$^{4\times H4RE}$ promoter and both sites in the mHnf1α$^{Dup4\times H4RE}$ promoter were mutated (reverse=TACCTAA). The activities of these promoters were compared to the native and wild-type 4×H4RE promoters in HEK-293 cells using Dual Luciferase. However, mutation of this Nkx-2.2 element in mHnf1α$^{4\times H4RE}$ or both elements in mHnf1α$^{Dup4\times H4RE}$ (to TACCTAA) more than doubled HNF4α3-stimulated promoter activities in HEK-293 cells (FIG. 7G). The removal of the Nkx-2.2 element did not abolished the enhance activity form the duplicated promoter. These results indicate that it is the 4×H4RE motif is the crucial feature in enhancing activity of the duplicated promoter.

Activity of the HNF4α-Dependent ApoC3 Promoter is Enhanced by Insertion of Non-Adjacent 4×H4RE Motifs To test whether non-adjacent 4×H4RE motifs could enhance another HNF4α-dependent promoter, the human ApoC3 promoter was examined, which has two H4REs (31) (reverse element at −70 bp and forward element at −690). The proximal response element was first inverted, and then both elements were converted to 4×H4RE motifs (ApoC3$^{Dup4\times H4RE/0.61}$), and deleted an internal 312-bp SacI fragment to reduce spacing by one-half (ApoC3$^{Dup4\times H4RE/0.30}$; FIG. 3A). HEK-293 cells were transiently transfected with the indicated ApoC3 promoter reporters (200 ng) alone or in combination with the pcDNA-HNF4a3 expression vector (200 ng). HNF4a3 stimulated the native promoter by ~56-fold and ApoC3$^{Dup4\times H4RE/0.61}$ by >1400-fold in HEK-293 cells (FIG. 3B). Stimulation of the ApoC3$^{Dup4\times H4RE/0.30}$ promoter, with the 4×H4REs in closer proximity, was lower but still substantial (~480-fold). These stimulated activities are ~24% and ~8% of CMV, respectively.

Increased Spacing Between 4×H4RE Motifs Reduced ApoC3 Promoter Activity

If favorable spacing between two 4×H4RE motifs is necessary to boost promoter activity, then altering the spacing should affect activity. To test this supposition, an unrelated, "non-functional" DNA (1,767-bp SacI fragment from human HNF1α cDNA NM_000545) was inserted between the 4×H4RE motifs to expand the spacing to 2.06 kb (FIG. 3A). This DNA fragment does not contain an H4RE and, as a cDNA, has lost the genomic context that may confer chromatin-like behavior. A series of promoters with lesser spacing were generated by deleting internal cDNA fragments and their activities were compared to the ApoC3 promoters with only native intervening DNA (FIG. 3B). Stimulation by HNF4α3 was significantly reduced by increasing the spacing to 2.06 kb (150-fold) or 1.31 kb (118-fold). Further reduction of spacing to 1.04 kb led to slightly higher stimulation (220-fold) and to 0.73 kb or 0.57 kb produced stimulations indistinguishable from the "uninserted" ApoC3$^{Dup4\times H4RE/0.61}$ promoter.

Activity of the HNF1-Dependent HNF4A P2 Promoter is Enhanced by Insertion of Non-Adjacent Multi-Copy H1RE Motifs (HNF1 Response Elements)

To determine whether incorporating non-adjacent multi-copy motifs of a different response element could enhance native promoter activity, the distal P2 promoter of the human HNF4A gene was modified. The P2 promoter, which is ~45 kb upstream of the proximal P1 promoter (36-38) and controls preferential expression of several HNF4α variants in the pancreas (39), is HNF1-dependent with a well-characterized H1RE at −0.17 kb (40). First, a 1.0-kb fragment (−1,013/−11) was cloned into pGL3-Basic. Then, a putative H1RE (−8.41 kb) was inserted at its 5-prime end to generate 840-bp spacing between the two H1REs (Hnf4α-P2$^{Dup1\times H1/0.84}$ FIG. 4A). Adding the second H1RE to P2 increased HNF1-responsiveness by about 30%.

Subsequently, both H1REs were converted to 4×H1RE motifs (Hnf4α-P2$^{Dup4\times H1/0.84}$). This promoter was further modified in several ways. First, 0.61 kb of DNA adjacent to the distal motif was deleted to create a 226-bp spacer (Hnf4α-P2$^{Dup4\times H1/0.23}$). This promoter was further modified by deleting the distal 4×H1RE, followed by sequential removal of H1REs from the downstream motif. Finally, an Hnf4α-P2$^{Dup2\times H1/0.27}$ promoter was constructed from Hnf4α-P2$^{Dup4\times H1/0.84}$ by deleting two H1REs and adjacent DNA from each motif. (B) Promoter activities: HEK-293 cells were transiently transfected with the indicated mHnf1α promoter reporters (200 ng) alone or in combination with the pcDNA-HNF4a3 expression vector (200 ng).

In the first set of modifications, both H1REs were converted to 4×H1RE motifs (HNF4A-P2$^{Dup4\times H1RE/0.84}$) and then the spacing between them was reduced to 0.23 kb by deleting 0.61 kb DNA downstream of the distal 4×H1RE (HNF4A-P2$^{Dup4\times H1RE/0.23}$). HNF1α stimulated the P2$^{Dup4\times H1RE/0.84}$ promoter ~180-fold, about 7 times more than the native promoter (26-fold; ~3% vs. CMV), and the P2$^{Dup4 \times H1RE/0.23}$ promoter by almost 500-fold (FIG. 4B; ~8% vs. CMV).

This result is consistent with the notion that activity increases when spacing is reduced to ~700 bp or less, as observed with the ApoC3 promoter.

In the second set of modifications, the impact of H1RE number and spacing on activity were explored. Deletion of the distal 4×H1RE motif essentially abolished the enhanced activity (to 38-fold stimulation). However, reduction of the remaining 4×H1RE motif to either 3× or 2× motifs re-activated this promoter to stimulations of ~180- and ~140-fold, respectively. On the other hand, construction of a promoter with two 2×H1RE motifs spaced 0.27 kb apart also produced remarkably high stimulation (~270-fold).

Accordingly, one can create enhanced promoters by multiplying segments of at least 2 transcription factor response elements, wherein the transcription factor response elements are 9-15 bp apart, and wherein the segments are about 200-700 base pairs apart. Based on our experiments, to obtain the optimal enhancement, the transcription factor elements are organized in forward orientation with respect to the transcription start site.

In contrast to the HNF4α-responsive promoters, most modified HNF4A P2 promoters exhibited modest constitutive activity in HEK-293 cells, i.e. independent of co-expressed HNF1α. This constitutive activity was 4-fold for the native promoter and ranged from 1.5-fold for the single 4×H1RE promoter to a high of ~30-fold for the duplicate 2×H1RE promoter. Nevertheless, the consistently high induction ratios with HNF1α (9.5 to >40) indicate that responsiveness to this factor was retained.

Figure 5A:
FIG. 5A shows the schematic diagram of the coding sequence of human HNF1α fused to the augmented mHnf1α promoter to form the mHnf1α$^{Dup4\times H4RE}$/HNF1α minigene cassette (upper) and the protein expression from the augmented promoter (lower).
Figure 5A:
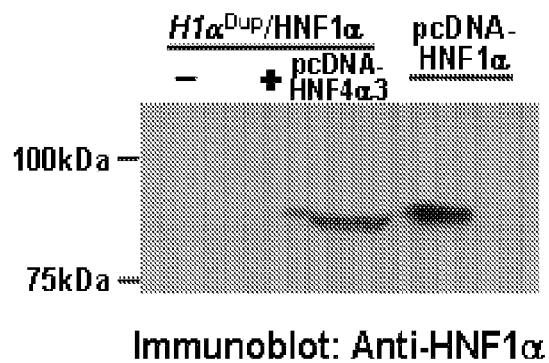
Figure 5B:
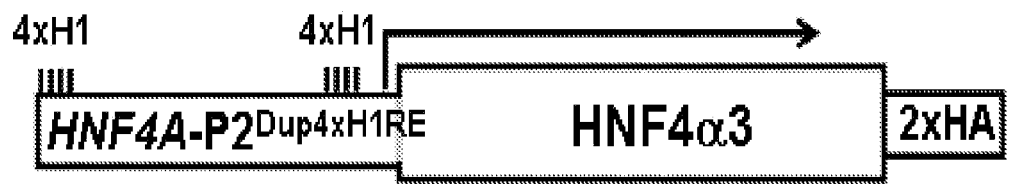
FIG. 5B shows the schematic diagram of the coding sequence of rat HNF4α3 that is HA-tagged at the C-terminus and then fused to the augmented P2 promoter to form the HNF4A-P2$^{Dup4\times H4RE}$/HNF4α3$^{HA}$ minigene cassette (upper) and the protein expression from the augmented promoter (lower).
Figure 5B:
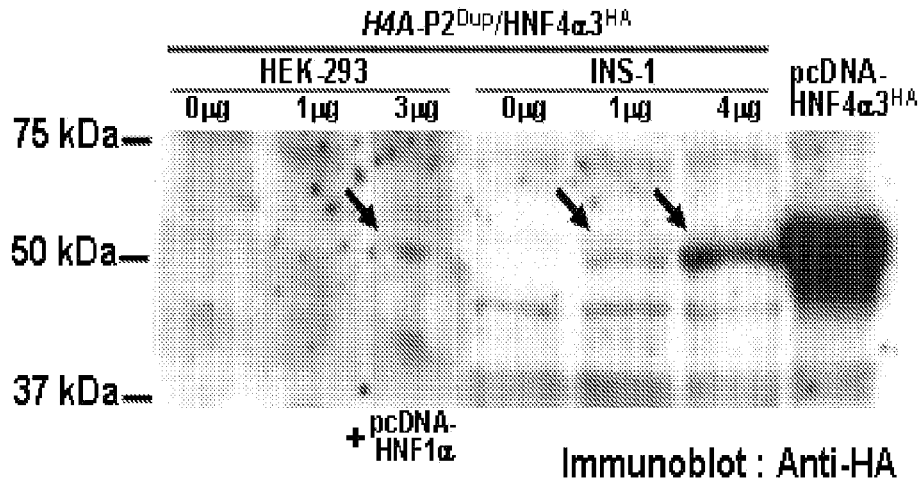

Augmented Promoters Generate Detectable Amounts of Functional Transcription Factors To test whether augmented promoters are sufficiently active to generate detectable protein levels with measurable activities, each promoters was fused to coding sequences of their cognate transcription factors: human HNF1α to mHnf1α$^{Dup4 \times H4RE}$ and HA-tagged rat HNF4a3 (HNF4a3$^{HA}$) to HNF4A-P2$^{Dup4 \times H1RE}$ (FIGS. 5A & 5B, upper). HEK-293 cells were transiently transfected with the mHnf1α$^{Dup4 \times H4RE}$/HNF1a plasmid with or without the pcDNA-rHNF4a3 expression vector. Whole cell protein was extracted 48 h later to assess HNF1a expression by immunoblotting (pcDNA-HNF1a, positive control). For HNF4A-P2$^{Dup4 \times H4RE}$/HNF4α3$^{HA}$ gene cassette, the coding sequence of rat HNF4a3 was fused to the augmented P2 promoter. HEK-293 or INS-1 cells were transiently transfected with the HNF4A-P2$^{Dup4 \times H4RE}$/HNF4α3$^{HA}$ plasmid and, where indicated, the pcDNA-HNF1a expression vector. Whole cell protein was extracted 48 h later to assess HNF4a3HA expression by immunoblotting for the HA tag (pcDNA-HNF4a3$^{HA}$, positive control). The numbers above the histogram indicate p values between activities.

The HA tag enabled detection of ectopic HNF4a3 in the presence of endogenous or transiently expressed HNF4α3. Transient introduction of the HNF1α minigene into HEK-293 cells led to HNF4α-dependent production of the HNF1α protein (FIG. 5A, lower). Similarly, the HNF4α3$^{HA}$ minigene exhibited HNF1α-dependent HNF4α3$^{HA}$ expression in HEK-293 cells (using its HA epitope tag; FIG. 5B, lower; arrow). The augmented P2 promoter is constitutively active in INS-1 cells (see below) and, consequently, the HNF4α3$^{HA}$ minigene produced protein without exogenous HNF1α expression FIG. 5B, lower; arrows).

Figure 5C:
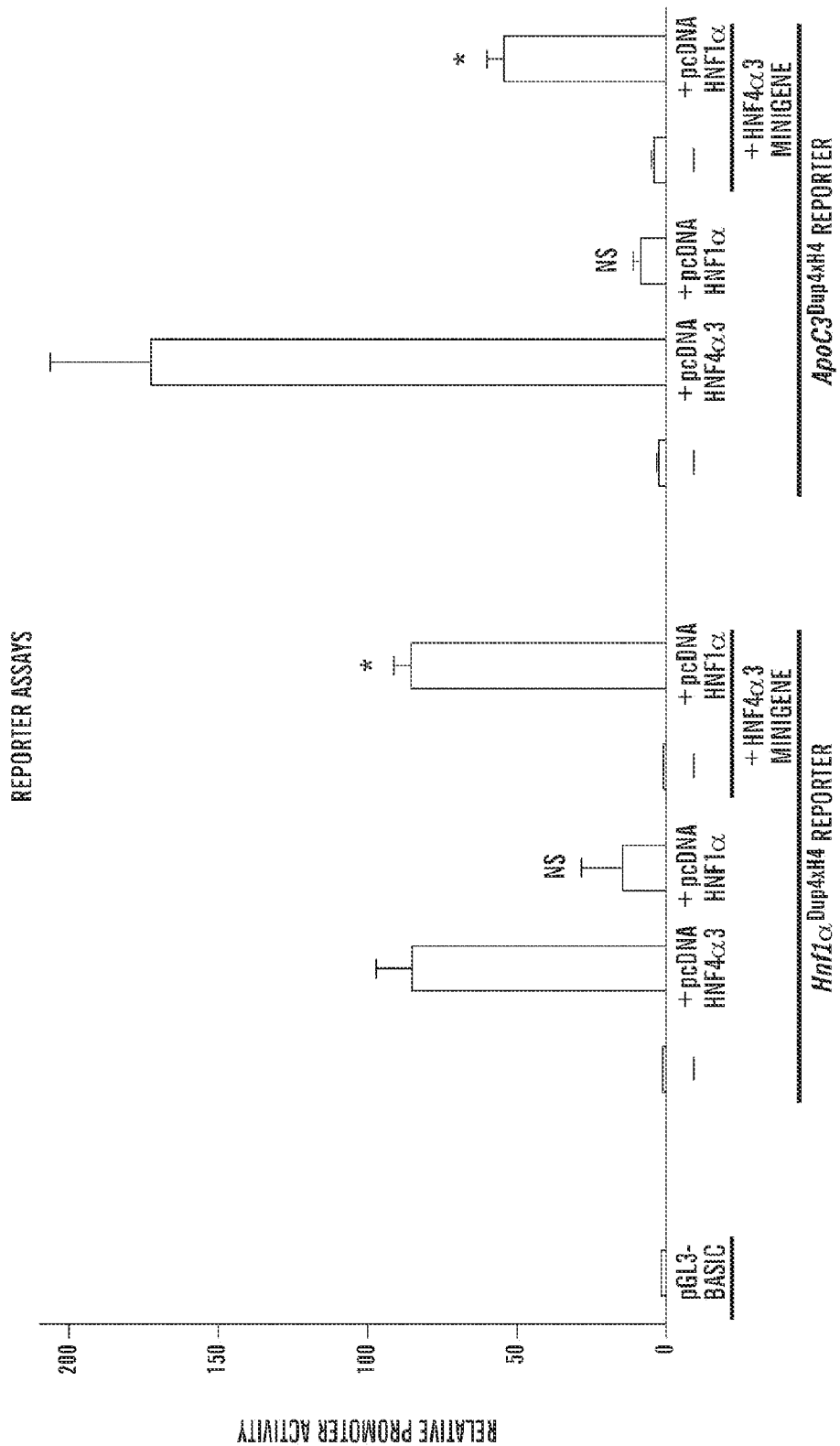
FIG. 5C shows the reporter assay data of HEK-293 cells that were transiently transfected with the indicated combinations of reporter plasmid (200 ng), expression plasmid (100 ng), and cognate mini gene cassette (100 ng). Data are presented as fold stimulation vs. pGL3-Basic (n=3; NS, not significantly different from reporter plasmid alone; *, p<0.005 vs. reporter plasmid either alone or with the HNF1α minigene inducer). This experiment was repeated with nearly equivalent results.

To test whether functional levels of HNF1α and HNF4α3$^{HA}$ are expressed, the activation of reporters was examined (FIG. 5C). HEK-293 cells were transiently transfected with the indicated combinations of reporter plasmid (150 ng), expression plasmid (100 ng), and cognate gene cassette (150 ng). Data are presented as fold stimulation vs. pGL3-Basic (n=3; this experiment was repeated with nearly equivalent results). Brackets indicate p values between activities.

To test whether the expressed HNF1α and HNF4α3HA are functional, their abilities to activate reporters for their target promoters in HEK-293 cells were examined. As previously shown, the mHnf1α$^{Dup4 \times H4RE}$ reporter was markedly stimulated by HNF4α3 (FIG. 5C). In contrast, HNF1α produced a modest but insignificant stimulation while the HNF4A-P2$^{Dup4 \times H1RE}$/HNF4α3$^{HA}$ gene cassette had no effect. However, the mHnf1α$^{Dup4 \times H4RE}$ promoter was significantly stimulated by the combination of HNF1α and the HNF4A-P2$^{Dup4 \times H1RE}$/HNF4α3$^{HA}$ gene cassette. Similarly, this combination also significantly stimulated the ApoC3$^{Dup4 \times H4RE/0.61}$ promoter (FIG. 5C). On the other hand, the combination of HNF4α3 and the mHnf1α$^{Dup4 \times H4RE}$/HNF1a gene cassette did not appreciably stimulate the HNF4A-P2$^{Dup4 \times H1RE}$ promoter (not shown) but the possibility that HNF4α3 inhibited this promoter was not explicitly ruled out.

Enhanced Promoter Activities are also Observed in Rat INS-1 β cells

The augmented promoters were developed based on their activities in heterologous HEK-293 cells. Thus, it was important to assess how modified promoters behaved in β cell line that normally expresses HNF1α and HNF4α. Rat INS-1 β cells were chosen because they exhibit glucose-dependent insulin secretion (29) and can offer a model for enhancing this property using augmented promoters to express β-cell transcription factors.

To assess activities of modified promoters in a β cell line that normally expresses HNF1α and HNF4α, the promoters were tested in rat INS-1 β cells. Reporter plasmids were transiently transfected into INS-1 cells with or without co-transfected pcDNA-HNF4a3 expression vector. Normalized luciferase activities are expressed relative to that of blank pGL3-Basic. Previously, it was found that the mHnf1α promoter is not constitutively active in INS-1 cells, but is but is responsive to ectopically increased expression of HNF4α (30). Likewise, none of the modified mHnf1α promoters exhibited constitutive activity in these cells (activity comparable to blank pGL3-Basic) but each was stimulated by increased HNF4α3 expression.

Figure 6A:
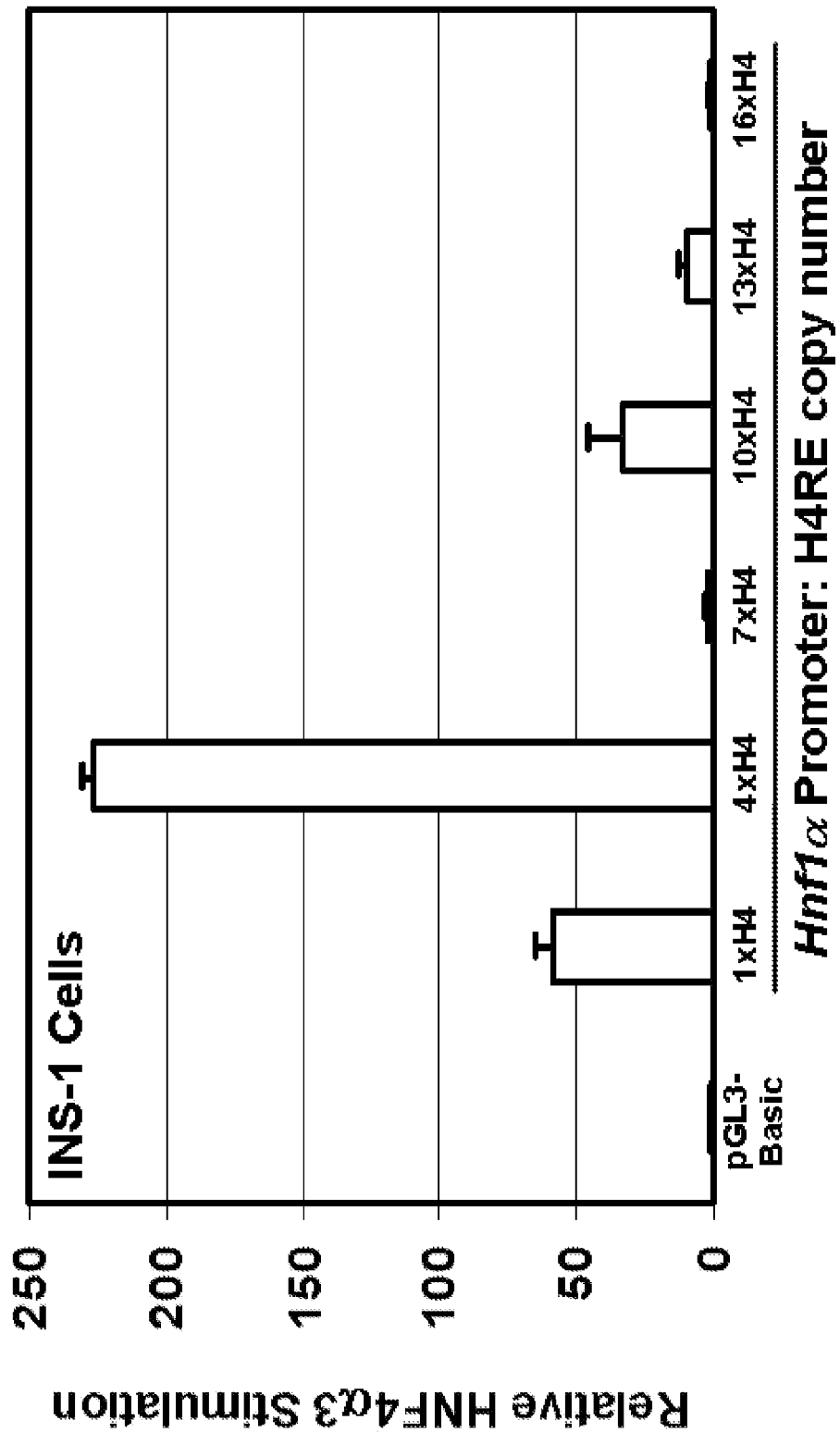
FIG. 6A shows the effect of H4RE copy number in the mHnf1α promoter in rat INS-1 β cells upon HNF4α3 stimulation (n=3).
Figure 6B:
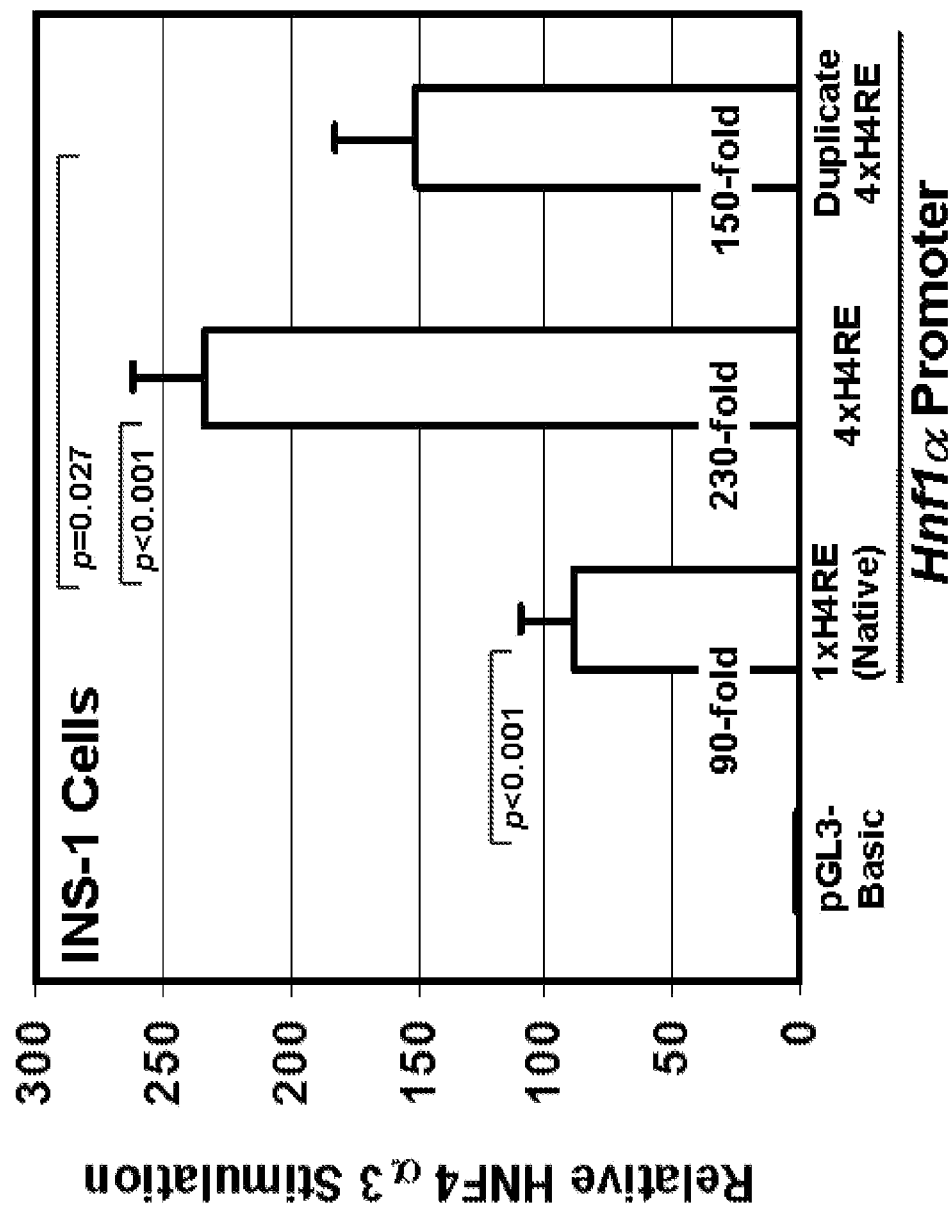
FIG. 6B shows the effect of duplicating the 4×H4RE in the mHnf1α promoter in rat INS-1 β cells upon HNF4α3 stimulation (n=6).

However, increasing the number of H4REs in the mHnf1α promoter (FIG. 6A) produced results similar to those observed in HEK-293 cells (FIG. 1B), although promoters with the highest H4RE copy number were relatively less active in INS-1 cells than in the heterologous HEK-293 cells. Moreover, duplicating the 4×H4RE motif somewhat diminished promoter activity in INS-1 cells (FIG. 6B) unlike the effect in HEK-293 cells (FIG. 2B).

The behavior of the ApoC3 promoters (FIG. 6C) mirrored that in HEK-293 cells (FIG. 3B) with the exception that the ApoC3$^{Dup4 \times H4RE/0.30}$ promoter was more active than ApoC3$^{Dup4 \times H4RE/0.61}$.

Figure 6D:
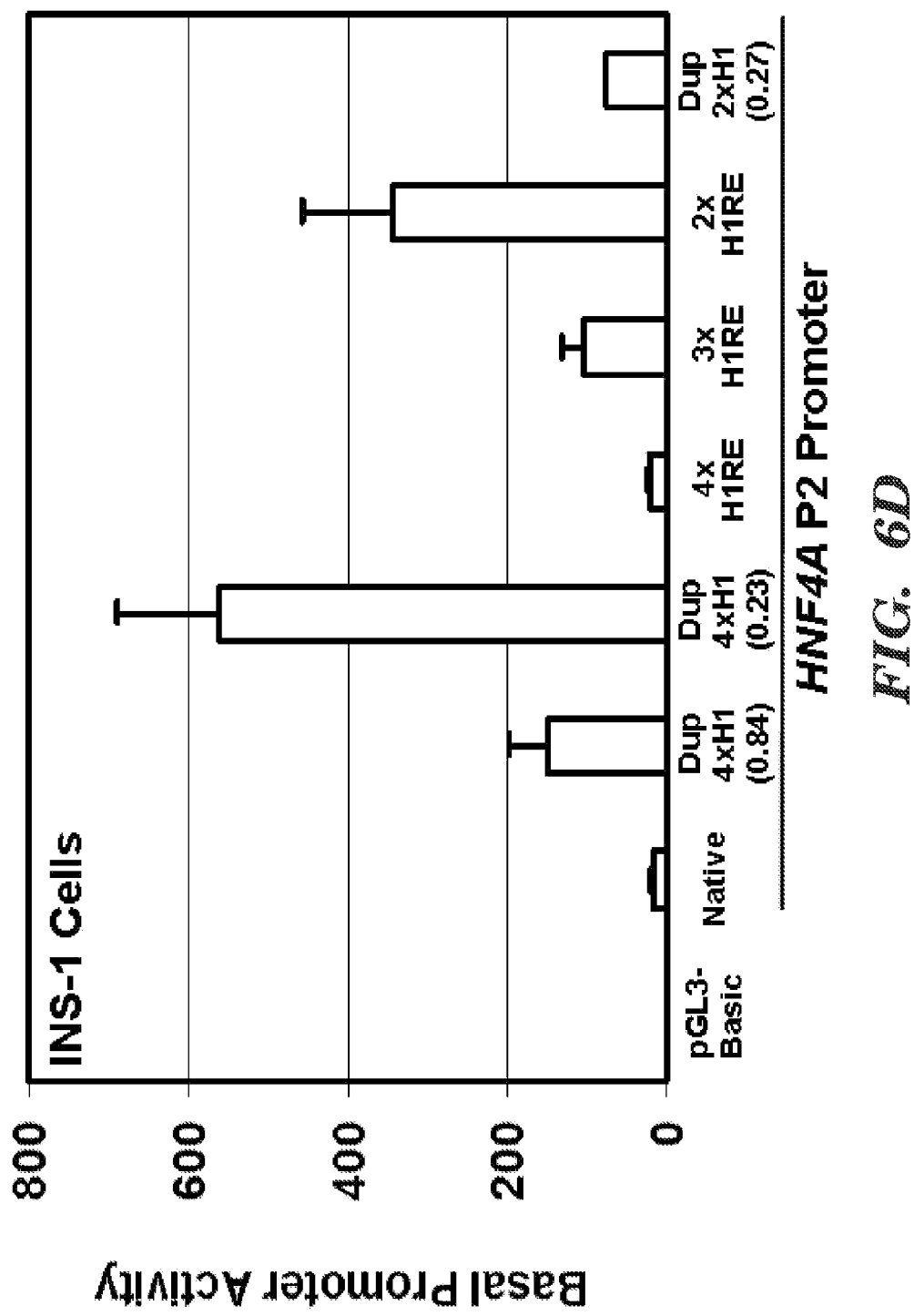
FIG. 6D shows the effect of H1RE copy number and/or duplicating the 4×H1RE in the HNF4A P2 promoter in rat INS-1 β cells upon HNF1 stimulation (n=6).

In contrast, the HNF4A P2 promoters were constitutively active in INS-1 cells (FIG. 6D). These constitutive activities cells were similar to HNF4α-induced activities in HEK-293 cells (FIG. 4B) except for the low activity of the HNF4A-P2$^{Dup2 \times H1RE/0.27}$ promoter. Co-expression of HNF4c modestly increased promoter activities from 10% to 3-fold except for HNF4A-P2$^{Dup4\times H1RE/0.84}$, which was inhibited by 50%.

DISCUSSION

The inventors have developed a strategy to substantially exponentially enhance native promoter activity by amplifying responsiveness to a crucial transcription factor and particularly by using spacers of about 200-700 bp between groups of multi-copy REs.

While tandem RE arrays have been used, under the premise that adjacent elements cooperate in activating transcription (41), their ability to increase promoter activity may be inherently limited.

The inventors showed that providing a spacer DNA between groups of multiple REs is very effective in boosting native promoter activity. Specifically, HNF4c induction was increased >200-fold over the native mouse Hnf1α promoter by engineering a 4×H4RE motif, then duplicating the fragment containing this motif to obtain duplicate motifs 0.25 kb apart (See FIG. 2B).

Moreover, the enhanced promoter could drive inducible readily detectable protein expression following transient transfection (See FIG. 5).

When the strategy was applied to the HNF4α-dependent ApoC3 promoter, taking advantage of its two H4REs spaced 0.61 kb apart, activity was also substantially boosted.

In addition, extension of the "spacer strategy" to the HNF1α-dependent HNF4A P2 promoter also provided similar results, indicating the applicability to a wide range of genes and REs.

Moreover, the enhanced Hnf1α and HNF4A P2 promoters both drove readily detectable expression of cognate proteins, of which HNF1α was capable of activating target promoters. Accordingly, the same strategy can be applied to many native gene promoters could be modified for use in gene therapy.

Multiple copies of response elements have been incorporated into promoters to create more sensitive reporters and expression vectors. For instance, the 100-fold inducibility of the β-catenin reporter pSuperTopFlash (19) makes it an excellent reporter but only β-catenin phosphorylation mutants enable the ~1000-fold inducibility necessary to achieve physiological levels. Thus, even with this highly potent non-native promoter, the normal enhancement level is still far short of that necessary for effective gene therapy.

The inventors tested whether a sufficient number of H4REs could be inserted into the native Hnf1α promoter to activate it beyond the generally observed range of 10- to 50-fold. However, at least for closely-arrayed H4REs in the context of the Hnf1α promoter, enhancement reached an apparent plateau with the 10×H4RE promoter and additional elements were ultimately counterproductive. In contrast, separating two 4×H4RE motifs by several hundred base pairs, preferably not exceeding 700 bp led to synergistic activation. The ineffectiveness of duplicating the native 1×H4RE fragment to create duplicate 1×H4REs separated by the same DNA demonstrated that a repeat of H4Res, namely, 4×H4RE motif was important to the enhancement. This conclusion was further supported by exclusion of the nearby Nkx-2.2 site as the active component in the duplication.

Accordingly, the data indicate that the introduction of a DNA spacer between two multi-copy motifs or segments was the major factor in augmenting promoter activity and was distinctly superior to introducing additional RE copies alone, based on number of fold increase in reporter gene expression.

This is the first report to describe enhancement of native promoter activity to the order of 1000-fold over baseline (i.e. activity of the blank reporter or augmented promoter without stimulation) as well to reveal the exceptional ability of spacer DNA to amplify response element multimers.

The results with the ApoC3 and HNF4A P2 promoters support our conclusion that spacing of several hundred bp, but preferably not exceeding 700 bp between multi-copy motifs is optimum. For ApoC3, spacing of 0.61 kb with native promoter DNA led to the highest activity while deleting half the spacer reduced activity to about one-third. In the other direction, separating the 4×H4RE motifs by >2.0 kb markedly diminished the spacer-dependent stimulation. Much of the lost activity was regained when ~0.6-kb spacing was restored. For HNF4A P2, activity increased markedly when the native 0.84-kb spacer was reduced to 0.23 kb. The similar result obtained with the three different promoters is compelling evidence for a major role of multi-copy RE motif spacing in boosting promoter activities.

Different H1RE motif configurations produced large changes in HNF4A P2 promoter activity. Two or three H1REs in a single motif conferred greater activity than either 4×H1RE or 1×H1RE. In fact, 4×H1RE promoter activity was as low as the 1×H1RE promoter. However, when four H1REs were arranged as duplicate 2×H1RE motifs with 0.27-kb spacing, promoter activity was significantly higher than the single, contiguous 4×H1RE arrangement.

The activities of modified promoters in INS-1 cells provide further insights. With only few exceptions, relative promoter activities were largely the same in this 13 cell line as in HEK-293 cells co-transfected with HNF4c6. mHnf1α promoter constructs with more than the four adjacent elements as in the 4×H4RE promoter were weaker than the native promoter. In addition, the mHnf1α$^{Dup4\times H4RE}$ promoter with its 8 H4REs was also less active than the single-motif 4×H4RE promoter. These results may reflect the presence of negative regulatory factors in INS-1 cells that keep the modified promoters in check to some degree. Also, the active mHnf1α promoter constructs remained dependent on co-transfected HNF4α3 in INS-1 cells. This result indicates that promoter behavior was amplified by the modifications and not otherwise altered noticeably. For ApoC3, the ApoC3$^{Dup4\times H4RE/0.61}$ promoter with its native spacing was about half as potent in INS-1 cells as in HEK-293 cells while the ApoC3$^{Dup4\times H4RE/0.30}$ promoter was markedly more potent. These differences could reflect an ApoC3 promoter element inhibitory in INS-1 cells because ApoC3 expression is normally restricted to liver. Finally, it was found that the modified HNF4A P2 constructs had robust basal activities in INS-1 cells. This result is also consistent with the amplification of native promoter activity.

The mHnf1α$^{Dup4\times H4RE}$ and HNF4A-P2$^{Dup4\times H1RE}$ promoters in the luciferase reporter plasmid exhibited inducible activity ~20% and ~8% obtainable with the strong, constitutive CMV promoter, respectively. Moreover, active HNF1a and HNF4α3$^{H4}$ proteins were expressed from these promoters and this demonstrated that both gene cassettes can function effectively in gene expression. Furthermore, production of readily-detectible HNF4α3$^{H4}$ in INS-1 cells relying on constitutive HNF4A-P2$^{Dup4\times H1RE}$ promoter activity indicates that gene expression modules can be designed with native promoters for a variety of cell types.

The references cited herein and throughout the specification are incorporated herein by reference.

REFERENCES

1. Okita, K., Ichisaka, T. and Yamanaka, S. (2007) Generation of germline-competent induced pluripotent stem cells. Nature, 448:313-317.

2. Yamada, K., Tsukahara, T., Yoshino, K., Kojima, K., Agawa, H., Yamashita, Y., Amano, Y., Hatta, M., Matsuzaki, Y., Kurotori, N. et al. (2009) Identification of a high incidence region for retroviral vector integration near exon 1 of the LMO2 locus. Retrovirology, 6:79.
3. Nam, C. H. and Rabbitts, T. H. (2006) The role of LMO2 in development and in T cell leukemia after chromosomal translocation or retroviral insertion. Mol. Ther., 13:15-25.
4. Gossen, M. and Bujard, H. (2002) Studying gene function in eukaryotes by conditional gene inactivation. Annu. Rev. Genet., 36:153-173.
5. Jackson, D. A. (2003) The principles of nuclear structure. Chromosome Res., 11:387-401.
6. West, A. G. and Fraser, P. (2005) Remote control of gene transcription. Hum. Mol. Genet., 14 (Spec No 1):R101-111.
7. Grosveld, F., van Assendelft, G. B., Greaves, D. R. and Kollias, G. (1987) Position-independent, high-level expression of the human beta-globin gene in transgenic mice. Cell, 51:975-985.
8. Fraser, P. and Grosveld, F. (1998) Locus control regions, chromatin activation and transcription. Curr. Opin. Cell Biol., 10:361-365.
9. Li, Q., Peterson, K. R., Fang, X. and Stamatoyannopoulos, G. (2002) Locus control regions. Blood, 100:3077-3086.
10. Wang, Y., Yu, L. and Geller, A. I. (1999) Diverse stabilities of expression in the rat brain from different cellular promoters in a helper virus-free herpes simplex virus type 1 vector system. Hum. Gene Ther., 10:1763-1771.
11. Hwang, D. Y., Carlezon, W. A., Jr., Isacson, O. and Kim, K. S. (2001) A high-efficiency synthetic promoter that drives transgene expression selectively in noradrenergic neurons. Hum. Gene Ther., 12:1731-1740.
12. German, M. S., Moss, L. G., Wang, J. and Rutter, W. J. (1992) The insulin and islet amyloid polypeptide genes contain similar cell-specific promoter elements that bind identical beta-cell nuclear complexes. Mol. Cell Biol., 12:1777-1788.
13. Sander, M., Griffen, S. C., Huang, J. and German, M. S. (1998) A novel glucose-responsive element in the human insulin gene functions uniquely in primary cultured islets. Proc. Natl. Acad. Sci. U.S.A., 95:11572-11577.
14. Zaret, K. S., DiPersio, C. M., Jackson, D. A., Montigny, W. J. and Weinstat, D. L. (1988) Conditional enhancement of liver-specific gene transcription. Proc. Natl. Acad. Sci. U.S.A., 85: 9076-9080.
15. Wang, X., Kong, L., Zhang, G. R., Sun, M. and Geller, A. I. (2004) A preproenkephalin-neurofilament chimeric promoter in a helper virus-free herpes simplex virus vector enhances long-term expression in the rat striatum. Neurobiol. Dis., 16:596-603.
16. Shaw, K. L., Pais, E., Ge, S., Hardee, C., Skelton, D., Hollis, R. P., Crooks, G. M. and Kohn, D. B. (2009) Lentiviral vectors with amplified b cell-specific gene expression. Gene Ther. 16:998-1008.
17. Venter, M. and Warnich, L. (2009) In silico promoters: modelling of cis-regulatory context facilitates target predictio. J. Cell Mol. Med., 13:270-278.
18. Kaluz, S., Kaluzova, M. and Stanbridge, E. J. (2008) Rational design of minimal hypoxia-inducible enhancers. Biochem. Biophys. Res. Commun., 370:613-618.
19. Veeman, M. T., Slusarski, D. C., Kaykas, A., Louie, S. H. and Moon, R. T. (2003) Zebrafish prickle, a modulator of noncanonical Wnt/Fz signaling, regulates gastrulation movements. Curr. Biol., 13:680-685.
20. Miura, N. and Tanaka, K. (1993) Analysis of the rat hepatocyte nuclear factor (HNF) 1 gene promoter: synergistic activation by HNF4 and HNF1 proteins. Nucleic Acids Res., 21:3731-3736.
21. Piaggio, G., Tomei, L., Toniatti, C., De Francesco, R., Gerstner, J. and Cortese, R. (1994) LFB1/HNF1 acts as a repressor of its own transcription. Nucleic Acids Res., 22:4284-4290.
22. Gragnoli, C., Lindner, T., Cockburn, B. N., Kaisaki, P. J., Gragnoli, F., Marozzi, G. and Bell, G. I. (1997) Maturity-onset diabetes of the young due to a mutation in the hepatocyte nuclear factor-4a binding site in the promoter of the hepatocyte nuclear factor-1a gene. Diabetes, 46:1648-1651.
23. Jung, D. and Kullak-Ublick, G. A. (2003) Hepatocyte nuclear factor 1a: a key mediator of the effect of bile acids on gene expression. Hepatology, 37:622-631.
24. Yamagata, K., Oda, N., Kaisaki, P. J., Menzel, S., Furuta, H., Vaxillaire, M., Southam, L., Cox, R. D., Lathrop, G. M., Boriraj, V. V. et al. (1996) Mutations in the hepatocyte nuclear factor-1a gene in maturity-onset diabetes of the young (MODY3). Nature, 384:455-458.
25. Yamagata, K., Furuta, H., Oda, N., Kaisaki, P. J., Menzel, S., Cox, N. J., Fajans, S. S., Signorini, S., Stoffel, M. and Bell, G. I. (1996) Mutations in the hepatocyte nuclear factor-4a gene in maturity-onset diabetes of the young (MODY1). Nature, 384:458-460.
26. Servitja, J. M. and Ferrer, J. (2004) Transcriptional networks controlling pancreatic development and b cell function. Diabetologia, 47:597-613.
27. Ferrer, J. (2002) A genetic switch in pancreatic b-cells: implications for differentiation and haploinsufficiency. Diabetes, 51:2355-2362.
28. Ladias, J. A., Hadzopoulou-Cladaras, M., Kardassis, D., Cardot, P., Cheng, J., Zannis, V. and Cladaras, C. (1992) Transcriptional regulation of human apolipoprotein genes ApoB, ApoCIII, and ApoAII by members of the steroid hormone receptor superfamily HNF-4, ARP-1, EAR-2, and EAR-3. J. Biol. Chem., 267:15849-15860.
29. Asfari, M., Janjic, D., Meda, P., Li, G., Halban, P. A. and Wollheim, C. B. (1992) Establishment of 2-mercaptoethanol-dependent differentiated insulin-secreting cell lines. Endocrinology, 130:167-178.
30. Huang, J., Karakucuk, V., Levitsky, L. L. and Rhoads, D. B. (2008) Expression of HNF4a variants in pancreatic islets and Ins-1 b cells. Diabetes Metab. Res. Rev., 24:533-543.
31. Ogami, K., Hadzopoulou-Cladaras, M., Cladaras, C. and Zannis, V. I. (1990) Promoter elements and factors required for hepatic and intestinal transcription of the human ApoCIII gene. J. Biol. Chem., 265:9808-9815.
32. Huang, J., Levitsky, L. L. and Rhoads, D. B. (2009) Novel P2 promoter-derived HNF4a isoforms with different N-terminus generated by alternate exon insertion. Exp. Cell Res., 315:1200-1211.
33. Yang, F., Agulian, T., Sudati, J. E., Rhoads, D. B. and Levitsky, L. L. (2004) Developmental regulation of galactokinase in suckling mouse liver by the Egr-1 transcription factor. Pediatr. Res., 55:822-829.
34. Wang, J. C. (1979) Helical repeat of DNA in solution. Proc. Natl. Acad. Sci. U.S.A., 76: 200-203.
35. Larsson, E., Lindahl, P. and Mostad, P. (2007) HeliCis: a DNA motif discovery tool for colocalized motif pairs with periodic spacing. BMC Bioinformatics, 8:418.
36. Nakhei, H., Lingott, A., Lemm, I. and Ryffel, G. U. (1998) An alternative splice variant of the tissue specific transcrip- 37. Thomas, H., Jaschkowitz, K., Bulman, M., Frayling, T. M., Mitchell, S. M., Roosen, S., Lingott-Frieg, A., Tack, C. J., Ellard, S., Ryffel, G. U. et al. (2001) A distant upstream promoter of the HNF-4a gene connects the transcription factors involved in maturity-onset diabetes of the young. Hum. Mol. Genet., 10:2089-2097.
38. Tones-Padilla, M. E. and Weiss, M. C. (2003) Effects of interactions of hepatocyte nuclear factor 4a isoforms with coactivators and corepressors are promoter-specific. FEBS Lett., 539:19-23.
39. Boj, S. F., Parrizas, M., Maestro, M. A. and Ferrer, J. (2001) A transcription factor regulatory circuit in differentiated pancreatic cells. Proc. Natl. Acad. Sci. U.S.A., 98:14481-14486.
40. Briancon, N., Bailly, A., Clotman, F., Jacquemin, P., Lemaigre, F. P. and Weiss, M. C. (2004) Expression of the a7 isoform of hepatocyte nuclear factor (HNF) 4 is activated by HNF6/OC-2 and HNF1 and repressed by HNF4a1 in the liver. J. Biol. Chem., 279:33398-33408.
41. Ptashne, M. (1988) How eukaryotic transcriptional activators work. Nature, 335:683-689.
42. Jensen, P. R. and Hammer, K. (1998) The sequence of spacers between the consensus sequences modulates the strength of prokaryotic promoters. Appl. Environ. Microbiol., 64, 82-87.
43. Solem, C. and Jensen, P. R. (2002) Modulation of gene expression made easy. Appl. Environ. Microbiol., 68, 2397-2403.
44. Gupta, S., Dennis, J., Thurman, R. E., Kingston, R., Stamatoyannopoulos, J. A. and Noble, W. S. (2008) Predicting human nucleosome occupancy from primary sequence. PLoS Comput. Biol., 4:e1000134.
45. Kuhn, R. M., Karolchik, D., Zweig, A. S., Wang, T., Smith, K. E., Rosenbloom, K. R., Rhead, B., Raney, B. J., Pohl, A., Pheasant, M. et al. (2009) The UCSC Genome Browser Database: update 2009. Nucleic Acids Res., 37:D755-761.

TABLE 1

| Mammalian native promoters | Gene | Native RE used by native promoter | native transcription factor binding to RE | native transcription factor type | Cells targeted for expression by modified promoter (in nature, e.g. in gene therapy) | Gene Reference No. and location of the RE |
|---|---|---|---|---|---|---|
| Hepatocyte Nuclear Factor 4α P2 (distal) | Hepatocyte Nuclear Factor 4α (HNF4A) | Hepatocyte Nuclear Factor 1 RE (H1RE) | Hepatocyte Nuclear Factor 1 alpha (HNF1α) | homeo-domain protein | pancreatic β cells, intestinal mucosal cells, hepatocytes | NM_175914 (Chr20: 42,984,441-43,058,311); H1RE at −152 (and putative H1RE at −8 kb moved to −1.0 or 0.23 kb) |
| Hepatocyte Nuclear Factor 1 alpha | Hepatocyte Nuclear Factor 1 alpha (Hnf1a/Tcf) | Hepatocyte Nuclear Factor 4 RE (H4RE) | Hepatocyte Nuclear Factor 4 alpha (HNF4α) | nuclear hormone receptor | pancreatic β cells, intestinal mucosal cells, hepatocytes | NM_009723 (Mouse Chr5: 115,398,370-115,421,047); H4RE at −60 (duplication placed 2nd H1RE at −130) |
| Apolipoprotein C3 (ApoC-III) | Apolipoprotein C3 (APOC3) | Hepatocyte Nuclear Factor 4 RE (H4RE) | Hepatocyte Nuclear Factor 4 alpha (HNF4α) | nuclear hormone receptor | hepatocytes | NM_000040 (Chr11: 116,700,624-116,703,787); H4REs at −690 (distal) and −70 (proximal) |

TABLE 2

| Mammalian native promoters | Gene | Native RE used by native promoter | native transcription factor binding to RE | native transcription factor type | Cells targeted for expression by modified promoter (in nature, e.g. in gene therapy) | Gene Reference No. and location of the RE |
|---|---|---|---|---|---|---|
| Hepatocyte Nuclear Factor 4α P1 (proximal) | Hepatocyte Nuclear Factor 4α (HNF4A) | Hepatocyte Nuclear Factor 1 RE (H1RE) | Hepatocyte Nuclear Factor 1 alpha (HNF1α) | homeo-domain protein | hepatocytes | NM_000457 (Chr20: 43,029,924-43,060,029); −118/−106 |
| Albumin | Albumin (ALB) | Hepatocyte Nuclear Factor 1 RE (H1RE) | Hepatocyte Nuclear Factor 1 alpha (HNF1α) | homeo-domain protein | pancreatic β cells, intestinal mucosal cells, hepatocytes | NM_000477 (Chr4: 74,269,972-74,287,127); −322/−310 |
| Sodium-glucose cotransporter (SGLT1) | Sodium-glucose cotransporter (SLC5A1; glu-gal maladsorption) | Hepatocyte Nuclear Factor 1 RE (H1RE) | Hepatocyte Nuclear Factor 1 alpha (HNF1α) | homeo-domain protein | intestinal mucosal cells, renal proximal tubules | NM_000343 (Chr22: 32,439,019-32,509,009); +160/+172 (From translation start −73/−61) |
| Coagulation Factor VIII (procoagulant | F8 (X-linked hemophilia) | Hepatocyte Nuclear Factor 4 RE (H4RE) | Hepatocyte Nuclear Factor 4 alpha (HNF4α) | nuclear hormone receptor | hematopoietic cells | NM_019863 (ChrX: 154,064,070-154,114,577); −123/−111 |
| Acyl CoA dehydrogenase, C-4 to C-12 straight chain | ACADM (Medium-chain AcylCoA DH deficiency: lethargy, brain damage) | Hepatocyte Nuclear Factor 4 RE (H4RE) | Hepatocyte Nuclear Factor 4 alpha (HNF4α) | nuclear hormone receptor | hepatocytes | NM_000016 (Chr1: 76,190,043-76,229,353); −89/−77 |

TABLE 2-continued

| Mammalian native promoters | Gene | Native RE used by native promoter | native transcription factor binding to RE | native transcription factor type | Cells targeted for expression by modified promoter (in nature, e.g. in gene therapy) | Gene Reference No. and location of the RE |
|---|---|---|---|---|---|---|
| UDP-glucuronosyl-transferase 1 | UGT1A9 (mutations disrupt bilirubin metabolism) | Hepatocyte Nuclear Factor 4 RE (H4RE) | Hepatocyte Nuclear Factor 4 alpha (HNF4α) | nuclear hormone receptor | hepatocytes | NM_021027 (Chr2: 234,580,544-234,681,949); −335/−323 |
| ATP-binding cassette, sub-family C (ABCC) | ABCC6 (mutations cause pseudoxanthoma elasticum) | Hepatocyte Nuclear Factor 1 RE (H1RE) | Hepatocyte Nuclear Factor 4 alpha (HNF4α) | nuclear hormone receptor | epidermal cells, endothelial cells | NM_001079528 (Chr16: 16,315,045-16,317,328); −129/−117 |
| Pyruvate carbolylase | PC (deficiency causes lactic acidosis, a life-shortening disorder) | Cyclic AMP (cAMP) RE (CRE) | CREB (cAMP RE binding protein) | basic-leucine zipper (bZIP) | hepatocytes | NM_000920 (Chr11: 66,615,997-66,725,847); −1,803/−1,706 |

TABLE 3

| Mammalian native promoters | Gene | Native RE used by native promoter | native transcription factor binding to RE | native transcription factor type | Cells targeted for expression by modified promoter (in nature, e.g. in gene therapy) | Gene Reference No. and location of the RE |
|---|---|---|---|---|---|---|
| Actin, α1, skeletal muscle | ACTA1 | E-box (CAnnTG or CACGTG) | MyoD | basic helix-loop-helix (bHLH) | muscle cells, myocytes, pre-myocytes | NM_001100 (Chr1: 229,566,995-229,569,843); −320, −352, −475 |
| Myocyte enhander factor 2A | MEF2A | E-box (CAnnTG or CACGTG) | MyoD | basic helix-loop-helix (bHLH) | muscle cells, myocytes, pre-myocytes | NM_005587 (Chr15: 100,106,133-100,256,627); −211, −362 |
| Catenin β | CTNNB1 | E-box (CAnnTG or CACGTG) | MyoD | basic helix-loop-helix (bHLH) | muscle cells, myocytes, pre-myocytes | NM_001904 (Chr3: 41,240,942-41,281,939); −335, −515, −570 |
| OVO homologue-like 1, putative transcription factor | OVOL1 | E-box (CAnnTG or CACGTG) | Neurogenin-3 (Ngn3) | basic helix-loop-helix (bHLH) | pancreatic β cells | NM_004561 (Chr11: 65,554,529-65,564,683); numerous; adjacent pairs: −835 & −850, −1226 & −1244, −1863 & −1878 |
| Toll-like receptor 10 (TLR10) | TLR10 (Treg cell target gene) | Forkhead homeobox (FKH) element: TRTTTRT (R = G/A) | FoxP3 (mutations are implicated in autoimmunity) | winged helix (sub-group of helix-turn-helix) | hematopoietic cells | NM_030956 (Chr4: 38,774,263-38,784,589); multiple sites: −981/−975, −2155/−2149, −2221/−2215, −3019/−3013, −3027/−3021 |
| Heat shock 70 kDa protein 1A | HSPA1A | Heat shock element (HSE); inverted repeats of NGAAN | Heat shock factor-1 (HSF1) | heat-shock TF (leucine-zipper tetramer) | cryopreserved cells | NM_005345 (Chr6_apd_hap1: 3,098,052-3,100,478); several inverted repeats; two adjacent repeats at −90/−79, −796/−785 |

TABLE 4

| Mammalian native promoters | Gene | Native RE used by native promoter | native transcription factor binding to RE | native transcription factor type | Cells targeted for expression by modified promoter (in nature, e.g. in gene therapy) | Gene Reference No. and location of the RE |
|---|---|---|---|---|---|---|
| Phenylalanine hydroxylase | PAH (PKU) | HNF1 | H1RE | Homeodomain | Hepatocytes | NM_000277 (Chr12: 103,232,104-103,311,381); Two distal sites: −2950/−2948, −3882/−3870 |
| Acyl-CoA dehydrogenase, very long chain | ACADVL | Peroxisome proliferator-activated receptor (PPAR) | PPARg | Nuclear hormone receptor | Hepatocytes, other cells | NM_000018 (Chr17: 7,123,153-7,128,584); −525/−503 (plus a few other more distal sites) |
| | | Sterol regulatory element (SRE) | Sterol regulatory element-binding protein (SREBP) | Basic helix-loop-helix leucine zipper (bHLH-LZ) | Hepatocytes, other cells | NM_000018 (Chr17: 7,123,153-7,128,584); multiple sites; −216/−202 & −682/−668 (most distal) |

TABLE 4-continued

| Mammalian native promoters | Gene | Native RE used by native promoter | native transcription factor binding to RE | native transcription factor type | Cells targeted for expression by modified promoter (in nature, e.g. in gene therapy) | Gene Reference No. and location of the RE |
|---|---|---|---|---|---|---|
| Cystic fibrosis trans-membrane conductance | CFTR (ABCC7) | H4RE | HNF4a | Nuclear hormone receptor | Epithelial cells | NM_000492 (Chr7: 117,120,017-117,308,716); −991/−979 |
| | | CRE | CREB | bZIP | Epithelial | NM_000492 (Chr7: 117,120,017-117,308,716); +14/+21; −991/−984; −3148/−3141 |
| Adenosine deaminase | ADA (adenosine deaminase deficiency; ADA-SCID) | Winged helix binding site | Not identified to date? | Winged helix TFs | Hematopoietic cells | NM_000022 (Chr20: 43,248,164-43,280,376); Two sites, 0.23-kb spacing: −117/−107 & −339/−349 (reverse) |
| Regulatory factor X, 6 (RFX6) | RFX6 (mutations lead to neonatal diabetes) | PDX1 RE (TAAT) | Pancreatic duodenal homeobox-1 (PDX1) | Homeodomain | Pancreatic b cells | NM_173560 (Chr6: 117,198,376-117,253,308); two overlapping REs with opposite orientations: −1996/−2014 & −2019/−2001 |
| | | PTF1 RE (E-box "CAnnTG" plus "TGGGA") | Pancreas transcription factor 1 (PTF1) | Trimeric bHLH transcription factor | Pancreatic b cells | NM_173560 (Chr6: 117,198,376-117,253,308); Two proximal sites: −179/−159 & −348/−368 (reverse) |

TABLE 5

| SEQ. ID. NO: | Sequence of RE | Native Gene | RE |
|---|---|---|---|
| 35 | GATTAACCATTAAC | Hepatocyte Nuclear Factor 4a (HNF4A) | H1RE |
| 36 | GGTTACTCTTTAACG | HNF4A P2 | H1RE |
| 37 | GGCTAATTTTTAACA | HNF4A P2 | H1RE |
| 38 | GGTTAATATTCACCA | human alpha1-AT | H1RE |
| 39 | GGTTAGTAATTACTA | human albumin | H1RE |
| 40 | AGTTAATATTTAATA | human beta fibronogen | H1RE |
| 41 | AGTCCAAAGTTCA | Hepatocyte Nuclear Factor 1 alpha (HNF1α) | H4RE |
| 42 | ATGCCAAAGTTAA | G6Pase distal RE | H4RE |
| 43 | AGTCCAAAGGTTA | HNF1β (TCF2) RE | H4RE |
| 44 | AGTCCAAAGATCA | G6Pase proximal RE | H4RE |
| 45 | GGGGCAAAGGCC | Human Apolipoprotein C3 | H4RE |
| 46 | TGGGCAAACCTCA | Human Apolipoprotein C3 | H4RE |
| 47 | GTCCAAAGATCA | G6Pase proximal RE | H4RE |
| 48 | ATCACCCCAC | | SRE |

TABLE 6

| Promoters used in commercial vectors (organism) | Example commercial vector | Promoter type or structure | Relevant REs present in promoter | Respective transcription factors (TF type) | Other information |
|---|---|---|---|---|---|
| Cytomegalovirus immediate early (CMV-IE) | pcDNA series (Invitrogen) | Viral promoter | Several CREs, E-boxes, GC-boxes, SREs (serum-response elements), etc. | CREBP (cAMP RE binding protein), bHLH TFs e.g. E2F and c-myc (E-boxes), SP1 (GC-boxes), serum response factor (SRF, mitogen-activated protein kinase activated TF) | |
| GAL4 UAS/ E1b TATAA | pGene/V5-His (GeneSwitch System, Invitrogen) | Adenovirus E1b TATAA box fused to 6xGAL4 elements (two 3x units, 2-bp internal spacing, 15 bp apart) | GAL4 element: YGGnnnnnnnnnnnCCG (only found in yeast; Y = C, T) | "Switch": Chimeric protein comprised of yeast GAL4 DNA-binding domain, progesterone receptor ligand-binding domain (activated by mifepristone), and human NF-κB activation domain (Rel homology TF) | Synthetic mifepristone-inducible promoter; promoter activation requires transient or stable co-expression of chimeric Switch protein from a separate vector plus ligand |

TABLE 6-continued

| Promoters used in commercial vectors (organism) | Example commercial vector | Promoter type or structure | Relevant REs present in promoter | Respective transcription factors (TF type) | Other information |
|---|---|---|---|---|---|
| Human EF-1α promoter | pEF1 series (Invitrogen) | Human elongation factor 1α subunit promoter, yields high expression in a broad range of species and cell | 6 Sp1 sites (GC box, SGGGCGGRRY) and an Ap-1 site (TGASTCA) in intron 1 [S = G, C] | Sp1 (zinc-finger TF) and AP-1 (activator protein 1, bZIP TF) are ubiquitous TFs | |
| TOPFlash | STF (for Super Top Flash; Clontech?) | Synthetic TATAA box fused to 7 copies T-cell factor/ lymphoid enhancer-binding factor | TCF/LEF binding sites: GATCAAAGG | TCF/LEF binds to RE and recruits β-catenin RE | Wnt pathway reporter |

We claim:

1. An engineered DNA construct for increasing gene expression from a transcription factor (TF) dependent promoter comprising at least two transcription factor response element (TFRE) segments, wherein the at least two segments are separated by 200-700 base-pairs, wherein each segment comprises between four and 16 consecutive TFREs, wherein each of the TFREs is separated by about 9 to 15 base-pairs (bp), wherein all of the TFREs are response elements (REs) for one transcription factor (TF), and wherein the TF is a transcription activator.

2. The engineered DNA construct of claim 1, wherein the engineered DNA construct is operably linked upstream (5') of an ATG start codon of a target gene that is operably linked to a TF dependent promoter.

3. The engineered DNA construct of claim 1, wherein the TF is a selected from a group of consisting of homeo-domain type, nuclear hormone receptor type, basic-leucine zipper type (bZIP), winged helix type, and heat-shock type TF.

4. The engineered DNA construct of claim 3, wherein the TF is a homeo-domain type TF.

5. The engineered DNA construct of claim 4, wherein the homeo-domain type TF is a hepatocyte nuclear factor 1 alpha (HNF1α) TF.

6. The engineered DNA construct of claim 3, wherein the TF is a nuclear hormone receptor type TF.

7. The engineered DNA construct of claim 6, wherein the nuclear hormone receptor type TF is a hepatocyte nuclear factor 4 alpha (HNF4α).

8. A vector comprising the engineered DNA construct of claim 1.

9. An engineered DNA construct for increasing gene expression from a transcription factor (TF) dependent promoter comprising at least two transcription factor response element (TFRE) segments, wherein each segment comprises between four and 16 consecutive TFREs, wherein each of the TFREs is separated by about 9 to 15 base-pairs (bp), wherein all of the TFREs are response elements (REs) for one transcription factor (TF), wherein the TF is a transcription activator that is a homeo-domain type TF, and wherein the homeo-domain type TF is a hepatocyte nuclear factor 1 alpha (HNF1α) TF.

10. The engineered DNA construct of claim 9, wherein the at least two segments are separated by 200-700 base-pairs.

11. An engineered DNA construct for increasing gene expression from a transcription factor (TF) dependent promoter comprising at least two transcription factor response element (TFRE) segments, wherein each segment comprises between four and 16 consecutive TFREs, wherein each of the TFREs is separated by about 9 to 15 base-pairs (bp), wherein all of the TFREs are response elements (REs) for one transcription factor (TF), wherein the TF is a transcription activator that is a nuclear hormone receptor type TF.

12. The engineered DNA construct of claim 11, wherein the at least two segments are separated by 200-700 base-pairs.

13. The engineered DNA construct of claim 11, wherein the nuclear hormone receptor type TF is a hepatocyte nuclear factor 4 alpha (HNF4α).

* * * * *